US010633714B2

(12) United States Patent
Cutcliffe et al.

(10) Patent No.: US 10,633,714 B2
(45) Date of Patent: Apr. 28, 2020

(54) METHODS AND SYSTEMS FOR MICROBIOME CHARACTERIZATION, MONITORING AND TREATMENT

(71) Applicant: Pendulum Therapeutics, Inc., San Francisco, CA (US)

(72) Inventors: Colleen Cutcliffe, Menlo Park, CA (US); John S. Eid, San Francisco, CA (US); James H. Bullard, San Francisco, CA (US)

(73) Assignee: Pendulum Therapeutics, Inc., San Francisco, CA (US)

( * ) Notice: Subject to any disclaimer, the term of this patent is extended or adjusted under 35 U.S.C. 154(b) by 0 days.

(21) Appl. No.: 14/437,133

(22) PCT Filed: Jul. 21, 2014

(86) PCT No.: PCT/US2014/047491
§ 371 (c)(1),
(2) Date: Apr. 20, 2015

(87) PCT Pub. No.: WO2015/013214
PCT Pub. Date: Jan. 29, 2015

(65) Prior Publication Data
US 2015/0259728 A1 Sep. 17, 2015

Related U.S. Application Data

(60) Provisional application No. 61/856,711, filed on Jul. 21, 2013.

(51) Int. Cl.
*C12Q 1/689* (2018.01)
(52) U.S. Cl.
CPC ........ *C12Q 1/689* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

| | | |
|---|---|---|
| 3,625,214 A | 12/1971 | Higuchi |
| 4,789,734 A | 12/1988 | Pierschbacher |
| 4,897,268 A | 1/1990 | Tice et al. |
| 4,906,474 A | 3/1990 | Langer et al. |
| 4,925,673 A | 5/1990 | Steiner et al. |
| 5,075,109 A | 12/1991 | Tice et al. |
| 5,744,134 A | 4/1998 | Paul |
| 5,811,128 A | 9/1998 | Tice et al. |
| 5,814,344 A | 9/1998 | Tice et al. |
| 5,820,883 A | 10/1998 | Tice et al. |
| 5,853,763 A | 12/1998 | Tice et al. |
| 5,928,647 A | 7/1999 | Rock |
| 5,942,252 A | 8/1999 | Tice et al. |
| 6,241,983 B1 | 6/2001 | Paul et al. |
| 6,960,341 B2 | 11/2005 | Viscomi et al. |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,101,565 B2 | 9/2006 | Monte |
| 7,195,906 B2 | 3/2007 | Collins et al. |
| 7,785,581 B2 | 8/2010 | Cui |
| 8,329,672 B2 | 12/2012 | Rull et al. |
| 8,343,482 B2 | 1/2013 | Bergonzelli et al. |
| 8,557,233 B2 | 10/2013 | MacSharry et al. |
| 8,709,398 B2 | 4/2014 | MacSharry et al. |
| 8,802,179 B2 | 8/2014 | Miller |
| 8,906,668 B2 | 12/2014 | Henn et al. |
| 8,951,512 B2 | 2/2015 | Blaser et al. |
| 9,011,834 B1 | 4/2015 | McKenzie et al. |
| 9,028,841 B2 | 5/2015 | Henn et al. |
| 9,173,910 B2 | 11/2015 | Kaplan et al. |
| 9,180,147 B2 | 11/2015 | McKenzie et al. |
| 9,259,447 B2 | 2/2016 | Burcelin et al. |
| 2006/0115465 A1 | 6/2006 | MacFarlane et al. |
| 2010/0331641 A1* | 12/2010 | Bangera ................ A61B 1/041 600/345 |
| 2012/0004111 A1* | 1/2012 | Colwell ................. G06F 19/22 506/2 |
| 2012/0107291 A1 | 5/2012 | Burcelin et al. |

(Continued)

FOREIGN PATENT DOCUMENTS

| | | |
|---|---|---|
| JP | 2006191922 A | 7/2006 |
| WO | WO-0188095 A1 | 11/2001 |

(Continued)

OTHER PUBLICATIONS

Man et al. The Internal Transcribed Spacer Region, a New Tool for Use in Species Differentiation and Delineation of Systematic Relationships within the Campylobacter Genus. Applied and Environmental Microbiology, May 2010, vol. 76, No. 10, p. 3071-3081 (Year: 2010).*
Hyone-Myong Eun, 1-Enzymes and Nucleic Acids: General Principles, in Enzymology Primer for Recombinant DNA Technology, Academic Press, San Diego, pp. 1-108, ISBN 9780122437403, https://doi.org/10.1016/B978-012243740-3/50004-1 (Year: 1996).*
Rajendhran et al. Microbial phylogeny and diversity: Small subunit ribosomal RNA sequence analysis and beyond. Microbiological Research, vol. 166, p. 99-110; (Year: 2011).*
Loman et al. High-throughput bacterial genome sequencing: an embarrasment of choice, a world of opportunity. Nature Reviews, Sep. 2012, vol. 10, p. 599-606 (Year: 2012).*
Fichot et al. Microbial phylogenetic profiling with the Pacific Biosciences sequencing platform. Microbiome, Mar. 4, 2013, vol. 1, No. 10, p. 1-5 (Year: 2013).*

(Continued)

Primary Examiner — Olivia M. Wise
(74) Attorney, Agent, or Firm — Wilson Sonsini Goodrich & Rosati

(57) ABSTRACT

The present disclosure provides methods for profiling a microbiome and therapeutic compositions for treatment. Additionally, the methods, systems, compositions and kits provided herein are directed to assessing or predicting health status in a subject. Some of the embodiments include generating a report.

13 Claims, 8 Drawing Sheets

Specification includes a Sequence Listing.

(56) References Cited

U.S. PATENT DOCUMENTS

| | | |
|---|---|---|
| 2012/0230956 A1 | 9/2012 | McLean et al. |
| 2013/0121968 A1 | 5/2013 | Quay et al. |
| 2013/0224155 A1 | 8/2013 | Kaplan et al. |
| 2014/0079676 A1 | 3/2014 | Olmstead |
| 2014/0093478 A1 | 4/2014 | Turnbaugh et al. |
| 2014/0147425 A1 | 5/2014 | Henn et al. |
| 2014/0286920 A1 | 9/2014 | Mayra-Makinen et al. |
| 2014/0294774 A1 | 10/2014 | Nieuwdorp et al. |
| 2015/0190435 A1 | 7/2015 | Henn et al. |
| 2015/0246081 A1 | 9/2015 | Morris |
| 2015/0306152 A1 | 10/2015 | Cani et al. |
| 2015/0306156 A1 | 10/2015 | Borody |
| 2015/0320805 A9 | 11/2015 | Honda et al. |
| 2016/0000838 A1 | 1/2016 | Harmsen et al. |
| 2016/0030494 A1 | 2/2016 | Henn et al. |
| 2016/0040215 A1 | 2/2016 | Henn et al. |

FOREIGN PATENT DOCUMENTS

| | | |
|---|---|---|
| WO | WO-2010146568 A2 | 12/2010 |
| WO | WO-2011135194 A2 | 11/2011 |
| WO | WO-2013050833 A1 | 4/2013 |
| WO | WO-2013142378 A1 | 9/2013 |
| WO | WO-2014082050 A1 | 5/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014153194 A2 | 9/2014 |
| WO | WO-2015013214 A2 | 1/2015 |
| WO | WO-2015051323 A1 | 4/2015 |
| WO | WO-2015067936 A1 | 5/2015 |
| WO | WO-2015067938 A1 | 5/2015 |
| WO | WO-2015067947 A1 | 5/2015 |
| WO | WO-2015067948 A1 | 5/2015 |
| WO | WO-2015067949 A1 | 5/2015 |
| WO | WO-2015077794 A1 | 5/2015 |
| WO | WO-2015095241 A2 | 6/2015 |
| WO | WO-2015189472 A1 | 12/2015 |

OTHER PUBLICATIONS

Turnbaugh et al. A core gut microbiome in obese and lean twins. Nature Letters, vol. 457, p. 480-484 (Year: 2009).*

Qin et al. A metagenome-wide association study of gut microbiota in type 2 diabetes. Nature 2012, vol. 490, pp. 55-60 (Year: 2012).*

Asano, et al. Critical role of gut microbiota in the production of biologically active, free catecholamines in the gut lumen of mice. Am J Physiol Gastrointest Liver Physiol. Dec. 1, 2012;303(11):G1288-95. doi: 10.1152/ajpgi.00341.2012. Epub Oct. 11, 2012.

Bravo, et al. Ingestion of Lactobacillus strain regulates emotional behavior and central GABA receptor expression in a mouse via the vagus nerve. Proc Natl Acad Sci U S A. Sep. 20, 2011;108(38):16050-5. doi: 10.1073/pnas.1102999108. Epub Aug. 29, 2011.

Clarke, G. Society for Neuroscience (SfN) 2015 Annual Meeting. Abstract 162.04. Presented Oct. 18, 2015.

Karlsson, et al. Gut metagenome in European women with normal, impaired and diabetic glucose control. Nature. Jun. 6, 2013;498(7452):99-103. doi: 10.1038/nature12198. Epub May 29, 2013.

Messaoudi, et al. Assessment of psychotropic-like properties of a probiotic formulation (Lactobacillus helveticus R0052 and Bifidobacterium longum R0175) in rats and human subjects. Br J Nutr. Mar. 2011;105(5):755-64. doi: 10.1017/S0007114510004319. Epub Oct. 26, 2010.

Naruszewicz, et al. Effect of Lactobacillus plantarum 299v on cardiovascular disease risk factors in smokers. Am J Clin Nutr. Dec. 2002;76(6):1249-55.

Parnell, et al. Weight loss during oligofructose supplementation is associated with decreased ghrelin and increased peptide YY in overweight and obese adults. Am J Clin Nutr. Jun. 2009;89(6):1751-9. doi: 10.3945/ajcn.2009.27465. Epub Apr. 22, 2009.

Queipo-Ortuno, et al. Gut microbiota composition in male rat models under different nutritional status and physical activity and its association with serum leptin and ghrelin levels. PLoS One. May 28, 2013;8(5):e65465. doi: 10.1371/journal.pone.0065465. Print 2013.

Ravussin, et al. Responses of gut microbiota to diet composition and weight loss in lean and obese mice. Obesity (Silver Spring). Apr. 2012;20(4):738-47. doi: 10.1038/oby.2011.111. Epub May 19, 2011.

Reigstad, et al. Gut microbes promote colonic serotonin production through an effect of short-chain fatty acids on enterochromaffin cells. Apr. 2015, The FASEB Journal, vol. 29, No. 4, pp. 1395-1403.

Roshchina, V. Evolutionary Considerations of Neurotransmitters in Microbial, Plant, and Animal Cells. In: Lyte M, Fitzgerald P (eds). Microbial Endocrinology: Interkingdom Signaling in Infectious Disease and Health. New York: Springer, Feb. 2010, pp. 17-52.

Vrieze, et al. Transfer of intestinal microbiota from lean donors increases insulin sensitivity in individuals with metabolic syndrome. Gastroenterology. Oct. 2012;143(4):913-6.e7. doi: 10.1053/j.gastro.2012.06.031. Epub Jun. 20, 2012.

Yadav, et al. Beneficial metabolic effects of a probiotic via butyrate-induced GLP-1 hormone secretion. J Biol Chem. Aug. 30, 2013;288(35):25088-97. doi: 10.1074/jbc.M113.452516. Epub Jul. 8, 2013.

International search report and written opinion dated Jan. 27, 2016 for PCT Application No. US2015/058511.

Louis et al. Diversity, metabolismand microbial ecology of butyrate-producing bacteria from the human large intestine. FEMS Microbial Lett. 2009, vol. 294(1), p. 1-8.

Puddu et al. Evidence for the Gut Microbiota Short-Chain Fatty Acids as Key Pathophysiologicat Molecules Improving Diabetes. Mediators Inflamm. vol. 2014;2014:162021. Epub Aug. 17, 2014.

Vital et al. Revealing the Bacterial Butyrate Synthesis Pathways by Analyzing (Meta)genomic Data. MBio. Apr. 22, 2014, vol. 5(2):e00889.

Yadav et al. Beneficial Metabolic Effects of a Probiotic via Butyrate-induced GLP-1 Hormone Secretion. J Biol Chem. 2013, vol. 288(35), p. 25088-97, Duplicate Reference.

Angelakis, et al. The relationship between gut microbiota and weight gain in humans. Future Microbiol. Jan. 2012;7(1):91-109. doi: 10.2217/fmb.11.142.

Ansel, et al. Pharmaceutical Dosage Forms and Drug Delivery Systems. Lippincott Williams & Wilkins, Baltimore, 1999.

Ausubel, et al. Current Protocols in Molecular Biology, 1987.

Bowman, et al. Analysis of Full-Length Metagenomic 16S Genes by SMRT Sequencing. American Society for Microbiology 2013 General Meeting May 19, 2013 Poster Session, pp. 116 Poster 390. Available on the internet: <http://www.asm.org/index.php/asm-events/post-meeting-materials [select ASM2013 Final Program, then pg Posters May 19, 2013 p. 116].

Brown, et al. Chemical synthesis and cloning of a tyrosine tRNA gene. Methods Enzymol. 1979;68:109-51.

Chin, et al. Nonhybrid, finished microbial genome assemblies from long-read SMRT sequencing data. Nat Methods. Jun. 2013;10(6):563-9. doi: 10.1038/nmeth.2474. Epub May 5, 2013.

Dolfing, et al. Acetate inhibition of methanogenic, syntrophic benzoate degradation. Appl Environ Microbiol. Jul. 1988;54(7):1871-3.

Eid, et al. Real-time DNA sequencing from single polymerase molecules. Science Jan. 2, 2009 vol. 323, No. 5910, pp. 113-138. Especially p. 134, col. 3, Para. 4, p. 136, fig 3B.

Freshney. Culture of Animal Cells: A Manual of Basic Technique and Specialized Applications. 6th Edition, 2010.

Gennaro. Remington: The Science and Practice of Pharmacy. Williams and Wilkins, 20th Edition, 2000.

Gregoriadis, G. Liposomes. Drug Carriers in Biology and Medicine, Chapter 14, pp. 2, sup. 87-341 (Academic Press, 1979).

International search report and written opinion dated Jan. 23, 2015 for PCT Application No. US 2014/047491.

Jain, K. Strategies and technologies for drug delivery systems. TIPS 19:155-157, 1998.

Kadooka, et al. Regulation of abdominal adiposity by probiotics (*Lactobacillus gasseri* SBT2055) in adults with obese tendencies in

(56) References Cited

OTHER PUBLICATIONS a randomized controlled trial. Eur J Clin Nutr. Jun. 2010;64(6):636-43. doi: 10.1038/ejcn.2010.19. Epub Mar. 10, 2010.
Lange, et al. Selected reaction monitoring for quantitative proteomics: a tutorial. Molecular Systems Biology (2008) 4:222.
McPherson, et al. Methods in Enzymology: PCR 2: A Practical Approach. Academic Press, Inc., 1995.
Millon, et al. Comparative meta-analysis of the effect of Lactobacillus species on weight gain in humans and animals. Microb Pathog. Aug. 2012;53(2):100-8. doi: 10.1016/j.micpath.2012.05.007. Epub May 24, 2012.
Narang, et al. Improved phosphotriester method for the synthesis of gene fragments. Methods Enzymol. 1979;68:90-8.
Sambrook, et al. Molecular Cloning: A Laboratory Manual. 4th Edition, 2012.
Schink, B. Energetics of syntrophic cooperation in methanogenic degradation. Microbiol Mol Biol Rev. Jun. 1997;61(2):262-80.
Zhang, et al. Human gut microbiota in obesity and after gastric bypass. Proc Natl Acad Sci U S A. Feb. 17, 2009;106(7):2365-70. doi: 10.1073/pnas.0812600106. Epub Jan. 21, 2009.
Bowman, et al. Analysis of Full-Length Metagenomic 16S Genes by SMRT Sequencing,[online], [retrieved on May 30, 2018], internet http://www.abstractsonline.com/Plan/ViewAbstract.aspx?mID=3214&sKey=962254b2-1264-4654-bda8-448842a81457&cKey=fff13337-29c2-4b77-97a4-4d474ef46f8b&mKey=15c31f4d-cba9-43a6-b6e1-2f312e144db4.
Saro, et al. Technical note: Comparison of automated ribosomal intergenic spacer analysis and denaturing gradient gel electrophoresis to assess bacterial diversity in the rumen of sheep. J Anim Sci. Mar. 2014;92(3):1083-8. doi: 10.2527/jas.2013-7175. Epub Feb. 3, 2014.
Gonzales-Marin, et al. Maternal oral origin of Fusobacterium nucleatum in adverse pregnancy outcomes as determined using the 16S-23S rRNA gene intergenic transcribed spacer region. J Med Microbiol. Jan. 2013 62(Pt 1):133-144. doi: 10.1099/jmm.0.049452-0. Epub Sep. 20, 2012.
Grattard, et al. Analysis of the genetic diversity of Legionella by sequencing the 23S-5S ribosomal intergenic spacer region: from phylogeny to direct identification of isolates at the species level from clinical specimens. Microbes Infect. Jan. 2006 8(1):73-83. Epub Aug. 8. 2005.
Collado, et al. (2007). Intestinal integrity and Akkermansia muciniphila, a mucin-degrading member of the intestinal microbiota present in infants, adults, and the elderly. Appl. Environ. Microbiol. 73, 7767-7770. doi: 10.1128/AEM.01477-07.
Eckburg, PB. et al., Diversity of the human intestinal microbial flora.Science. Jun. 10, 2005;308(5728):1635-8. Epub Apr. 14, 2005.
Stevenson, et al., New strategies for cultivation and detection of previously uncultured microbes. Appl Environ Microbiol. Aug. 2004;70(8):4748-55.

* cited by examiner

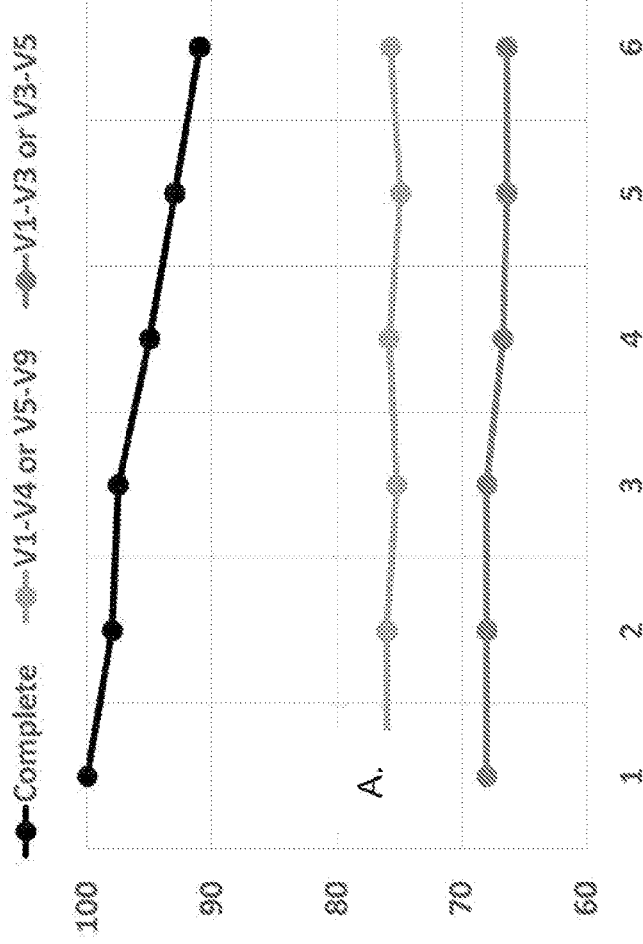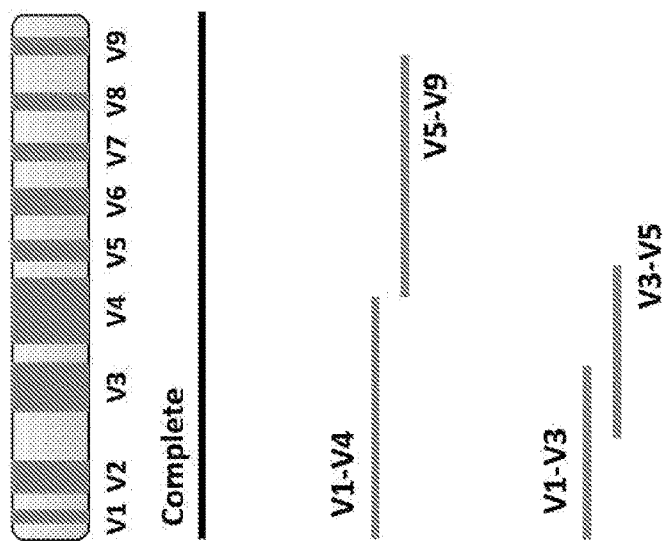
FIG. 2

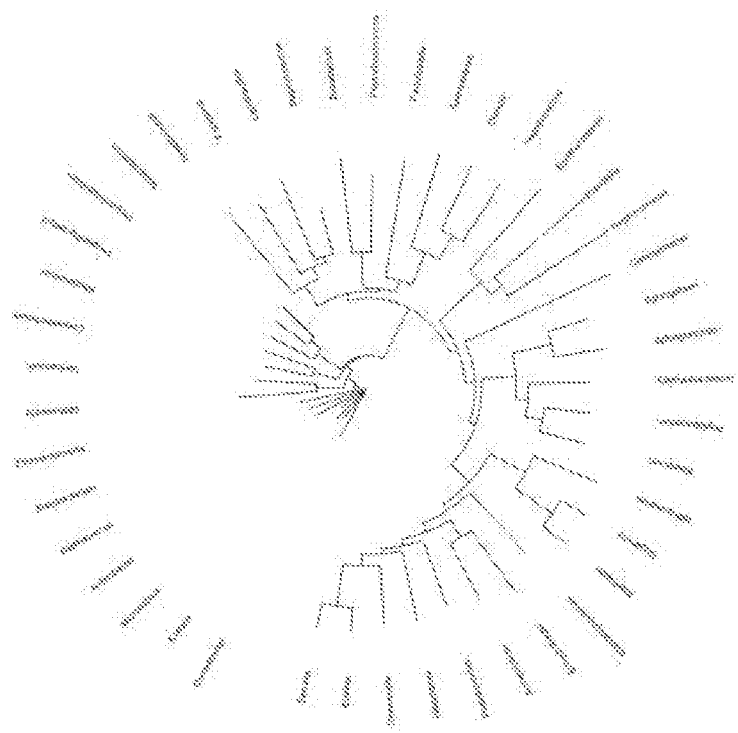
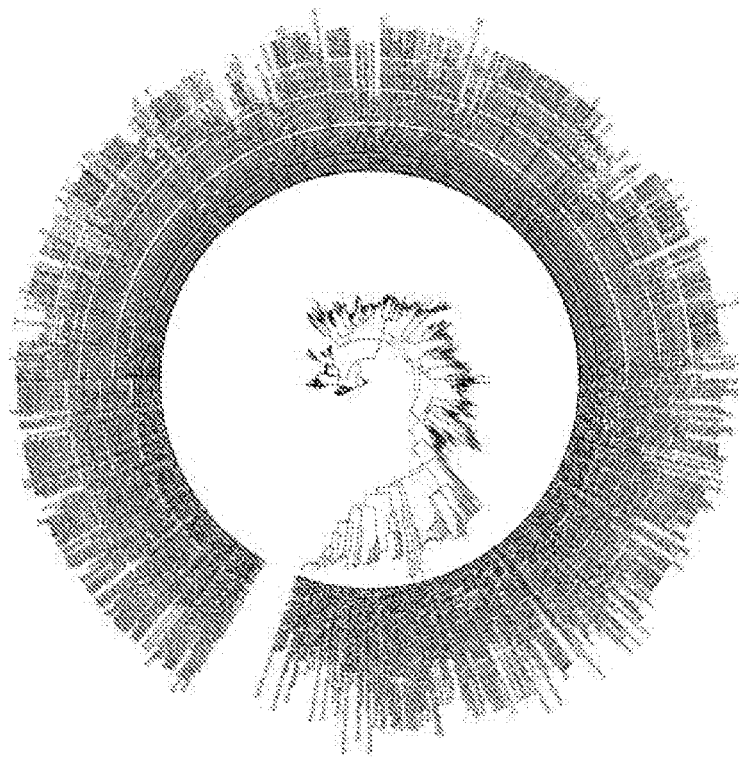
FIG. 6

METHODS AND SYSTEMS FOR MICROBIOME CHARACTERIZATION, MONITORING AND TREATMENT

CROSS-REFERENCE

This application is a National Phase Entry of International Application No. PCT/US2014/047491, filed Jul. 21, 2014, which claims the benefit of U.S. Provisional Application No. 61/856,711 filed on Jul. 21, 2013, each of which is incorporated herein by reference in its entirety.

SEQUENCES

The instant application contains a Sequence Listing which has been submitted electronically in ASCII format and is hereby incorporated by reference in its entirety. Said ASCII copy, created on Jul. 21, 2014, is named 46790-701.601_SL.txt and is 171,171 bytes in size

BACKGROUND OF THE DISCLOSURE

A typical healthy individual's body is inhabited with trillions of microbes across various body sites called microbiomes. Some examples of microbiome sites include skin, intestinal, stomach, gut, oral, conjunctival, and vaginal. To better understand the role of these microbiomes and how they affect physiology and disease state we can analyze what microbes comprise a microbiome and how they correlate or affect the health status and clinical response of an individual. For example, the human gut microbiome is known to play a key role in many health conditions, including obesity, gastrointestinal health, nutrient absorption, and drug metabolism among others. Owing to such discoveries, the NIH has invested $150 million in the analysis of the Human Microbiome Project over the next 5-years for analyzing the microbial composition of various human body sites.

Despite this awareness of the interrelation between microbiomes and health, the complexity of the microbiome, as well as difficulties in categorizing and characterizing the constituents of the microbiome have made understanding these relationships challenging. Consequently, these challenges have presented hurdles in the development of diagnostic and therapeutic applications.

Metagenomic approaches to understanding the microbiome stand to help further illuminate the roles of the microbiomes and have only recently been enabled by "next-generation" sequencing technologies. While the information uncovered by these studies will become increasingly valuable to those interested in targeting the microbiome for therapeutic interventions and consumer products, transforming this large amount of data into meaningful data that can be used to develop diagnostics and therapeutics presents a significant hurdle. Two apparent bottlenecks in harnessing the power of the microbiome, is the cost of undertaking these analyses and the intrinsic complexity of metagenomic analysis mentioned above.

The current gold standard in the field for taxonomic classification of bacterial species is through the DNA sequencing of the 16S ribosomal RNA (rRNA) subunit. The 16S rRNA subunit was chosen as an "ideal" target for classification because it is universally present in all bacteria and it contains nine variable regions which can be used to distinguish taxonomies. However, focusing solely on the 16S rRNA subunit presents its own technical challenges owing to the fact that some bacteria share the same variable regions resulting in misclassification.

Furthermore, current "second-generation" sequencing technologies being used to sequence the 16S rRNA subunit have read lengths which often yield incomplete coverage of theses variable regions. For example, sequencing by 454 gives average read lengths of 500 bp and Illumina's MiSeq and HiSeq platforms give average read lengths of 100-450 bp. With these read lengths, bacterial classification often suffer from issues of accuracy, especially in a complex metagenomic sample such as a microbiome sample.

The present disclosure provides solutions to these limitations by providing methods, systems, compositions, and kits that yield more accurate information and hence more accurate classification of a microbiome. Such information allows for multiplex and efficiency advantages over the current technology and the development of consumer products such diagnostic tests, therapeutics and probiotic therapies.

SUMMARY OF THE INVENTION

The present disclosure provides a method of classifying a microbe, comprising: obtaining a nucleic acid sequence of a 16S or 23S ribosomal subunit contained within a single read length of a first microbe; and comparing said nucleic acid sequence of a first microbe to a reference; and identifying the first microbe at the strain level or sub-strain level based on the comparing.

The present disclosure provides a method of profiling a microbiome in a subject, comprising: obtaining nucleic acids sequences of a 16S ribosomal subunit from at least one microbe in a biological sample obtained from the subject; analyzing said at least one microbe within said biological sample based upon the nucleic acids sequences obtained; and determining a profile of the microbiome based on said analyzing. In some embodiments, determining a profile of the microbiome in said subject can be based on 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, 100 or fewer microbes, 200 or fewer microbes, 300 or fewer microbes, 400 or fewer microbe, 500 or fewer microbes, 600 or fewer microbes, 700 or fewer microbes, or 800 or fewer microbes. In some embodiments determining a profile of the microbiome in said subject has an accuracy greater than 70% based on the measurements. In some embodiments, the method can further comprise obtaining nucleic acids sequences of from at least one microbe in a biological sample taken at least two different points of time. In some embodiments, analyzing uses long read sequencing platforms.

The present disclosure provides a method of profiling a microbiome in a subject, comprising: obtaining nucleic acids sequences of a 16S and 23S ribosomal subunit from at least one microbe in a biological sample obtained from said subject; analyzing said at least one microbe within said biological sample based upon the sequences obtained; and determining a profile of the microbiome in said subject based on said analyzing. In some embodiments, determining a profile of the microbiome in said subject can be based on 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, 100 or fewer microbes, 200 or fewer microbes, 300 or fewer microbes, 400 or fewer microbe, 500 or fewer microbes, 600 or fewer microbes, 700 or fewer microbes, or 800 or fewer microbes. In some embodiments, determining a profile of the microbiome in said subject has an accuracy greater than 70% based on the measurements. In some embodiments, the method can further comprising obtaining nucleic acids sequences of from at least one microbe in a biological sample taken at least two different points of time. In some embodiments, analyzing uses long read sequencing platforms.

The present disclosure provides a method of determining metabolic pathways that are indicative of a health status in a subject, comprising: obtaining RNA sequences from a biological sample from a subject, such that the entire transcript is contained within a single read length; analyzing said transcripts by a sequencing method; comparing the sequenced transcripts to a reference; and determining the metabolic pathways that are indicative of a health status. In some embodiments, analyzing uses long read sequencing platforms.

The present disclosure provides a method of treating a disease in a subject, comprising: measuring a microbiome profile in a biological sample obtained from the subject, wherein the microbiome profile comprises at least one microbe; detecting a presence or absence of the disease in the subject based upon said measuring; and treating the disease in the subject based upon said detecting.

The present disclosure provides a method, comprising: obtaining data comprising a measurement of a microbiome panel in a biological sample obtained from a subject, wherein said microbiome panel comprises at least two microbes; generating a microbiome profile of said microbiome panel based upon the measurement data; comparing said microbiome profile of said microbiome panel to a reference profile; and determining a likelihood of a disease status in said subject based said comparing.

The present disclosure provides a method, comprising: obtaining data comprising a measurement of a microbiome panel in a biological sample obtained from a subject, wherein said microbiome panel comprises at least two microbes; generating a microbiome profile of said microbiome panel based upon the measurement data; comparing said microbiome profile of said microbiome panel to a threshold level of a reference; and determining a likelihood of a disease status in said subject based on said comparing of at least one threshold level of a reference of said microbiome panel.

The present disclosure provides a method of diagnosing a subject a disease in a subject, comprising: measuring a microbe panel in a biological sample obtained from the subject, wherein the microbiome panel comprises at least one microbe; detecting a presence or absence of a disease state in said subject based upon said measuring; and; recommending to the subject at least one microbial-based therapeutic or cosmetic for treatment of said disease based on the detecting. In some embodiments, detecting a presence or absence of said disease state with a sensitivity that is greater than 70%. In some embodiments, detecting a presence or absence said disease state with a sensitivity and specificity that is greater than 70%. In some embodiments, comprising detecting a presence or absence said disease state with a sensitivity that is greater than 75%, 80%, 85%, 90%, or 95%. In some embodiments, detecting a presence or absence said disease state with a sensitivity and specificity that is greater than 75%, 80%, 85%, 90%, or 95%. In some embodiments, the panel of microbes comprise 2 or fewer microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, or 40 or fewer microbes.

The present disclosure provides a computer system for determining a microbiome profile in a subject, the computer system comprising: a memory unit for receiving data comprising measurement of a microbe panel from a biological sample of the subject, wherein the microbe panel comprises at least one marker of a microbe; computer-executable instructions for analyzing the measurement data according to a method of any of the preceding claims; and computer-executable instructions for determining a presence or absence of at least disease in the subject based upon said analyzing. In some embodiments, the computer system further comprises computer-executable instructions to generate a report of the presence or absence of the at least one disease in the subject. In some embodiments, computer system can further comprises a user interface configured to communicate or display said report to a user.

The present disclosure provides a computer readable medium comprising: computer-executable instructions for analyzing data comprising measurement of a microbiome profile from a biological sample obtained from a subject, wherein the microbiome profile comprises at least one marker selected from at least one microbe; and computer-executable instructions for determining a presence or absence of at least disease in the subject based upon the analyzing.

The present disclosure provides a kit, comprising: one or more compositions for use in measuring a microbiome profile in a biological sample obtained from a subject, wherein the microbiome profile comprises at least one marker to at least one microbe; and instructions for performing a method of any of the preceding claims. In some embodiments, a kit can further comprises a computer readable medium.

Any of the methods provided herein can include embodiments in wherein the disease is inflammatory bowel disease (IBD), preterm labor, obesity, diabetic foot ulcers, bacteremia, acne, infantile colic, type II diabetes, C. difficile, irritable bowel syndrome (IBS), asthma, autism, psoriasis, allergies, cardiovascular disease, cancer depression, cystic fibrosis, multiple sclerosis, urinary tract infection, radiation enteropathy, drug metabolism, chronic fatigue, type I diabetes, halitosis, and tooth decay.

Any of the methods provided herein can include embodiments wherein the biological sample is taken from a microbiome is selected from the group skin microbiome, umbilical microbiome, vaginal microbiome, conjunctival microbiome, intestinal microbiome, stomach microbiome, gut microbiome, oral microbiome, nasal microbiome, gastrointestinal tract microbiome, urogenital tract microbiome, or a combination thereof.

Any of the methods provided herein can include embodiments wherein the microbiome panel comprises a microbial marker of the 16S or 23S ribosomal subunit, or wherein the microbiome panel comprises a microbial marker to the entire 16S or 23S ribosomal subunit transcript, or wherein the microbiome panel comprises a microbial marker of the entire 16S or 23S ribosomal subunit transcript and the intergenic region between said 16S or 23S ribosomal subunit transcript, or wherein the microbiome panel comprises a microbial marker of at least one variable region of the 16S or 23S ribosomal subunit.

Any of the methods provided herein can include embodiments wherein the measuring comprises detecting or measuring a level of a fragment, antigen, or binding partner of the 16S or 23S ribosomal subunit, or wherein the measuring comprises detecting or measuring a level of a fragment, antigen, or binding partner of a16S or 23S ribosomal subunit variable region.

Any of the methods provided herein can include embodiments wherein the subject is a human subject, or wherein the subject is asymptomatic for a disease, or wherein the subject is presenting with at least one clinical symptom for said disease.

Any of the methods provided herein can include embodiments wherein measuring comprises use of at least one of: an immunoassay, flow cytometry assay, biochip assay, microarray assay, and sequencing assay. Any of the methods provided herein can include embodiments wherein measuring comprises detecting or measuring a level of a microbe. Any of the methods provided herein can include embodiments wherein measuring comprises detecting or measuring a level of a marker on a microbe.

Any of the methods provided herein can include embodiments wherein the disease state determined is a poor clinical outcome, a good clinical outcome, a high risk of disease, a low risk of disease, a complete response, a partial response, a stable disease, a non-response, or a recommended treatments for disease management.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A-2B depict simulation results in which the microbe classification accuracy (Y-axis) is plotted as a function of different 16S ribosomal amplicon target sizes. Bacterial sequences from the Ribosomal Database Project were used, with different sequencing platform error rates (X-axis). Utilizing the full 16S amplicon (top line) enables the highest classification accuracy for the practically realized error rates depicted (<5%).

FIG. 4A depicts strain level resolution data with a method described herein for the Nitrosomonas genus, in which the per strain divergence is concentrated in the V3, 4, and 5 regions of 16S FIG. 4B depicts strain level resolution data with a method described herein for the Staphylococcus genus, in which the per strain divergence is concentrated in the V8, and 9 regions of 16S.

FIG. 5A depicts how the methods of this disclosure can be used to quantify the successful application of the microbial therapeutic/cosmetic over time. The addition of a non-commensal strain to the consortia, aids in distinguishing applied strains from the background variation of individual microbiomes for that site (e.g. skin, gut, mouth, etc.). FIG. 5B depicts how the methods in the present disclosure can be used to discover stabilizing commensal strains. Those strains that when present, are correlated to the longevity of the applied consortia, would become candidates for expanding the initial consortia to produce formulations with increased stability and efficacy.

FIG. 6A depicts the resolution of a microbiome using current standard methods that resolve down to the genus level of a microbe comprising a microbiome FIG. 6B depicts the resolution of a microbiome using a method described herein that resolves down to the strain level of a microbe comprising a microbiome.

DETAILED DESCRIPTION OF THE DISCLOSURE

I. Definitions

Figure 1:
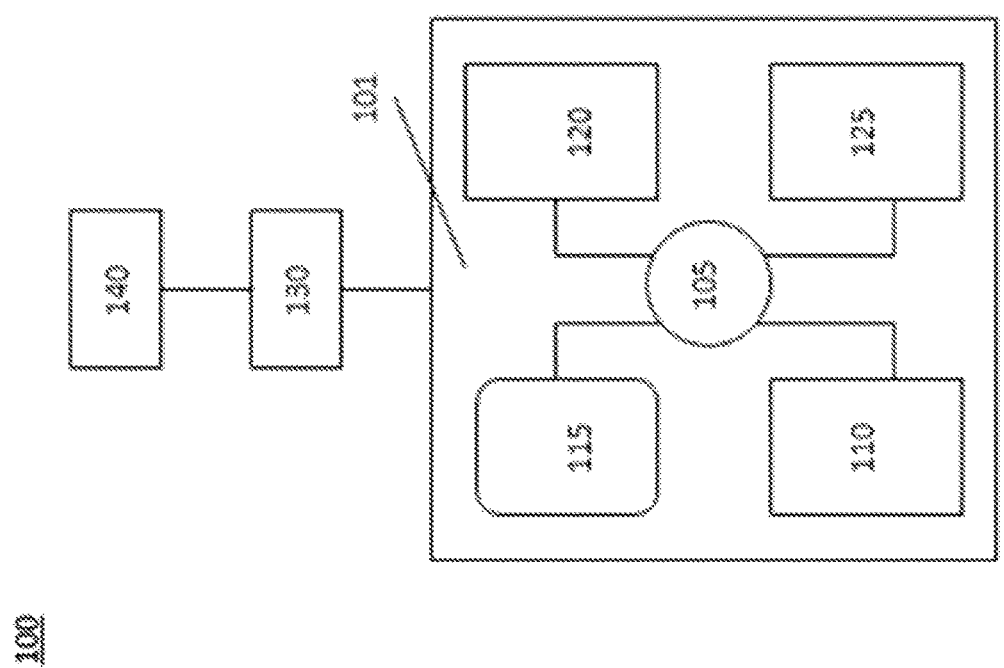
FIG. 1 depicts an exemplary computer system for implementing a method described herein. This includes a continually enlarging database of full rRNA operons as the methods described herein allow this to be expanded in a cost-effective manner that hasn't been previously available.

As used in the specification and claims, the singular forms "a", "an" and "the" include plural references unless the context clearly dictates otherwise. For example, the term "a sample" includes a plurality of samples, including mixtures thereof.

The term "microbes", "microorganisms" as used herein, refers to any single-celled organisms, bacteria, archaea, protozoa, and unicellular fungi.

The term "microbiome", as used herein, refers to the ecological community of commensal, symbiotic, or pathogenic microorganisms that inhabit a body space on a subject.

The terms "determining", "measuring", "evaluating", "assessing," "assaying," and "analyzing" can be used interchangeably herein to refer to any form of measurement, and include determining if an element is present or not. (e.g., detection). These terms can include both quantitative and/or qualitative determinations. Assessing may be relative or absolute. These terms can include use of the algorithms and databases described herein. "Detecting the presence of" can include determining the amount of something present, as well as determining whether it is present or absent. The term "genome assembly algorithm" as used herein, refers to any method capable of aligning short reads with reference sequences under conditions that a complete sequence of the genome may be determined.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence.

The term "sequencing" as used herein refers to sequencing methods for determining the order of the nucleotide bases—adenine, guanine, cytosine, and thymine—in a nucleic acid molecule (e.g., a DNA or RNA nucleic acid molecule.

The term "biochip" or "array" can refer to a solid substrate having a generally planar surface to which an adsorbent is attached. A surface of the biochip can comprise a plurality of addressable locations, each of which location may have the adsorbent bound there. Biochips can be adapted to engage a probe interface, and therefore, function as probes. Protein biochips are adapted for the capture of polypeptides and can be comprise surfaces having chromatographic or biospecific adsorbents attached thereto at addressable locations. Microarray chips are generally used for DNA and RNA gene expression detection.

The term "barcode" as used herein, refers to any unique, non-naturally occurring, nucleic acid sequence that may be used to identify the originating genome of a nucleic acid fragment.

The terms "subject," "individual" or "patient" are used interchangeably herein. A "subject" can be a biological entity containing expressed genetic materials. The biological entity can be a plant, animal, or microbe, including, e.g., bacteria, bacterial plasmids, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The terms "treatment" or "treating" are used interchangeably herein. These terms can refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

Overview

The present disclosure is generally directed to the identification, classification or quantification of at least one microbiome comprising comprehensive analysis of at least one of the 16S and 23S ribosomal RNA (rRNA) subunits or intergenic regions.

The present disclosure also provides for the determination of a microbiome profile of a subject. The methods, compositions, systems and kit can generate a cohort-generalized microbiome profile or a subject-specific microbiome profile. The microbial profile can have an accuracy of 70% or greater based on measurement of 15 or fewer microbes in the biological sample. Such profiling method can have at least an accuracy greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes, 200 or fewer microbes, 300 or fewer microbes, 400 or fewer microbes, 500 or fewer microbes, 600 or fewer microbes, 700 or fewer microbes, or 800 or fewer microbes.

Such microbiome profile can be used in part or solely to calculate a quantitative score. A quantitative score can also use the microbiome profile in combination with one or more clinical factors such as age group, ethnicity, sexual habits, hygiene habits, product use, dietary regimen, weight, gender, medical history, risk factors, or family history.

In some embodiments, a quantitative score can indicate an increased or decreased likelihood of one or more of: a poor clinical outcome, good clinical outcome, high risk of disease, low risk of disease, complete response, partial response, stable disease, non-response, and recommended treatments for disease management.

In some applications, a decrease or increase in one or more microbes' threshold values in a subject's microbiome profile indicates an increased likelihood of one or more of: a poor clinical outcome, good clinical outcome, high risk of disease, low risk of disease, complete response, partial response, stable disease, non-response, and recommended treatments for disease management. In some applications, a decrease or increase in one or more microbes' threshold values in a subject's microbiome indicates an increased likelihood of one or more of: a poor clinical outcome, good clinical outcome, high risk of disease, low risk of disease, complete response, partial response, stable disease, non-response, and recommended treatments for disease management.

Provided herein are microbial-based compositions that can be administered as therapeutic or as a cosmetic to a subject. Also provided herein are various formulations of the microbial-based compositions. One or more, or combinations of microbes or formulations provided herein can be used to develop appropriate compostions for treating a subject suffering from a condition. Any of the methods, compositions, kits, and systems described herein can be used to generate a therapeutic/cosmetics consumer product composition.

Any of the methods, compositions, kits, and systems described herein can be used to determine or predict disease status of a subject. Disease status can include such information as a poor clinical outcome, good clinical outcome, high risk of disease, low risk of disease, complete response, partial response, stable disease, non-response, and recommended treatments for disease management.

The methods, compositions, systems and kits described herein provide a diagnostic assay for a disease, as described herein, based on detection or measurement of one or more microbes in a biological sample or a microbiome profile obtained from a subject. In some applications, the biological sample is collected from a healthy subject who wants to determine one or more of their microbiome profiles. In some applications, the biological sample collected from a subject with a disease who wants to determine one or more of their microbiome profiles. Indications that can be used with the methods, compositions, systems and kits as described herein include, but are not limited to IBD, preterm labor, obesity, diabetic foot ulcers, bacteremia, acne, infantile colic, type 2 diabetes, C. difficile, IBS, asthma, autism, psoriasis, allergies, cardiovascular disease, cancer, depression, cystic fibrosis, multiple sclerosis, urinary tract infection, radiation enteropathy, drug metabolism, chronic fatigue, type 1 diabetes, halitosis, and tooth decay.

A biological sample can be any sample type from any microbiome on the body of a subject. Some examples of microbiomes that can be used with the present disclosure include the skin microbiome, umbilical microbiome, vaginal microbiome, conjunctival microbiome, intestinal microbiome, stomach microbiome, gut microbiome and oral microbiome, nasal microbiome, gastrointestinal tract microbiome, and the urogenital tract microbiome. Depending on the application the biological sample can be whole blood, serum, plasma, mucosa, saliva, cheek swab, urine, stool, cells, tissue, bodily fluid or a combination thereof.

The diagnostic assays or methods provided herein can have at least one of a sensitivity of greater than 70% and specificity of greater than 70% of a disease status, prediction of disease response or outcome. Such diagnostic methods can have at least one of a sensitivity of 70% or greater and specificity of greater than 70% based on measurement of 15 or fewer microbes in the biological sample. Such diagnostic assays or method can have at least one of a sensitivity greater than 70% and specificity greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes.

The methods, compositions, systems and kits described herein can be used to generate a report. In some applications, a report can include information such as the degree of likelihood (increase or decrease) of one or more of health status of a disease state: presence or absence of a disease state, a poor clinical outcome, good clinical outcome, high risk of disease, low risk of disease, complete response, partial response, stable disease, non-response, and recommended treatments for disease management.

An exemplary method can comprise at least one of the following steps: obtaining a biological sample from a subject; measuring a panel of microbes in the biological sample of the subject; determining a disease status upon the measuring; and generating a report that provides information of disease status upon the results of the determining.

An exemplary method of the present disclosure can comprise at least one of the following steps: obtaining a biological sample from a subject, measuring a panel of microbes in the biological sample of the subject, determining a presence or absence at least one microbe in a subject's microbiome upon the measuring; generating a report that provides information on the absence or quantity of at least one microbe in a subject's microbiome profile upon determining, and optionally providing information from a cohort that has been determined to have a similar microbiome profile as the subject-specific microbiome profile.

The methods, compositions, systems and kits described herein also provide quality control assay for a manufactured microbial-based therapeutic/cosmetic. For example, the methods, compositions, systems and kits described herein can be used to develop companion diagnostic test to determine if a manufactured microbial-based therapeutic/cosmetic has maintained its genetic integrity during the manufacturing or storage process.

II. Methods

A. Microbiome Profiling

The present disclosure provides for methods for measuring at least one microbe in biological sample from at least one microbiome from a subject and determining a microbiome profile. A microbiome profile can be assessed using any suitable detection means that can measure or quantify one or more microbes (bacteria, fungi, viruses and archaea) that comprise a microbiome.

In general, the present disclosure employs long read length sequencing processes and systems to measure the full 16S or the 23S ribosomal subunits, their intergenic regions and optionally other genetic elements with discriminative power in a particular microbe in order to identify informative microbiome profiles.

In some applications, the microbial profile of a subject is in part determine using additional clinical information such as the subject's age, weight, gender, medical history, risk factors, family history or any other clinically relevant information.

In some applications, a subject's microbiome profile can comprise a single microbiome. For example, a subject's microbiome profile can comprise of at least one biological sample from only the subject's intestinal microbiome. For example, a subject's microbiome profile can comprise of at least one biological sample from only the subject's stomach microbiome. For example, a subject's microbiome profile can comprise of at least one biological sample from only the subject's gut microbiome. For example, a subject's microbiome profile can comprise of at least one biological sample from only the subject's oral microbiome.

In some applications, a subject's microbiome profile can comprise of at least one biological sample from more than one microbiome. For example, a subject's microbiome profile can comprise of at least one biological sample from the subject's skin microbiome and umbilical microbiome. In another example, a subject's microbiome profile can comprise of at least one biological sample from the subject's intestinal microbiome, stomach microbiome, gut microbiome and oral microbiome. In another example, a subject's microbiome profile can comprise of at least one biological sample from the subject's intestinal microbiome and at least one biological sample from stomach microbiome. In another example, a subject's microbiome profile can comprise of at least one biological sample from the subject's gut microbiome and at least one biological sample from oral microbiome. In some applications, a subject's microbiome profile can comprise of at least 2, 3, 4, 5, 6, 7, 8, 9, 10, 11, 12, 13, 14, 15, 16, 17, 18, 19, 20 microbiomes.

In some applications, a subject's microbiome profile can comprise of one microbe. In some applications, a subject's microbiome profile can comprise of 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, 100 or fewer microbes, 200 or fewer microbes, 300 or fewer microbes, 400 or fewer microbe, 500 or fewer microbes, 600 or fewer microbes, 700 or fewer microbes, or 800 or fewer microbes.

In some applications the entire genome to the microbe will be analyzed to determine a subject's microbiome profile. In other applications, the variable regions of the microbe's genome will be analyzed to determine a subject's microbiome profile. For example genetic variation in the genome can include restriction fragment length polymorphisms, single nucleotide polymorphisms, insertions, deletions, indels (insertions-deletions), microsatellite repeats, minisatellite repeats, short tandem repeats, transposable elements, randomly amplified polymorphic DNA, amplification fragment length polymorphism or a combination thereof.

In some applications, the entire genomic region of the 16S or 23S ribosomal subunit to the microbe will be analyzed to determine a subject's microbiome profile. In some applications, the variable regions of the 16S or 23S ribosomal subunit to the microbe will be analyzed to determine a subject's microbiome profile.

The methods, compositions, systems provided herein can generate a cohort-generalized microbiome profile or a subject-specific microbiome profile. A cohort-generalized microbiome profile can be determined upon the measurement data from more than one subject's microbiome from a particular group. For example, a cohort, can be subjects from a particular age group, region of the world, ethnicity, religious group, sexual habits, hygiene habits, product use, dietary regimen, weight, gender, medical history, risk factors, family history, or combinations thereof A subject-specific microbiome profile can be determined from one or more microbiomes from a subject.

An exemplary method can comprise at least one of the following steps: obtaining a biological sample from a subject; measuring at least one microbe in the biological sample of the subject; detecting or measuring the presence or absence of at least one microbe upon measuring; and generating a report that provides details the presence, absence, or quantity of at least one microbe in a subject's microbiome.

An exemplary method can comprise at least one of the following steps: obtaining a biological sample from a subject; measuring a panel of microbes in the biological sample of the subject; detecting a presence or absence of the panel of microbes upon measuring; determining the subject's microbiome profile; and generating a report that provides details about the determined microbiome profile or a similar microbiome profile.

The present disclosure provides diagnostic assays for predicting a disease status of a subject or likelihood of a subject's response to a therapeutic. The diagnostic assay can use the presence of one or more microbes to calculate a quantitative score that can be used to predict disease status or likelihood of response to a therapeutic in a subject. In some applications, the diagnostic assay can use the presence of one or more microbes and one or more characteristics, such as, e.g., age, weight, gender, medical history, risk factors, family history, or a combination thereof to calculate a quantitative score that can be used to predict disease status or likelihood of response to a therapeutic in a subject.

In some applications, a decrease in one or more microbes' threshold values in a subject's microbiome profile indicates an increased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, a decrease in one or more microbes' threshold values in a subject's microbiome profile indicates a decreased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, an increase in one or more microbes' threshold values in a subject's microbiome profile indicates an increased likelihood of one or more of: a poor clinical outcome, good clinical outcome, high risk of disease, low risk of disease, complete response, partial response, stable disease, non-response, and recommended treatments for disease management. In some applications, a decrease in one or more microbes' threshold values indicates an increased likelihood of one or more of: a poor clinical outcome, good clinical outcome, high risk of disease, low risk of disease, complete response, partial response, stable disease, non-response, and recommended treatments for disease management.

In some applications, an increase in one or more microbes' threshold values in a subject's microbiome profile indicates a decreased likelihood of one or more of: a poor clinical outcome, good clinical outcome, high risk of disease, low risk of disease, complete response, partial response, stable disease, non-response, and recommended treatments for disease management. In some applications, a decrease in one or more microbes' threshold values indicates an increased likelihood of one or more of: a poor clinical outcome, good clinical outcome, high risk of disease, low risk of disease, complete response, partial response, stable disease, non-response, and recommended treatments for disease management.

In some applications, a similar microbiome profile to a reference profile indicates an increased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

In some applications, a similar microbiome profile to a reference profile indicates a decreased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

B. Samples

Biological samples can be collected from a subject who wants information on one or more of their microbiomes. Any sample type from any microbiome on the body of a subject can be used with the methods, systems, and kits of the present disclosure. Examples of microbiomes that can be used with the present disclosure include but are not limited to skin microbiome, umbilical microbiome, vaginal microbiome, conjunctival microbiome, intestinal microbiome, stomach microbiome, gut microbiome and oral microbiome, nasal microbiome, gastrointestinal tract microbiome, and urogenital tract microbiome.

Depending on the application the selection of a biological sample may be tailored to that specific application. In any of the methods provided herein the biological sample can be whole blood, serum, plasma, mucosa, saliva, cheek swab, urine, stool, cells, tissue, lymph fluid, CNS fluid, and lesion exudates or a combination thereof.

C. Sample Preparation

Biological samples used with the methods, composition, systems, and kits provide herein may be processed using any means known in the art or otherwise described herein in order to enable measurement of one or more microbes. Sample preparation can comprise any one of the following steps or combination of steps: 1) a sterile swab is first dipped into a tube containing sterile 1×PBS to wet. 2) The swab is swiped across the area of interest 10-20 times with enough vigor that the tissue is slightly pink/red colored afterwards. 3) The swab is gently dipped into 300 uL of lysis buffer (described herein) in a sterile 1.5 mL tube. 4) The swab is left in the microcentrifuge tube for shipping to a laboratory to be further analyzed as provided herein. The samples obtained can be shipped overnight at room temperature.

Shipping bacterial cells in buffers have inherent biases associated with them—some strains are able to continue propagating on the very few nutrients that come along with sample collection while other strains will undergo apoptosis in the absence of a very specific environment. As a result, samples shipped in this fashion often have an initial profiling/population bias associated with cellular integrity.

Current approaches strongly enrich for intact cells by first centrifuging the collected sample. The resulting pellet, formed from the intact cells within the sample, is then the precursor for all of the downstream steps. In contrast, the present methods provided herein includes a purification step to concentrate any DNA present in the supernatant (e.g. from already lysed cells). This DNA is then combined with the DNA extracted from the standard pellet preparation, and this combination now forms the more complete precursor to the downstream steps.

In the present methods provided herein, microbiome samples can be immediately put into the specific lysis buffer cocktail described below, rather than standard buffers are stable for 3 days at room temperature, allowing enough time for samples that need to be shipped. These samples can then be processed as usual and DNA will remain intact for use in long readlength sequencing and microbiome profiling. The Lysis buffer contains: 20 mM Tris, pH8.0, 20 mM EDTA, 1% SDS, 0.5% Tween, 1% Triton X-100, and 400ug/mL proteinase K.

The subsequent extraction of DNA from human microbiome samples includes several steps, each of which contribute to sample integrity and artifactual chimeric molecule production. For the amplicon approach these steps can include: PCR, sample quantification (e.g. Qubit, nanodrop, bioanalyzer, etc.), Blue Pippin size selection, 0.5× Ampure purification, sample quantification, DNA end repair, 0.5× Ampure purification, blunt end adaptor ligation, exo-nuclease treatment, two 0.5× Ampure purifications, and final Blue Pippen size selection. Depending on the sample one or more of these steps maybe removed to improve the fidelity of the microbiome profiling. This is determined empirically in a feed-back loop with the profiling, by using known mock communities as tests, or by introducing known quantities of non-commensal strains into the sample.

In some applications, the method does not use an amplification step. Examples of such methods include those methods that use sequencing by Whole Genome Shotgun (WGS) sequencing. These approaches can provide a benefit by removing amplification bias, which is known to skew microbial distributions. In addition, such approaches also allows for de novo discovery of pertinent elements, for example such as bacterial plasmids, fungi and viruses.

The practice of the methods of the present disclosure can employ conventional techniques of immunology, biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds.

(1995)), CULTURE OF ANIMAL CELLS: A MANUAL OF BASIC TECHNIQUE AND SPECIALIZED APPLICATIONS, 6th Edition (R. I. Freshney, ed. (2010), and Lange, et. al., Molecular Systems Biology Vol. 4:Article 222 (2008), which are hereby incorporated by reference. For example, preparation of a biological sample may comprise, e.g., extraction or isolation of intracellular material from a cell or tissue such as the extraction of nucleic acids, protein, or other macromolecules. Sample preparation which can be used with the methods of disclosure include but are not limited to, centrifugation, affinity chromatography, magnetic separation, immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, radioisotope assay, protein synthesis assay, histological assay, culture assay, and combinations thereof.

Accessing the nucleic acids and macromolecules from the intercellular space of the sample may generally be performed by either physical, chemical methods, or a combination of both.

The nucleic acids used with the methods described herein can be isolated from any biological samples using shearing methods which preserve the integrity and continuity of genomic DNA.

Nucleic acids sample that can be used with the present disclosure include all types of DNA and RNA. The length of nucleic acids can be about 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000, nucleotides or base pairs in length.

Variations found in the nucleic acids "variable regions" may provide a means for distinguishing genomes or strains. Examples of such variation in the nucleic acids include but are not limited to, polymorphisms such as: restriction fragment length polymorphisms, single nucleotide polymorphisms, insertions, deletions, indels (insertions-deletions), microsatellite repeats, minisatellite repeats, short tandem repeats, transposable elements, randomly amplified polymorphic DNA, and amplification fragment length polymorphism.

D. Detection

Profiling of a microbiome can be conducted by various means known in the art, some of which are provided herein. In some applications, microbiome profiling can comprise one or more detection means.

In some applications samples will be measured using sequencing methods. In certain application the PCR primers, provided herein, will contain unique barcode identifiers. In some applications the addition of the barcode identifiers allows for multiplexing of multiple samples (e.g. biological samples or microbiome samples) using the computers systems and executable-code provide herein. In applications where single molecule sequencing is used, computers systems and executable-code that can derive base modification detection for each sample, as provided herein, can be useful.

Examples sequencing technologies that can be used with the present methods, systems and kits of the disclosure for achieving long read lengths include but are not limited to the SMRT® sequencing systems from Pacific Biosciences. In particular, the SMRT systems produce average read lengths in excess of 5000 bases in length, based upon single molecule, real time observation of nucleic acid replication (See, e.g., U.S. Pat. Nos. 7,056,661, 7,056,676, 7,052,847 and 7,033,764, and Chin C S, et. al., Nonhybrid finished microbial genome assemblies from long read SMRT sequencing data. Nat Methods. 2013 June; 10(6): 563-9)

Other sequencing systems and approaches that can be used with the present disclosure include but are not limited to long read length Sanger sequencing, long read ensemble sequencing approaches, e.g., Illumina/Moleculo sequencing and potentially, other single molecule sequencing approaches, such as Nanopore sequencing technologies.

In applications where long read sequencing is used with the methods of the present disclosure, long read sequencing can include sequencing that provides a contiguous sequence read of longer than 500 bases, preferably, longer than 800 bases, more preferably, greater than 1000 bases, and in most preferred aspects, longer than 1500 bases. Long read sequencing can also include sequencing that provides a contiguous sequence read of longer than 1500 bases, preferably, longer than 2000 bases, more preferably, greater than 3000 bases, and longer than 4500 bases.

In particularly preferred aspects, single molecule, real time sequencing approaches are preferred, such as the Pacific Biosciences SMRT technology. In particular, by providing both extremely long read lengths and single molecule resolution, these systems provide advantages for classification accuracy as well as the potential for extremely high multiplex, e.g., with different individual molecules providing different opportunities to classify different constituents within a microbiome sample.

Because each single molecule read spans the entire 16S and/or 23S region, assembly is not required. Therefore, barcoding and multiplexing can be employed to reduce the cost per strain/sample.

Suitable barcodes that can be used with the invention include but are not limited to SEQ ID NOS 1-16 and SEQ ID NOS 660-742.

The present disclosure takes advantage of the long read length, single molecule sequencing system in order to classify microbial organisms in a mixed population. The resulting "microbiome profile" will take advantage of the outputs, which contain the entire 16S and 23S regions, to achieve unparalleled classification accuracy at a lower cost.

Additionally the present invention includes a non-amplification mode in which a whole genome shotgun (WGS) sample is used to profile the microbiome. This removes amplification bias from the profiling which is known to be problematic. Reads from any part of the meta-genome can thus be used as the strain identifier. This allows for de novo discovery of pertinent elements such as bacterial plasmids, fungi and viruses. This also expands the possible level of variation to be observed since the requirement of known constant regions is removed. By comparing the results of the amplicon approach with WGS, biases in the amplicon approach can be corrected and a sample efficient, amplicon version, can be created for specific applications. This also allows the usage of base modification signal since the sample preparation does not include an amplification step.

In addition to read length and multiplex benefits, single molecule real time sequencing is also useful for obtaining information on base modifications present in a given organism's genome. In particular, by using long read length technologies which are sensitive to base modifications, the disclosure can take advantage of this additional or $5^{th}$ base data to add classification specificity to sample analyses and classification. Because DNA modifications are known to affect gene expression, it is clear that microbes, such as bacteria with the same genome but different base modifications should be considered different strains with distinct activities/host interactions.

In addition to applying the read length and multiplex advantages towards improving phylogenetic classification using 16S, 23S, or other genomic locations, these advantages can also be used towards a fuller delineation of the true expression profile of the microbiome. Thus, full length transcript sequencing will yield a more complete picture of what metabolic pathways are most relevant for improving host health.

Microbiome profiling can comprise usage of a nucleic acid microarray. The microbiome can be measured in either fresh or fixed sample using microarray technology. In this method, polynucleotide sequences of interest (including cDNAs, RNA, mRNA, ect. and oligonucleotides) can be plated, or arrayed, on a microchip substrate. The arrayed sequences can be then hybridized with specific probes with complementarity to the oligonucleotides on the substrate. The arrayed sequences can also be PCR amplified inserts of nucleic acid clones can be applied to a substrate in a dense array.

In some applications, there can be greater than 100, 500, 1,000, 2000, 3,000 4,000, 5,000, 6,000, 7,000, 8,000, 9,000 or 10,000 nucleotide sequences can be applied to the substrate. The microarrayed genes, variable regions, intergenic regions or other regions of interest are immobilized on the microchip at greater than 100, 500, 1,000, 2000, 3,000 4,000, 5,000, 6,000, 7,000, 8,000, 9,000 or 10,000 elements each, can be suitable for hybridization under stringent conditions.

Fluorescently labeled probes may be generated through incorporation of fluorescent nucleotides. Labeled probes can then be applied to the chip hybridize with specificity to each spot of the array. After stringent washing to remove non-specifically bound probes, the microarray chip can be scanned by a device such as, confocal laser microscopy or by another detection method, such as a CCD camera. Quantitation of hybridization of each arrayed element allows for assessment of corresponding abundance. With dual color fluorescence, separately labeled probes generated from more than one source of nucleic acids can be hybridized to the array. The relative abundance of the nucleic acids sources corresponding to each specified gene can be thus determined. Analysis of the microarray readout can be performed by commercially available equipment.

Microbiome profiling can further comprise of use of a biochip. Biochips can be used to screen a large number of macromolecules. Biochips can be designed with immobilized nucleic acid molecules, full-length proteins, antibodies, affibodies (small molecules engineered to mimic monoclonal antibodies), aptamers (nucleic acid-based ligands) or chemical compounds. A chip could be designed to detect multiple macromolecule types on one chip. For example, a chip could be designed to detect nucleic acid molecules, proteins and metabolites on one chip. The biochip can be used to and designed to simultaneously analyze a panel microbes in a single sample.

In some applications, microbiome profiling can comprise use of a protein microarray. Protein microarray can be a particular type of biochip which can be used with the present disclosure. The chip can comprise a support surface such as a glass slide, nitrocellulose membrane, bead, or microtitre plate, to which an array of capture proteins can be bound in an arrayed format onto a solid surface. Protein array detection methods can give a high signal and a low background. Detection probe molecules, typically labeled with a fluorescent dye, can be added to the array. Any reaction between the probe and the immobilized protein can result in emission of a detectable signal. Such protein microarrays can be rapid, automated, and offer high sensitivity of protein markers known to be located on a microbe read-outs for diagnostic tests.

In some applications, microbiome profiling can comprise use of an analytical protein microarrays can be constructed using a library of antibodies, aptamers or affibodies. The array can be probed with a complex protein solution from a biological sample that function by capturing protein molecules they specifically bind to. Analysis of the resulting binding reactions using various detection systems can provide information about expression levels of particular proteins in the sample as well as measurements of binding affinities and specificities. This type of protein microarray can be especially useful in comparing protein expression in different samples. Functional protein microarrays can be constructed by immobilizing large numbers of purified full-length functional proteins or protein domains and can be used to identify protein-protein, protein-DNA, protein-RNA, protein-phospholipid, and protein-small molecule interactions, to assay enzymatic activity and to detect antibodies and demonstrate their specificity. These protein microarray biochips can be used to study the biochemical activities of the entire proteome in a sample.

In some applications, microbiome profiling can comprise use of reverse phase protein microarray (RPA). Reverse phase protein microarray can be constructed from tissue and cell lysates that can be arrayed onto the microarray and probed with antibodies against the target protein of interest. These antibodies can be detected with chemiluminescent, fluorescent or colorimetric assays. In addition to the protein in the lysate, reference control peptides can be printed on the slides to allow for protein quantification.

In some applications, microbiome profiling can further comprise use of a digital PCR device or droplet digital PCR device. Droplet digital PCR can be used to partition molecules such as DNA, RNA or protein in a biological sample to a compartment and identifying and measure molecules in that compartment. Interrogation of each droplet can yield counts and measurements of molecules present in the biological sample.

E. Primers and Probes

The analysis of the 16S ribosomal RNA gene is one approach that can be used to understand microbial diversity. Another approach that can be applied is the analysis of the 23S ribosomal RNA gene. The accuracy of these analyses depends strongly on the choice of primers.

Primers can be prepared by a variety of methods including, but not limited to, cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. In addition, computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering.

Primers that can be used analyze the 16S ribosomal RNA gene include but are not limited to SEQ ID NOS 17-24.

Primers that can be used analyze the 16S ribosomal RNA gene include but are not limited to SEQ ID NOS 17-24 and 646-656.

Primers that can be used analyze the 23S ribosomal RNA gene include but are not limited to SEQ ID NOS 25-67 and 657-659.

Microbial diversity can be further described by approaches analyzing the intergenic region between 16S ribosomal RNA and 23S ribosomal RNA. Primers that can be used to analyze the intergenic region between 16S ribosomal RNA and 23S ribosomal RNA include but are not limited to SEQ ID NOS 270-364 (forward intergenic primers) and 551-645 (reverse intergenic primers).

Primers that can be designed to specifically amplify and identified variable regions in the 16S ribosomal RNA and 23S ribosomal RNA include but are not limited to SEQ ID NOS 87-180 (forward 16S primers), 181-269 (forward 23S primers), 365-461 (reverse 16S primers) and 462-550 (reverse 23S primers). Primers can be designed to specifically amplify any identified variable regions in a microbe or similar distinguishing genetic element.

Primers or probes described herein can also include polynucleotides having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% homology to any of the nucleic acid sequences described herein.

Primers or probes described herein can also include polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% homology to any of the nucleic acid sequences described herein.

In some applications, it may be useful to incorporate restriction sites into primer or probe sequence depending on the particular application. Examples of restriction enzymes that can be used with the methods of the present disclosure include but are not limited to: AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaqαI, TfiI, TliI, TseI, Tsp45I, Tsp509I, TspMI, TspRI, Tth111I, XbaI, XcmI, XhoI, XmaI, XmnI, and ZraI.

In some applications, it may be useful to incorporate a barcode into primer or probe sequence depending on the particular application. Examples of barcodes that can be used with the invention are provided herein. Barcoding of the biological sample can be used to facilitate multiplexing assays as provided herein. Barcoding of the biological sample can be used in methods described herein that use sequencing as the detection means.

F. Algorithm-Based Methods

The present disclosure provides for machine learning algorithms for building a diagnostic microbiome profile of a subject. Depending on the application a diagnostic microbiome profile can a generate score from a microbiome profile, can be a comparison to a reference microbiome profile, can be the level of a microbiome profile above a defined threshold or a combination thereof.

The present disclosure includes sequencing methods that utilize higher error rate, single molecule platforms. These systems are asynchronous in nature, thus providing the long readlengths necessary to properly classify the complex strains that make up the microbiome.

In the case of amplicon sequencing (16S, 23S, and other marker genes) the raw data produced from this platform is first filtered for proper primer orientation, pairing, and completeness. The resulting molecules are then filtered based on quality (with quality thresholds of greater than 0.95, 0.99, 0.999, etc. being possible). These molecules then form the basis set of reads to be used to establish the de novo clusters, and can directly be compared to the known reference databases. Molecules that only partially match to the known reference database are appended to a novel hit database. Stringent read length thresholds of >1,000 bases prevent spurious reads from mistakenly making it into the novel hit database. An empirically (using mock community or non-commensal introduced strain) determined error weighting is used in the clustering to minimize the effect of platform specific sequencing artifacts affecting the clustering.

In the case of WGS, empirically determined (using mock community or non-commensal introduced strain) cutoff read lengths and accuracies are used and those are matched to a maximum sensitivity threshold. The resulting molecules are then filtered based on quality (with quality thresholds of greater than 0.95, 0.99, 0.999, etc. being possible). These molecules then form the basis set of reads to be used to establish the de novo clusters, and can directly be compared to the known reference databases. Molecules that only partially match to the known reference database are appended to a novel hit database. Stringent read length thresholds of >1,000 bases prevent spurious reads from mistakenly making it into the novel hit database. An empirically (using mock community or non-commensal introduced strain) determined error weighting is used in the clustering to minimize the effect of platform specific sequencing artifacts affecting the clustering.

Examples of machine learning algorithms that can be used include, but are not limited to: elastic networks, random forests, support vector machines, and logistic regression. The algorithms provided herein can aid in selection of important microbes and transform the underlying measurements into a score or probability relating to, for example, disease risk, disease likelihood, presence or absence of disease, treatment response, and/or classification of disease status.

Any of the methods, kits, and systems described herein can utilize a diagnostic assay for predicting a disease status of a subject or likelihood of a subject's response to a therapeutic. The diagnostic assay can use the presence of one or more microbes to calculate a quantitative score that can be used to predict disease status or likelihood of response to a therapeutic in a subject. The diagnostic assay can use the presence of one or more microbes and one or more characteristics, such as, e.g., age, weight, gender, medical history, risk factors, family history to calculate a quantitative score that can be used to predict disease status or likelihood of response to a therapeutic in a subject.

In some applications, an increase in a score in the diagnostic assay indicates an increased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, a decrease in a score in the diagnostic assay indicates an increased likelihood of one or more of: a poor clinical outcome, good clinical outcome, high risk of disease, low risk of disease, complete response, partial response, stable disease, non-response, and recommended treatments for disease management. In some embodiments, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

In some applications, a similar microbiome profile to a reference profile in the diagnostic assay indicates an increased likelihood of one or more of: a poor clinical outcome, good clinical outcome, high risk of disease, low risk of disease, complete response, partial response, stable disease, non-response, and recommended treatments for disease management. In some applications, a dissimilar microbiome profile to a reference profile indicates one or more of: an increased likelihood of a poor clinical outcome, good clinical outcome, high risk of disease, low risk of disease, complete response, partial response, stable disease, non-response, and recommended treatments for disease management.

In some applications, an increase in one or more microbes' threshold values in the diagnostic assay indicates an increased likelihood of one or more of: a poor clinical outcome, good clinical outcome, high risk of disease, low risk of disease, complete response, partial response, stable disease, non-response, and recommended treatments for disease management. In some applications, a decrease in one or more microbes threshold values indicates an increased likelihood of one or more of: a poor clinical outcome, good clinical outcome, high risk of disease, low risk of disease, complete response, partial response, stable disease, non-response, and recommended treatments for disease management.

In some applications, a decrease in one or more microbes' threshold values in the diagnostic assay indicates an increased likelihood of one or more of: a poor clinical outcome, good clinical outcome, high risk of disease, low risk of disease, complete response, partial response, stable disease, non-response, and recommended treatments for disease management. In some applications, a decrease in one or more microbes threshold values indicates an increased likelihood of one or more of: a poor clinical outcome, good clinical outcome, high risk of disease, low risk of disease, complete response, partial response, stable disease, non-response, and recommended treatments for disease management.

The present disclosure provides methods of treatments. Provided herein are methods for generalized-treatment recommendations for a subject based on their microbiome profiling and methods for subject-speific treatment recommendation. Methods for treatments can comprise one of the following steps: determining a first ratio of a level of a subject-specific microbiome profile to a level of a second microbiome profile in a biological sample obtained from at least one subject; detecting a presence or absence of a disease in the subject based upon the determining; and recommending to the subject at least one generalized or subject-specific treatment to ameliorate disease symptoms.

Any diagnostic microbiome profile, a subject-specific microbiome profile, or a therapeutic/cosmetic described herein can include one or more, but are not limited to the following microbes: Abiotrophia, Abiotrophia defectiva, Abiotrophia, Acetanaerobacterium, Acetanaerobacterium elongatum, Acetanaerobacterium, Acetivibrio, Acetivibrio bacterium, Acetivibrio, Acetobacterium, Acetobacterium, Acetobacterium woodii, Acholeplasma, Acholeplasma, Acidaminococcus, Acidaminococcus fermentans, Acidaminococcus, Acidianus, Acidianus brierleyi, Acidianus, Acidovorax, Acidovorax, Acinetobacter, Acinetobacter guiltouiae, Acinetobacter junii, Acinetobacter, Actinobacillus, Actinobacillus M1933/96/1, Actinomyces, Actinomyces ICM34, Actinomyces ICM41, Actinomyces ICM54, Actinomyces lingnae, Actinomyces odontolyticus, Actinomyces oral, Actinomyces ph3, Actinomyces, Adlercreutzia, Adlercreutzia equolifaciens, Adlercreutzia intestinal, Adlercreutzia, Aerococcus, Aerococcus, Aeromonas, Aeromonas 165C, Aeromonas hydrophila, Aeromonas RC50, Aeromonas, Aeropyrum, Aeropyrum pernix, Aeropyrum, Aggregatibacter, Aggregatibacter, Agreia, Agreia bicolorata, Agreia, Agromonas, Agromonas CS30, Akkermansia, Akkermansia muciniphila, Akkermansia, Alistipes, Alistipes ANH, Alistipes AP11, Alistipes bacterium, Alistipes CCUG, Alistipes DJF_B185, Alistipes DSM, Alistipes EBA6-25c12, Alistipes finegoldii, Alistipes indistinctus, Alistipes JC136, Alistipes NML05A004, Alistipes onderdonkii, Alistipes putredinis, Alistipes RMA, Alistipes senegalensis, Alistipes shahii, Alistipes Smarlab, Alistipes, Alkalibaculum, Alkalibaculum, Alkaliflexus, Alkaliflexus, Allisonella, Allisonella histaminiformans, Allisonella, Alloscardovia, Alloscardovia omnicolens, Anaerofilum, Anaerofilum, Anaerofustis, Anaerofustis stercorihominis, Anaerofustis, Anaeroplasma, Anaeroplasma, Anaerostipes, Anaerostipes 08964, Anaerostipes 1y-2, Anaerostipes 494a, Anaerostipes 5_1_63FAA, Anaerostipes AIP, Anaerostipes bacterium, Anaerostipes butyraticus, Anaerostipes caccae, Anaerostipes hadrum, Anaerostipes IE4, Anaerostipes indolis, Anaerostipes, Anaerotruncus, Anaerotruncus colihominis, Anaerotruncus NML, Anaerotruncus, Aquincola, Aquincola, Arcobacter, Arcobacter, Arthrobacter, Arthrobacter FV1-1, Asaccharobacter, Asaccharobacter celatus, Asaccharobacter, Asteroleplasma, Asteroleplasma, Atopobacter, Atopobacter phocae, Atopobium, Atopobium parvulum, Atopobium rimae, Atopobium, Bacteriovorax, Bacteriovorax, Bacteroides, Bacteroides 31SF18, Bacteroides 326-8, Bacteroides 35AE31, Bacteroides 35AE37, Bacteroides 35BE34, Bacteroides 4072, Bacteroides 7853, Bacteroides acidifaciens, Bacteroides AP1, Bacteroides AR20, Bacteroides AR29, Bacteroides B2, Bacteroides bacterium, Bacteroides barnesiae, Bacteroides BLBE-6, Bacteroides BV-1, Bacteroides caccae, Bacteroides CannelCatfish9, Bacteroides cellulosilyticus, Bacteroides chinchillae, Bacteroides CIP103040, Bacteroides clarus, Bacteroides coprocola, Bacteroides coprophilus, Bacteroides D8, Bacteroides DJF_B097, Bacteroides dnLKV2, Bacteroides dnLKV7, Bacteroides dnLKV9, Bacteroides dorei, Bacteroides EBAS-17, Bacteroides eggerthii, Bacteroides enrichment, Bacteroides F-4, Bacteroides faecichinchillae, Bacteroides faecis, Bacteroides fecal, Bacteroides finegoldii, Bacteroides fragilis, Bacteroides gallinarum, Bacteroides helcogenes, Bacteroides ic1292, Bacteroides intestinalis, Bacteroides massiliensis, Bacteroides mpnisolate, Bacteroides NB-8, Bacteroides new, Bacteroides nlaezlc13, Bacteroides nlaezlc158, Bacteroides nlaezlc159, Bacteroides nlaezlc161, Bacteroides nlaezlc163, Bacteroides nlaezlc167, Bacteroides nlaezlc172, Bacteroides nlaezlc18, Bacteroides nlaezlc182, Bacteroides nlaezlc190, Bacteroides nlaezlc198, Bacteroides nlaezlc204, Bacteroides nlaezlc205, Bacteroides nlaezlc206, Bacteroides nlaezlc207, Bacteroides nlaezlc211, Bacteroides nlaezlc218, Bacteroides nlaezlc257, Bacteroides nlaezlc260, Bacteroides nlaezlc261, Bacteroides nlaezlc263, Bacteroides nlaezlc308, Bacteroides nlaezlc315, Bacteroides nlaezlc322, Bacteroides nlaezlc324, Bacteroides nlaezlc331, Bacteroides nlaezlc339, Bacteroides nlaezlc36, Bacteroides nlaezlc367, Bacteroides nlaezlc375, Bacteroides nlaezlc376, Bacteroides nlaezlc380, Bacteroides nlaezlc391, Bacteroides nlaezlc459, Bacteroides nlaezlc484, Bacteroides nlaezlc501, Bacteroides nlaezlc504, Bacteroides nlaezlc515, Bacteroides nlaezlc519, Bacteroides nlaezlc532, Bacteroides nlaezlc557, Bacteroides nlaezlc57, Bacteroides nlaezlc574, Bacteroides nlaezlc592, Bacteroides nlaezlg105, Bacteroides nlaezlg117, Bacteroides nlaezlg127, Bacteroides nlaezlg136, Bacteroides nlaezlg143, Bacteroides nlaezlg157, Bacteroides nlaezlg167, Bacteroides nlaezlg171, Bacteroides nlaezlg187, Bacteroides nlaezlg194, Bacteroides nlaezlg195, Bacteroides nlaezlg199, Bacteroides nlaezlg209, Bacteroides nlaezlg212, Bacteroides nlaezlg213, Bacteroides nlaezlg218, Bacteroides nlaezlg221, Bacteroides nlaezlg228, Bacteroides nlaezlg234, Bacteroides nlaezlg237, Bacteroides nlaezlg24, Bacteroides nlaezlg245, Bacteroides nlaezlg257, Bacteroides nlaezlg27, Bacteroides nlaezlg285, Bacteroides nlaezlg288, Bacteroides nlaezlg295, Bacteroides nlaezlg296, Bacteroides nlaezlg303, Bacteroides nlaezlg310, Bacteroides nlaezlg312, Bacteroides nlaezlg327, Bacteroides nlaezlg329, Bacteroides nlaezlg336, Bacteroides nlaezlg338, Bacteroides nlaezlg347, Bacteroides nlaezlg356, Bacteroides nlaezlg373, Bacteroides nlaezlg376, Bacteroides nlaezlg380, Bacteroides nlaezlg382, Bacteroides nlaezlg385, Bacteroides nlaezlg4, Bacteroides nlaezlg422, Bacteroides nlaezlg437, Bacteroides nlaezlg454, Bacteroides nlaezlg455, Bacteroides nlaezlg456, Bacteroides nlaezlg458, Bacteroides nlaezlg459, Bacteroides nlaezlg46, Bacteroides nlaezlg461, Bacteroides nlaezlg475, Bacteroides nlaezlg481, Bacteroides nlaezlg484, Bacteroides nlaezlg5, Bacteroides nlaezlg502, Bacteroides nlaezlg515, Bacteroides nlaezlg518, Bacteroides nlaezlg521, Bacteroides nlaezlg54, Bacteroides nlaezlg6, Bacteroides nlaezlg8, Bacteroides nlaezlg80, Bacteroides nlaezlg98, Bacteroides nlaezlh120, Bacteroides nlaezlh15, Bacteroides nlaezlh162, Bacteroides nlaezlh17, Bacteroides nlaezlh174, Bacteroides nlaezlh18, Bacteroides nlaezlh188, Bacteroides nlaezlh192, Bacteroides nlaezlh194, Bacteroides nlaezlh195, Bacteroides nlaezlh207, Bacteroides nlaezlh22, Bacteroides nlaezlh250, Bacteroides nlaezlh251, Bacteroides nlaezlh28, Bacteroides nlaezlh313, Bacteroides nlaezlh319, Bacteroides nlaezlh321, Bacteroides nlaezlh328, Bacteroides nlaezlh334, Bacteroides nlaezlh390, Bacteroides nlaezlh391, Bacteroides nlaezlh414, Bacteroides nlaezlh416, Bacteroides nlaezlh419, Bacteroides nlaezlh429, Bacteroides nlaezlh439, Bacteroides nlaezlh444, Bacteroides nlaezlh45, Bacteroides nlaezlh46, Bacteroides nlaezlh462, Bacteroides nlaezlh463, Bacteroides nlaezlh465, Bacteroides nlaezlh468, Bacteroides nlaezlh471, Bacteroides nlaezlh472, Bacteroides nlaezlh474, Bacteroides nlaezlh479, Bacteroides nlaezlh482, Bacteroides nlaezlh49, Bacteroides nlaezlh493, Bacteroides nlaezlh496, Bacteroides nlaezlh497, Bacteroides nlaezlh499, Bacteroides nlaezlh50, Bacteroides nlaezlh531, Bacteroides nlaezlh535, Bacteroides nlaezlh8, Bacteroides nlaezlp104, Bacteroides nlaezlp105, Bacteroides nlaezlp108, Bacteroides nlaezlp132, Bacteroides nlaezlp133, Bacteroides nlaezlp151, Bacteroides nlaezlp157, Bacteroides nlaezlp166, Bacteroides nlaezlp167, Bacteroides nlaezlp171, Bacteroides nlaezlp178, Bacteroides nlaezlp187, Bacteroides nlaezlp191, Bacteroides nlaezlp196, Bacteroides nlaezlp208, Bacteroides nlaezlp213, Bacteroides nlaezlp228, Bacteroides nlaezlp233, Bacteroides nlaezlp267, Bacteroides nlaezlp278, Bacteroides nlaezlp282, Bacteroides nlaezlp286, Bacteroides nlaezlp295, Bacteroides nlaezlp299, Bacteroides nlaezlp301, Bacteroides nlaezlp302, Bacteroides nlaezlp304, Bacteroides nlaezlp317, Bacteroides nlaezlp319, Bacteroides nlaezlp32, Bacteroides nlaezlp332, Bacteroides nlaezlp349, Bacteroides nlaezlp35, Bacteroides nlaezlp356, Bacteroides nlaezlp370, Bacteroides nlaezlp371, Bacteroides nlaezlp376, Bacteroides nlaezlp395, Bacteroides nlaezlp402, Bacteroides nlaezlp403, Bacteroides nlaezlp409, Bacteroides nlaezlp412, Bacteroides nlaezlp436, Bacteroides nlaezlp438, Bacteroides nlaezlp440, Bacteroides nlaezlp447, Bacteroides nlaezlp448, Bacteroides nlaezlp451, Bacteroides nlaezlp476, Bacteroides nlaezlp478, Bacteroides nlaezlp483, Bacteroides nlaezlp489, Bacteroides nlaezlp493, Bacteroides nlaezlp557, Bacteroides nlaezlp559, Bacteroides nlaezlp564, Bacteroides nlaezlp565, Bacteroides nlaezlp572, Bacteroides nlaezlp573, Bacteroides nlaezlp576, Bacteroides nlaezlp591, Bacteroides nlaezlp592, Bacteroides nlaezlp631, Bacteroides nlaezlp633, Bacteroides nlaezlp696, Bacteroides nlaezlp7, Bacteroides nlaezlp720, Bacteroides nlaezlp730, Bacteroides nlaezlp736, Bacteroides nlaezlp737, Bacteroides nlaezlp754, Bacteroides nlaezlp759, Bacteroides nlaezlp774, Bacteroides nlaezlp828, Bacteroides nlaezlp854, Bacteroides nlaezlp860, Bacteroides nlaezlp886, Bacteroides nlaezlp887, Bacteroides nlaezlp900, Bacteroides nlaezlp909, Bacteroides nlaezlp913, Bacteroides nlaezlp916, Bacteroides nlaezlp920, Bacteroides nlaezlp96, Bacteroides nordii, Bacteroides oleiciplenus, Bacteroides ovatus, Bacteroides paurosaccharolyticus, Bacteroides plebeius, Bacteroides R6, Bacteroides rodentium, Bacteroides S-17, Bacteroides S-18, Bacteroides salyersiae, Bacteroides SLC1-38, Bacteroides Smarlab, Bacteroides 'Smarlab, Bacteroides stercorirosoris, Bacteroides stercoris, Bacteroides str, Bacteroides thetaiotaomicron, Bacteroides TP-5, Bacteroides, Bacteroides uniformis, Bacteroides vulgatus, Bacteroides WA1, Bacteroides WH2, Bacteroides WH302, Bacteroides WH305, Bacteroides XB12B, Bacteroides XB44A, Bacteroides XO77B42, Bacteroides xylanisolvens, Barnesiella, Barnesiella intestinihominis, Barnesiella NSB1, Barnesiella, Barnesiella viscericola, Bavariicoccus, Bavariicoccus, Bdellovibrio, Bdellovibrio oral, Bergeriella, Bergeriella, Bifidobacterium, Bifidobacterium 103, Bifidobacterium 108, Bifidobacterium 113, Bifidobacterium 120, Bifidobacterium 138, Bifidobacterium 33, Bifidobacterium Acbbto5, Bifidobacterium adolescentis, Bifidobacterium Amsbbt12, Bifidobacterium angulatum, Bifidobacterium animalis, Bifidobacterium bacterium, Bifidobacterium bifidum, Bifidobacterium Bisn6, Bifidobacterium Bma6, Bifidobacterium breve, Bifidobacterium catenulatum, Bifidobacterium choerinum, Bifidobacterium coryneforme, Bifidobacterium dentium, Bifidobacterium DJF_WC44, Bifidobacterium F-10, Bifidobacterium F-11, Bifidobacterium group, Bifidobacterium h12, Bifidobacterium HMLN1, Bifidobacterium HMLN12, Bifidobacterium HMLN5, Bifidobacterium iarfr2341d, Bifidobacterium iarfr642d48, Bifidobacterium ic1332, Bifidobacterium indicum, Bifidobacterium kashiwanohense, Bifidobacterium LISLUCIII-2, Bifidobacterium longum, Bifidobacterium M45, Bifidobacterium merycicum, Bifidobacterium minimum, Bifidobacterium MSX5B, Bifidobacterium oral, Bifidobacterium PG12A, Bifidobacterium PL1, Bifidobacterium pseudocatenulatum, Bifidobacterium pseudolongum, Bifidobacterium pullorum, Bifidobacterium ruminantium, Bifidobacterium S-10, Bifidobacterium saeculare, Bifidobacterium saguini, Bifidobacterium scardovii, Bifidobacterium simiae, Bifidobacterium SLPYG-1, Bifidobacterium stellenboschense, Bifidobacterium stercoris, Bifidobacterium TM-7, Bifidobacterium Trm9, Bifidobacterium, Bilophila, Bilophila nlaezlh528, Bilophila, Bilophila wadsworthia, Blautia, Blautia bacterium, Blautia CE2, Blautia CE6, Blautia coccoides, Blautia DJF_VR52, Blautia DJF_VR67, Blautia DJF_VR70k1, Blautia formate, Blautia glucerasea, Blautia hansenii, Blautia ic1272, Blautia IE5, Blautia K-1, Blautia luti, Blautia M-1, Blautia mpnisolate, Blautia nlaezlc25, Blautia nlaezlc259, Blautia nlaezlc51, Blautia nlaezlc520, Blautia nlaezlc542, Blautia nlaezlc544, Blautia nlaezlh27, Blautia nlaezlh316, Blautia nlaezlh317, Blautia obeum, Blautia producta, Blautia productus, Blautia schinkii, Blautia Ser5, Blautia Ser8, Blautia, Blautia WAL, Blautia wexlerae, Blautia YHC-4, Brenneria, Brenneria, Brevibacterium, Brevibacterium, Brochothrix, Brochothrix thermosphacta, Buttiauxella, Buttiauxella 57916, Buttiauxella gaviniae, Butyricicoccus, Butyricicoccus bacterium, Butyricicoccus, Butyricimonas, Butyricimonas 180-3, Butyricimonas 214-4, Butyricimonas bacterium, Butyricimonas GD2, Butyricimonas synergistica, Butyricimonas, Butyricimonas virosa, Butyrivibrio, Butyrivibrio fibrisolvens, Butyrivibrio hungatei, Butyrivibrio, Caldimicrobium, Caldimicrobium, Caldisericum, Caldisericum, Campylobacter, Campylobacter coli, Campylobacter hominis, Campylobacter, Capnocytophaga, Capnocytophaga, Carnobacterium, Carnobacterium alterfunditum, Carnobacterium, Caryophanon, Caryophanon, Catenibacterium, Catenibacterium mitsuokai, Catenibacterium, Catonella, Catonella, Caulobacter, Caulobacter, Cellulophaga, Cellulophaga, Cellulosilyticum, Cellulosilyticum, Cetobacterium, Cetobacterium, Chelatococcus, Chelatococcus, Chlorobium, Chlorobium, Chryseobacterium, Chryseobacterium A1005, Chryseobacterium KJ9C8, Chryseobacterium, Citrobacter, Citrobacter 1, Citrobacter agglomerans, Citrobacter amalonaticus, Citrobacter ascorbata, Citrobacter bacterium, Citrobacter BinzhouCLT, Citrobacter braakii, Citrobacter enrichment, Citrobacter F24, Citrobacter F96, Citrobacter farmeri, Citrobacter freundii, Citrobacter gillenii, Citrobacter HBKC_SR1, Citrobacter HD4.9, Citrobacter hormaechei, Citrobacter 191-3, Citrobacter ka55, Citrobacter lapagei, Citrobacter LAR-1, Citrobacter ludwigii, Citrobacter MEB5, Citrobacter MS36, Citrobacter murliniae, Citrobacter nlaezlc269, Citrobacter P014, Citrobacter P042bN, Citrobacter P046a, Citrobacter P073, Citrobacter SR3, Citrobacter T1, Citrobacter tnt4, Citrobacter tnt5, Citrobacter trout, Citrobacter TSA-1, Citrobacter, Citrobacter werkmanii, Cloacibacillus, Cloacibacillus adv66, Cloacibacillus nlaezlp702, Cloacibacillus NML05A017, Cloacibacillus, Cloacibacterium, Cloacibacterium, Collinsella, Collinsella A-1, Collinsella aerofaciens, Collinsella AUH-Julong21, Collinsella bacterium, Collinsella CCUG, Collinsella, Comamonas, Comamonas straminea, Comamonas testosteroni, Conexibacter, Conexibacter, Coprobacillus, Coprobacillus bacterium, Coprobacillus cateniformis, Coprobacillus TM-40, Coprobacillus, Coprococcus, Coprococcus 14505, Coprococcus bacterium, Coprococcus catus, Coprococcus comes, Coprococcus eutactus, Coprococcus nexile, Coprococcus, Coraliomargarita, Coraliomargarita fucoidanolyticus, Coraliomargarita marisflavi, Coraliomargarita, Corynebacterium, Corynebacterium amycolatum, Corynebacterium durum, Coxiella, Coxiella, Cronobacter, Cronobacter dublinensis, Cronobacter sakazakii, Cronobacter turicensis, Cryptobacterium, Cryptobacterium curtum, Cupriavidus, Cupriavidus eutropha, Dechloromonas, Dechloromonas HZ, Desulfobacterium, Desulfobacterium, Desulfobulbus, Desulfobulbus, Desulfopila, Desulfopila La4.1, Desulfovibrio, Desulfovibrio D4, Desulfovibrio desulfuricans, Desulfovibrio DSM12803, Desulfovibrio enrichment, Desulfovibrio fairfieldensis, Desulfovibrio LNB1, Desulfovibrio piger, Desulfovibrio, Dialister, Dialister E2_20, Dialister GBA27, Dialister invisus, Dialister oral, Dialister succinatiphilus, Dialister, Dorea, Dorea auhjulong64, Dorea bacterium, Dorea formicigenerans, Dorea longicatena, Dorea mpnisolate, Dorea, Dysgonomonas, Dysgonomonas gadei, Dysgonomonas, Edwardsiella, Edwardsiella tarda, Eggerthella, Eggerthella E1, Eggerthella lenta, Eggerthella MLG043, Eggerthella MVAl, Eggerthella S6-C1, Eggerthella SDG-2, Eggerthella sinensis, Eggerthella str, Eggerthella, Enhydrobacter, Enhydrobacter, Enterobacter, Enterobacter 1050, Enterobacter 1122, Enterobacter 77000, Enterobacter 82353, Enterobacter 9C, Enterobacter A5C, Enterobacter adecarboxylata, Enterobacter aerogenes, Enterobacter agglomerans, Enterobacter AJAR-A2, Enterobacter amnigenus, Enterobacter asburiae, Enterobacter B1(2012), Enterobacter B363, Enterobacter B509, Enterobacter bacterium, Enterobacter Badong3, Enterobacter BEC441, Enterobacter C8, Enterobacter cancerogenus, Enterobacter cloacae, Enterobacter CO, Enterobacter core2, Enterobacter cowanii, Enterobacter dc6, Enterobacter DRSBII, Enterobacter enrichment, Enterobacter FL13-2-1, Enterobacter GIST-NKst10, Enterobacter GIST-NKst9, Enterobacter GJ1-11, Enterobacter gx-148, Enterobacter hormaechei, Enterobacter I-Bh20-21, Enterobacter ICB113, Enterobacter kobei, Enterobacter KW14, Enterobacter 112, Enterobacter ludwigii, Enterobacter M10_1B, Enterobacter M1R3, Enterobacter marine, Enterobacter NCCP-167, Enterobacter of, Enterobacter oryzae, Enterobacter oxytoca, Enterobacter P101, Enterobacter S11, Enterobacter SEL2, Enterobacter SPh, Enterobacter SSASP5, Enterobacter terrigena, Enterobacter TNT3, Enterobacter TP2MC, Enterobacter TS4, Enterobacter TSSAS2-48, Enterobacter, Enterobacter ZYXCA1, Enterococcus, Enterococcus 020824/02-A, Enterococcus 1275b, Enterococcus 16C, Enterococcus 48, Enterococcus 6114, Enterococcus ABRIINW-H61, Enterococcus asini, Enterococcus avium, Enterococcus azikeevi, Enterococcus bacterium, Enterococcus BBDP57, Enterococcus BPH34, Enterococcus Bt, Enterococcus canis, Enterococcus casseliflavus, Enterococcus CmNA2, Enterococcus Da-20, Enterococcus devriesei, Enterococcus dispar, Enterococcus DJF_O30, Enterococcus DMB4, Enterococcus durans, Enterococcus enrichment, Enterococcus F81, Enterococcus faecalis, Enterococcus faecium, Enterococcus fcc9, Enterococcus fecal, Enterococcus flavescens, Enterococcus fluvialis, Enterococcus FR-3, Enterococcus FUA3374, Enterococcus gallinarum, Enterococcus GHAPRB1, Enterococcus GSC-2, Enterococcus GYPB01, Enterococcus hermanniensis, Enterococcus hirae, Enterococcus lactis, Enterococcus malodoratus, Enterococcus manure, Enterococcus marine, Enterococcus MNC1, Enterococcus moraviensis, Enterococcus MS2, Enterococcus mundtii, Enterococcus NAB15, Enterococcus NBRC, Enterococcus nlaezlc434, Enterococcus nlaezlg106, Enterococcus nlaezlg87, Enterococcus nlaezlh339, Enterococcus nlaezlh375, Enterococcus nlaezlh381, Enterococcus nlaezlh383, Enterococcus nlaezlh405, Enterococcus nlaezlp116, Enterococcus nlaezlp148, Enterococcus nlaezlp401, Enterococcus nlaezlp650, Enterococcus pseudoavium, Enterococcus R-25205, Enterococcus raffinosus, Enterococcus rottae, Enterococcus RU07, Enterococcus saccharolyticus, Enterococcus saccharominimus, Enterococcus sanguinicola, Enterococcus SCA16, Enterococcus SCA2, Enterococcus SE138, Enterococcus SF-1, Enterococcus sulfureus, Enterococcus SV6, Enterococcus te1a, Enterococcus te32a, Enterococcus te42a, Enterococcus te45r, Enterococcus te49a, Enterococcus te51a, Enterococcus te58r, Enterococcus te59r, Enterococcus te61r, Enterococcus te93r, Enterococcus te95a, Enterococcus, Enterorhabdus, Enterorhabdus caecimuris, Enterorhabdus, Erwinia, Erwinia agglomerans, Erwinia enterica, Erwinia rhapontici, Erwinia tasmaniensis, Erwinia, Erysipelotrichaceae_incertae_sedis, Erysipelotrichaceae_incertae_sedis aff, Erysipelotrichaceae_incertae_sedis bacterium, Erysipelotrichaceae_incertae_sedis biforme, Erysipelotrichaceae_incertae_sedis C-1, Erysipelotrichaceae_incertae_sedis cylindroides, Erysipelotrichaceae_incertae_sedis GK12, Erysipelotrichaceae_incertae_sedis innocuum, Erysipelotrichaceae_incertae_sedis nlaezlc332, Erysipelotrichaceae_incertae_sedis nlaezlc340, Erysipelotrichaceae_incertae_sedis nlaezlg420, Erysipelotrichaceae_incertae_sedis nlaezlg425, Erysipelotrichaceae_incertae_sedis nlaezlg440, Erysipelotrichaceae_incertae_sedis nlaezlg463, Erysipelotrichaceae_incertae_sedis nlaezlh340, Erysipelotrichaceae_incertae_sedis nlaezlh354, Erysipelotrichaceae_incertae_sedis nlaezlh379, Erysipelotrichaceae_incertae_sedis nlaezlh380, Erysipelotrichaceae_incertae_sedis nlaezlh385, Erysipelotrichaceae_incertae_sedis nlaezlh410, Erysipelotrichaceae_incertae_sedis tortuosum, Erysipelotrichaceae_incertae_sedis, Escherichia/Shigella, Escherichia/Shigella 29(2010), Escherichia/Shigella 4091, Escherichia/Shigella 4104, Escherichia/Shigella 8gw18, Escherichia/Shigella A94, Escherichia/Shigella albertii, Escherichia/Shigella B-1012, Escherichia/Shigella B4, Escherichia/Shigella bacterium, Escherichia/Shigella BBDP15, Escherichia/Shigella BBDP80, Escherichia/Shigella boydii, Escherichia/Shigella carotovorum, Escherichia/Shigella CERAR, Escherichia/Shigella coli, Escherichia/Shigella DBC-1, Escherichia/Shigella dc262011, Escherichia/Shigella dysenteriae, Escherichia/Shigella enrichment, Escherichia/Shigella escherichia, Escherichia/Shigella fecal, Escherichia/Shigella fergusonii, Escherichia/Shigella flexneri, Escherichia/Shigella GDR05, Escherichia/Shigella GDR07, Escherichia/Shigella H7, Escherichia/Shigella marine, Escherichia/Shigella ML2-46, Escherichia/Shigella mpnisolate, Escherichia/Shigella NA, Escherichia/Shigella nlaezlg330, Escherichia/Shigella nlaezlg400, Escherichia/Shigella nlaezlg441, Escherichia/Shigella nlaezlg506, Escherichia/Shigella nlaezlh204, Escherichia/Shigella nlaezlh208, Escherichia/Shigella nlaezlh209, Escherichia/Shigella nlaezlh213, Escherichia/Shigella nlaezlh214, Escherichia/Shigella nlaezlh4, Escherichia/Shigella nlaezlh435, Escherichia/Shigella nlaezlh81, Escherichia/Shigella nlaezlp126, Escherichia/Shigella nlaezlp198, Escherichia/Shigella nlaezlp21, Escherichia/Shigella nlaezlp235, Escherichia/Shigella nlaezlp237, Escherichia/Shigella nlaezlp239, Escherichia/Shigella nlaezlp25, Escherichia/Shigella nlaezlp252, Escherichia/Shigella nlaezlp275, Escherichia/Shigella nlaezlp280, Escherichia/Shigella nlaezlp51, Escherichia/Shigella nlaezlp53, Escherichia/Shigella nlaezlp669, Escherichia/Shigella nlaezlp676, Escherichia/Shigella nlaezlp717, Escherichia/Shigella nlaezlp731, Escherichia/Shigella nlaezlp826, Escherichia/Shigella nlaezlp877, Escherichia/Shigella nlaezlp884, Escherichia/Shigella NMU-ST2, Escherichia/Shigella oc182011, Escherichia/Shigella of, Escherichia/Shigella proteobacterium, Escherichia/Shigella Q1, Escherichia/Shigella sakazakii, Escherichia/Shigella SF6, Escherichia/Shigella sm1719, Escherichia/Shigella SOD-7317, Escherichia/Shigella sonnei, Escherichia/Shigella SW86, Escherichia/Shigella, Escherichia/Shigella vulneris, Ethanoligenens, Ethanoligenens harbinense, Ethanoligenens, Eubacterium, Eubacterium ARC-2, Eubacterium callanderi, Eubacterium E-1, Eubacterium G3(2011), Eubacterium infirmum, Eubacterium limosum, Eubacterium methylotrophicum, Eubacterium nlaezlp439, Eubacterium nlaezlp457, Eubacterium nlaezlp458, Eubacterium nlaezlp469, Eubacterium nlaezlp474, Eubacterium oral, Eubacterium saphenum, Eubacterium sulci, Eubacterium, Eubacterium WAL, Euglenida, Euglenida longa, Faecalibacterium, Faecalibacterium bacterium, Faecalibacterium canine, Faecalibacterium DJF_VR20, Faecalibacterium ic1379, Faecalibacterium prausnitzii, Faecalibacterium, Filibacter, Filibacter globispora, Flavobacterium, Flavobacterium SSL03, Flavobacterium, Flavonifractor, Flavonifractor AUH-JLC235, Flavonifractor enrichment, Flavonifractor nlaezlc354, Flavonifractor orbiscindens, Flavonifractor plautii, Flavonifractor, Francisella, Francisella piscicida, Fusobacterium, Fusobacterium nucleatum, Fusobacterium, Gardnerella, Gardnerella, Gardnerella vaginalis, Gemmiger, Gemmiger DJF_VR33k2, Gemmiger formicilis, Gemmiger, Geobacter, Geobacter, Gordonibacter, Gordonibacter bacterium, Gordonibacter intestinal, Gordonibacter pamelaeae, Gordonibacter, Gp2, Gp2, Gp21, Gp21, Gp4, Gp4, Gp6, Gp6, Granulicatella, Granulicatella adiacens, Granulicatella enrichment, Granulicatella oral, Granulicatella paraadiacens, Granulicatella, Haemophilus, Haemophilus, Hafnia, Hafnia 3-12(2010), Hafnia alvei, Hafnia CC16, Hafnia proteus, Hafnia, Haliea, Haliea, Hallella, Hallella seregens, Hallella, Herbaspirillum, Herbaspirillum 022S4-11, Herbaspirillum seropedicae, Hespellia, Hespellia porcina, Hespellia stercorisuis, Hespellia, Holdemania, Holdemania AP2, Holdemania filiformis, Holdemania, Howardella, Howardella, Howardella ureilytica, Hydrogenoanaerobacterium, Hydrogenoanaerobacterium saccharovorans, Hydrogenophaga, Hydrogenophaga bacterium, Ilumatobacter, Ilumatobacter, Janthinobacterium, Janthinobacterium C30An7, Janthinobacterium, Jeotgalicoccus, Jeotgalicoccus, Klebsiella, Klebsiella aerogenes, Klebsiella bacterium, Klebsiella E1L1, Klebsiella EB2-THQ, Klebsiella enrichment, Klebsiella F83, Klebsiella G1-6, Klebsiella gg160e, Klebsiella granulomatis, Klebsiella HaNA20, Klebsiella HF2, Klebsiella ii_3_chl_1, Klebsiella KALAICIBA17, Klebsiella kpu, Klebsiella M3, Klebsiella MB45, Klebsiella milletis, Klebsiella NCCP-138, Klebsiella ok1_1_9_S16, Klebsiella ok1_1_9_S54, Klebsiella planticola, Klebsiella pneumoniae, Klebsiella poinarii, Klebsiella PSB26, Klebsiella RS, Klebsiella Se14, Klebsiella SRC_DSD12, Klebsiella td153s, Klebsiella TG-1, Klebsiella TPS5, Klebsiella, Klebsiella variicola, Klebsiella WB-2, Klebsiella Y9, Klebsiella zlmy, Kluyvera, Kluyvera An5-1, Kluyvera cryocrescens, Kluyvera, Kocuria, Kocuria 2216.35.31, Kurthia, Kurthia, Lachnobacterium, Lachnobacterium C12b, Lachnobacterium, Lachnospiracea_incertae_sedis, Lachnospiracea_incertae_sedis bacterium, Lachnospiracea_incertae_sedis contortum, Lachnospiracea_incertae_sedis Eg2, Lachnospiracea_incertae_sedis eligens, Lachnospiracea_incertae_sedis ethanolgignens, Lachnospiracea_incertae_sedis galacturonicus, Lachnospiracea_incertae_sedis gnavus, Lachnospiracea_incertae_sedis hallii, Lachnospiracea_incertae_sedis hydrogenotrophica, Lachnospiracea_incertae_sedis ID5, Lachnospiracea_incertae_sedis intestinal, Lachnospiracea_incertae_sedis mpnisolate, Lachnospiracea_incertae_sedis pectinoschiza, Lachnospiracea_incertae_sedis ramulus, Lachnospiracea_incertae_sedis rectale, Lachnospiracea_incertae_sedis RLB1, Lachnospiracea_incertae_sedis rumen, Lachnospiracea_incertae_sedis SY8519, Lachnospiracea_incertae_sedis torques, Lachnospiracea incertae_sedis, Lachnospiracea_incertae_sedis uniforme, Lachnospiracea_incertae_sedis ventriosum, Lachnospiracea_incertae_sedis xylanophilum, Lachnospiracea_incertae_sedis ye62, Lactobacillus, Lactobacillus 5-1-2, Lactobacillus 66c, Lactobacillus acidophilus, Lactobacillus arizonensis, Lactobacillus B5406, Lactobacillus brevis, Lactobacillus casei, Lactobacillus crispatus, Lactobacillus curvatus, Lactobacillus delbrueckii, Lactobacillus fermentum, Lactobacillus gasseri, Lactobacillus helveticus, Lactobacillus hominis, Lactobacillus ID9203, Lactobacillus IDSAc, Lactobacillus intestinal, Lactobacillus johnsonii, Lactobacillus lactis, Lactobacillus manihotivorans, Lactobacillus mucosae, Lactobacillus NA, Lactobacillus oris, Lactobacillus P23, Lactobacillus P8, Lactobacillus paracasei, Lactobacillus paraplantarum, Lactobacillus pentosus, Lactobacillus plantarum, Lactobacillus pontis, Lactobacillus rennanqilfy10, Lactobacillus rennanqilfy14, Lactobacillus rennanqilfy9, Lactobacillus reuteri, Lactobacillus rhamnosus, Lactobacillus salivarius, Lactobacillus sanfranciscensis, Lactobacillus suntoryeus, Lactobacillus T3R1C1, Lactobacillus, Lactobacillus vaginalis, Lactobacillus zeae, Lactococcus, Lactococcus 56, Lactococcus CR-317S, Lactococcus CW-1, Lactococcus D8, Lactococcus Da-18, Lactococcus DAP39, Lactococcus delbrueckii, Lactococcus F116, Lactococcus fujiensis, Lactococcus G22, Lactococcus garvieae, Lactococcus lactis, Lactococcus manure, Lactococcus RTS, Lactococcus SXVIII1(2011), Lactococcus TP2MJ, Lactococcus TP2ML, Lactococcus TP2MN, Lactococcus U5-1, Lactococcus, Lactonifactor, Lactonifactor bacterium, Lactonifactor longoviformis, Lactonifactor nlaezlc533, Lactonifactor, Leclercia, Leclercia, Lentisphaera, Lentisphaera, Leuconostoc, Leuconostoc carnosum, Leuconostoc citreum, Leuconostoc garlicum, Leuconostoc gasicomitatum, Leuconostoc gelidum, Leuconostoc inhae, Leuconostoc lactis, Leuconostoc MEBE2, Leuconostoc mesenteroides, Leuconostoc pseudomesenteroides, Leuconostoc, Limnobacter, Limnobacter spf3, Luteolibacter, Luteolibacter bacterium, Lutispora, Lutispora, Marinifilum, Marinifilum, Marinobacter, Marinobacter arcticus, Mariprofundus, Mariprofundus, Marvinbryantia, Marvinbryantia, Megamonas, Megamonas, Megasphaera, Megasphaera, Melissococcus, Melissococcus faecalis, Methanobacterium, Methanobacterium subterraneum, Methanobrevibacter, Methanobrevibacter arboriphilus, Methanobrevibacter millerae, Methanobrevibacter olleyae, Methanobrevibacter oralis, Methanobrevibacter SM9, Methanobrevibacter smithii, Methanobrevibacter, Methanosphaera, Methanosphaera stadtmanae, Methanosphaera, Methylobacterium, Methylobacterium adhaesivum, Methylobacterium bacterium, Methylobacterium iEII3, Methylobacterium MP3, Methylobacterium oryzae, Methylobacterium PB132, Methylobacterium PB20, Methylobacterium PB280, Methylobacterium PDD-23b-14, Methylobacterium radiotolerans, Methylobacterium SKJH-1, Methylobacterium, Mitsuokella, Mitsuokella jalaludinii, Mitsuokella, Morganella, Morganella morganii, Moritella, Moritella 2D2, Moryella, Moryella indoligenes, Moryella naviforme, Moryella, Mycobacterium, Mycobacterium tuberculosis, Mycobacterium, Negativicoccus, Negativicoccus, Nitrosomonas, Nitrosomonas eutropha, Novosphingobium, Novosphingobium, Odoribacter, Odoribacter laneus, Odoribacter splanchnicus, Odoribacter, Olsenella, Olsenella 1832, Olsenella F0206, Olsenella, Orbus, Orbus gilliamella, Oribacterium, Oribacterium, Oscillibacter, Oscillibacter bacterium, Oscillibacter enrichment, Oscillibacter, Owenweeksia, Owenweeksia, Oxalobacter, Oxalobacter formigenes, Oxalobacter, Paludibacter, Paludibacter, Pantoea, Pantoea agglomerans, Pantoea eucalypti, Pantoea, Papillibacter, Papillibacter cinnamivorans, Papillibacter, Parabacteroides, Parabacteroides ASF519, Parabacteroides CR-34, Parabacteroides distasonis, Parabacteroides DJF_B084, Parabacteroides DJF_B086, Parabacteroides dnLKV8, Parabacteroides enrichment, Parabacteroides fecal, Parabacteroides goldsteinii, Parabacteroides gordonii, Parabacteroides johnsonii, Parabacteroides merdae, Parabacteroides mpnisolate, Parabacteroides nlaezlp340, Parabacteroides, Paraeggerthella, Paraeggerthella hongkongensis, Paraeggerthella nlaezlp797, Paraeggerthella nlaezlp896, Paraprevotella, Paraprevotella clara, Paraprevotella, Paraprevotella xylaniphila, Parasutterella, Parasutterella excrementihominis, Parasutterella, Pectobacterium, Pectobacterium carotovorum, Pectobacterium wasabiae, Pediococcus, Pediococcus te2r, Pediococcus, Pedobacter, Pedobacter b3N1b-b5, Pedobacter daechungensis, Pedobacter, Peptostreptococcus, Peptostreptococcus anaerobius, Peptostreptococcus stomatis, Peptostreptococcus, Phascolarctobacterium, Phascolarctobacterium faecium, Phascolarctobacterium, Photobacterium, Photobacterium MIE, Pilibacter, Pilibacter, Planctomyces, Planctomyces, Planococcaceae_incertae_sedis, Planococcaceae_incertae_sedis, Planomicrobium, Planomicrobium, Plesiomonas, Plesiomonas, Porphyrobacter, Porphyrobacter KK348, Porphyromonas, Porphyromonas asaccharolytica, Porphyromonas bennonis, Porphyromonas canine, Porphyromonas somerae, Porphyromonas, Prevotella, Prevotella bacterium, Prevotella BI-42, Prevotella bivia, Prevotella buccalis, Prevotella copri, Prevotella DJF_B112, Prevotella mpnisolate, Prevotella oral, Prevotella, Propionibacterium, Propionibacterium acnes, Propionibacterium freudenreichii, Propionibacterium LG, Propionibacterium, Proteiniborus, Proteiniborus, Proteiniphilum, Proteiniphilum, Proteus, Proteus HS7514, Providencia, Providencia, Pseudobutyrivibrio, Pseudobutyrivibrio bacterium, Pseudobutyrivibrio fibrisolvens, Pseudobutyrivibrio ruminis, Pseudobutyrivibrio, Pseudochrobactrum, Pseudochrobactrum, Pseudoflavonifractor, Pseudoflavonifractor asf500, Pseudoflavonifractor bacterium, Pseudoflavonifractor capillosus, Pseudoflavonifractor NML, Pseudoflavonifractor, Pseudomonas, Pseudomonas 1043, Pseudomonas 10569, Pseudomonas 127

(39-zx), Pseudomonas 12A_19, Pseudomonas 145(38zx), Pseudomonas 22010, Pseudomonas 32010, Pseudomonas 34t20, Pseudomonas 3C_10, Pseudomonas 4-5(2010), Pseudomonas 4-9(2010), Pseudomonas 6-13.J, Pseudomonas 63596, Pseudomonas 82010, Pseudomonas a001-142L, Pseudomonas a101-18-2, Pseudomonas a111-5, Pseudomonas aeruginosa, Pseudomonas agarici, Pseudomonas amsp1, Pseudomonas AU2390, Pseudomonas AZ18R1, Pseudomonas azotoformans, Pseudomonas B122, Pseudomonas B65 (2012), Pseudomonas bacterium, Pseudomonas BJSX, Pseudomonas BLH-8D5, Pseudomonas BWDY-29, Pseudomonas CA18, Pseudomonas Cantas12, Pseudomonas CB11, Pseudomonas CBZ-4, Pseudomonas cedrina, Pseudomonas CGMCC, Pseudomonas CL16, Pseudomonas CNE, Pseudomonas corrugata, Pseudomonas cuatrocienegasensis, Pseudomonas CYEB-7, Pseudomonas D5, Pseudomonas DAP37, Pseudomonas DB48, Pseudomonas deceptionensis, Pseudomonas Den-05, Pseudomonas DF7EH1, Pseudomonas DhA-91, Pseudomonas DVS14a, Pseudomonas DYJK4-9, Pseudomonas DZQ5, Pseudomonas E11_ICE19B, Pseudomonas E2.2, Pseudomonas e2-CDC-TB4D2, Pseudomonas EM189, Pseudomonas enrichment, Pseudomonas extremorientalis, Pseudomonas FAIR/BE/F/GH37, Pseudomonas FAIR/BE/F/GH39, Pseudomonas FAIR/BE/F/GH94, Pseudomonas FLM05-3, Pseudomonas fluorescens, Pseudomonas fragi, Pseudomonas 'FSL, Pseudomonas G1013, Pseudomonas gingeri, Pseudomonas HC2-2, Pseudomonas HC2-4, Pseudomonas HC2-5, Pseudomonas HC4-8, Pseudomonas HC6-6, Pseudomonas Hg4-06, Pseudomonas HLB8-2, Pseudomonas HLS12-1, Pseudomonas HSF20-13, Pseudomonas HW08, Pseudomonas 11-44, Pseudomonas IpA-92, Pseudomonas IV, Pseudomonas JCM, Pseudomonas jessenii, Pseudomonas JSPBS, Pseudomonas K3R3.1A, Pseudomonas KB40, Pseudomonas KB42, Pseudomonas KB44, Pseudomonas KB63, Pseudomonas KB73, Pseudomonas KK-21-4, Pseudomonas KOPRI, Pseudomonas L1R3.5, Pseudomonas LAB-27, Pseudomonas LAB-44, Pseudomonas Lc10-2, Pseudomonas libanensis, Pseudomonas Ln5C.7, Pseudomonas LS197, Pseudomonas lundensis, Pseudomonas marginalis, Pseudomonas MFY143, Pseudomonas MFY146, Pseudomonas MY1404, Pseudomonas MY1412, Pseudomonas MY1416, Pseudomonas MY1420, Pseudomonas N14zhy, Pseudomonas NBRC, Pseudomonas NCCP-506, Pseudomonas NFU20-14, Pseudomonas NJ-22, Pseudomonas NJ-24, Pseudomonas Nj-3, Pseudomonas Nj-55, Pseudomonas Nj-56, Pseudomonas Nj-59, Pseudomonas Nj-60, Pseudomonas Nj-62, Pseudomonas Nj-70, Pseudomonas NP41, Pseudomonas OCW4, Pseudomonas OW3-15-3-2, Pseudomonas P1(2010), Pseudomonas P2(2010), Pseudomonas P3(2010), Pseudomonas P4(2010), Pseudomonas PD, Pseudomonas PF1B4, Pseudomonas PF2M10, Pseudomonas PILH1, Pseudomonas poae, Pseudomonas proteobacterium, Pseudomonas ps4-12, Pseudomonas ps4-2, Pseudomonas ps4-28, Pseudomonas ps4-34, Pseudomonas ps4-4, Pseudomonas psychrophila, Pseudomonas putida, Pseudomonas R-35721, Pseudomonas R-37257, Pseudomonas R-37265, Pseudomonas R-37908, Pseudomonas RBE1CD-48, Pseudomonas RBE2CD-42, Pseudomonas regd9, Pseudomonas RKS7-3, Pseudomonas S2, Pseudomonas seawater, Pseudomonas SGb08, Pseudomonas SGb120, Pseudomonas SGb396, Pseudomonas sgn, Pseudomonas 'Shk, Pseudomonas stutzeri, Pseudomonas syringae, Pseudomonas taetrolens, Pseudomonas tolaasii, Pseudomonas trivialis, Pseudomonas TUT1023, Pseudomonas, Pseudomonas W15Feb26, Pseudomonas W15Feb4, Pseudomonas W15Feb6, Pseudomonas WD-3, Pseudomonas WR4-13, Pseudomonas WR7#2, Pseudomonas Y1000, Pseudomonas ZS29-8, Psychrobacter, Psychrobacter umb13d, Psychrobacter, Pyramidobacter, Pyramidobacter piscolens, Pyramidobacter, Rahnella, Rahnella aquatilis, Rahnella carotovorum, Rahnella GIST-WP4w1, Rahnella LR113, Rahnella, Rahnella Z2-S1, Ralstonia, Ralstonia bacterium, Ralstonia, Raoultella, Raoultella B19, Raoultella enrichment, Raoultella planticola, Raoultella sv6xvii, Raoultella SZ015, Raoultella, Renibacterium, Renibacterium G20, Rhizobium, Rhizobium leguminosarum, Rhodococcus, Rhodococcus erythropolis, Rhodopirellula, Rhodopirellula, Riemerella, Riemerella anatipestifer, Rikenella, Rikenella, Robinsoniella, Robinsoniella peoriensis, Robinsoniella, Roseburia, Roseburia 11SE37, Roseburia bacterium, Roseburia cecicola, Roseburia DJF_VR77, Roseburia faecis, Roseburia fibrisolvens, Roseburia hominis, Roseburia intestinalis, Roseburia inulinivorans, Roseburia, Roseibacillus, Roseibacillus, Rothia, Rothia, Rubritalea, Rubritalea, Ruminococcus, Ruminococcus 25F6, Ruminococcus albus, Ruminococcus bacterium, Ruminococcus bromii, Ruminococcus callidus, Ruminococcus champanellensis, Ruminococcus DJF_VR87, Ruminococcus flavefaciens, Ruminococcus gauvreauii, Ruminococcus lactaris, Ruminococcus NK3A76, Ruminococcus, Ruminococcus YE71, Saccharofermentans, Saccharofermentans, Salinicoccus, Salinicoccus, Salinimicrobium, Salinimicrobium, Salmonella, Salmonella agglomerans, Salmonella bacterium, Salmonella enterica, Salmonella freundii, Salmonella hermannii, Salmonella paratyphi, Salmonella SL0604, Salmonella subterranea, Salmonella, Scardovia, Scardovia oral, Schwartzia, Schwartzia, Sedimenticola, Sedimenticola, Sediminibacter, Sediminibacter, Selenomonas, Selenomonas fecal, Selenomonas, Serpens, Serpens, Serratia, Serratia 1135, Serratia 136-2, Serratia 5.1R, Serratia AC-CS-1B, Serratia AC-CS-B2, Serratia aquatilis, Serratia bacterium, Serratia BS26, Serratia carotovorum, Serratia DAP6, Serratia enrichment, Serratia F2, Serratia ficaria, Serratia fonticola, Serratia grimesii, Serratia J145, Serratia JM983, Serratia liquefaciens, Serratia marcescens, Serratia plymuthica, Serratia proteamaculans, Serratia proteolyticus, Serratia ptz-16s, Serratia quinivorans, Serratia SBS, Serratia SS22, Serratia trout, Serratia UA-G004, Serratia, Serratia White, Serratia yellow, Shewanella, Shewanella baltica, Shewanella, Slackia, Slackia intestinal, Slackia isoflavoniconvertens, Slackia NATTS, Slackia, Solibacillus, Solibacillus, Solobacterium, Solobacterium moorei, Solobacterium, Spartobacteria_genera_incertae_sedis, Spartobacteria_genera_incertae_sedis, Sphingobium, Sphingobium, Sphingomonas, Sphingomonas, Sporacetigenium, Sporacetigenium, Sporobacter, Sporobacter, Sporobacterium, Sporobacterium olearium, Staphylococcus, Staphylococcus epidermidis, Staphylococcus PCA17, Staphylococcus, Stenotrophomonas, Stenotrophomonas, Streptococcus, Streptococcus 1606-02B, Streptococcus agalactiae, Streptococcus alactolyticus, Streptococcus anginosus, Streptococcus bacterium, Streptococcus bovis, Streptococcus ChDC, Streptococcus constellatus, Streptococcus CR-314S, Streptococcus criceti, Streptococcus cristatus, Streptococcus downei, Streptococcus dysgalactiae, Streptococcus enrichment, Streptococcus equi, Streptococcus equinus, Streptococcus ES11, Streptococcus eubacterium, Streptococcus fecal, Streptococcus gallinaceus, Streptococcus gallolyticus, Streptococcus gastrococcus, Streptococcus genomosp, Streptococcus gordonii, Streptococcus I5, Streptococcus infantarius, Streptococcus intermedius, Streptococcus Je2, Streptococcus JS-CD2, Streptococcus LRC, Streptococcus luteciae, Streptococcus lutetiensis, Streptococcus M09-11185, Streptococcus mitis, Streptococcus mutans, Streptococcus NA, Streptococcus nlaezlc353, Streptococcus nlaezlp68, Streptococcus nlaezlp758, Streptococcus nlaezlp807, Streptococcus oral, Streptococcus oralis, Streptococcus parasanguinis, Streptococcus phocae, Streptococcus pneumoniae, Streptococcus porcinus, Streptococcus pyogenes, Streptococcus S16-08, Streptococcus salivarius, Streptococcus sanguinis, Streptococcus sobrinus, Streptococcus suis, Streptococcus symbiont, Streptococcus thermophilus, Streptococcus TW1, Streptococcus, Streptococcus vestibularis, Streptococcus warneri, Streptococcus XJ-RY-3, Streptomyces, Streptomyces malaysiensis, Streptomyces MVCS6, Streptophyta, Streptophyta cordifolium, Streptophyta ginseng, Streptophyta hirsutum, Streptophyta oleracea, Streptophyta sativa, Streptophyta sativum, Streptophyta sativus, Streptophyta tabacum, Streptophyta, Subdivision3_genera_incertae_sedis, Subdivision3_genera_incertae_sedis, Subdoligranulum, Subdoligranulum bacterium, Subdoligranulum ic1393, Subdoligranulum ic1395, Subdoligranulum, Subdoligranulum variabile, Succiniclasticum, Succiniclasticum, Sulfuricella, Sulfuricella, Sulfurospirillum, Sulfurospirillum, Sutterella, Sutterella, Sutterella wadsworthensis, Syntrophococcus, Syntrophococcus, Syntrophomonas, Syntrophomonas bryantii, Syntrophomonas, Syntrophus, Syntrophus, Tannerella, Tannerella, Tatumella, Tatumella, Thermofilum, Thermofilum, Thermogymnomonas, Thermogymnomonas, Thermovirga, Thermovirga, Thiomonas, Thiomonas ML1-46, Thorsellia, Thorsellia carsonella, TM7_genera_incertae_sedis, TM7_genera_incertae_sedis, Trichococcus, Trichococcus, Turicibacter, Turicibacter sanguinis, Turicibacter, Vagococcus, Vagococcus bfs11-15, Vagococcus, Vampirovibrio, Vampirovibrio, Varibaculum, Varibaculum, Variovorax, Variovorax KS2D-23, Veillonella, Veillonella dispar, Veillonella MSA12, Veillonella OK8, Veillonella oral, Veillonella parvula, Veillonella tobetsuensis, Veillonella, Vibrio, Vibrio 3C1, Vibrio, Victivallis, Victivallis, Victivallis vadensis, Vitellibacter, Vitellibacter, Wandonia, Wandonia haliotis, Weissella, Weissella cibaria, Weissella confusa, Weissella oryzae, Weissella, Yersinia, Yersinia 9gw38, Yersinia A125, Yersinia aldovae, Yersinia aleksiciae, Yersinia b702011, Yersinia bacterium, Yersinia bercovieri, Yersinia enterocolitica, Yersinia entomophaga, Yersinia frederiksenii, Yersinia intermedia, Yersinia kristensenii, Yersinia MAC, Yersinia massiliensis, Yersinia mollaretii, Yersinia nurmii, Yersinia pekkanenii, Yersinia pestis, Yersinia pseudotuberculosis, Yersinia rohdei, Yersinia ruckeri, Yersinia s10fe31, Yersinia s17fe31, Yersinia s4fe31, Yersinia, Yersinia YEM17B.

Accuracy and Sensitivity

The methods provided herein can provide strain classification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%. The methods provided herein can provide strain quantification of a genera, species or sub-strain level of one or more microbes in a sample with an accuracy of greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9%.

In some applications a similar microbiome profile from a patient to a reference profile indicates an increased likelihood of one or more of: a poor clinical outcome, good clinical outcome, high risk of disease, low risk of disease, complete response, partial response, stable disease, non-response, and recommended treatments for disease management. In some applications, a dissimilar microbiome profile from a patient to a reference profile indicates one or more of: an increased likelihood of a poor clinical outcome, good clinical outcome, high risk of disease, low risk of disease, complete response, partial response, stable disease, non-response, and recommended treatments for disease management.

The methods provided herein can provide a health status of a subject with a specificity greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9% ROC. The methods provided herein can provide a health status of a subject with sensitivity greater than 1%, 20%, 30%, 40%, 50%, 55%, 60%, 65%, 70%, 75%, 80%, 85%, 90%, 95%, 96%, 97%, 98%, 99%, 99.2%, 99.5%, 99.7%, or 99.9% ROC.

The diagnostic methods provided by the present disclosure for the diseases provided herein can have at least one of a sensitivity of 70% or greater and specificity of greater than 70% based on measurement of 15 or fewer microbes in the biological sample. Such diagnostic method can have at least one of a sensitivity greater than 70% and specificity greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes, 200 or fewer microbes, 300 or fewer microbes, 400 or fewer microbes, 500 or fewer microbes, 600 or fewer microbes, 700 or fewer microbes or 800 or fewer microbes.

The microbial profile for a subject provided by the present disclosure can have an accuracy of 70% or greater based on measurement of 15 or fewer microbes in the biological sample. Such profiling method can have at least an accuracy greater than 70% based on measurement of no more than 2 microbes, 3 or fewer microbes, 4 or fewer microbes, 5 or fewer microbes, 6 or fewer microbes, 7 or fewer microbes, 8 or fewer microbes, 9 or fewer microbes, 10 or fewer microbes, 11 or fewer microbes, no more than 12 microbes, 13 or fewer microbes, 14 or fewer microbes, 15 or fewer microbes, 16 or fewer microbes, 18 or fewer microbes, 19 or fewer microbes, 20 or fewer microbes, 25 or fewer microbes, 30 or fewer microbes, 35 or fewer microbes, 40 or fewer microbes, 45 or fewer microbes, 50 or fewer microbes, 55 or fewer microbes, 60 or fewer microbes, 65 or fewer microbes, 70 or fewer microbes, 75 or fewer microbes, 80 or fewer microbes, 85 or fewer microbes, 90 or fewer microbes, or 100 or fewer microbes, 200 or fewer microbes, 300 or fewer microbes, 400 or fewer microbes, 500 or fewer microbes, 600 or fewer microbes, 700 or fewer microbes or 800 or fewer microbes.

III. Computer Systems

The current disclosure provides computer systems for implementing any of the methods described herein. A computer system may be used to implement one or more steps including, sample collection, sample processing, detecting, quantifying one or more microbes, generating a profile data, comparing said data to a reference, generating a subject-specific microbiome profile, comparing the subject-specific profile to a reference profile, receiving medical history, receiving medical records, receiving and storing data obtained by one or more methods described herein, analyzing said data, generating a report, and reporting results to a receiver.

For example, provided herein are computer systems for detecting a presence or absence of a microbes. Also provided herein are computer systems for detecting a presence or absence of bacteria, fungi, archaea or other elements that comprise and maintain a microbiome.

Computer systems described herein may comprise computer-executable code for performing any of the algorithms described herein. Computer systems described herein may comprise computer-executable code for performing any of the algorithms and using the database as herein.

FIG. 1 depicts an exemplary computer system 100 adapted to implement a method described herein. The system 100 includes a central computer server 101 that is programmed to implement exemplary methods described herein. The server 101 includes a central processing unit (CPU, also "processor") 105 which can be a single core processor, a multi core processor, or plurality of processors for parallel processing. The server 101 also includes memory 110 (e.g. random access memory, read-only memory, flash memory); electronic storage unit 115 (e.g. hard disk); communications interface 120 (e.g. network adaptor) for communicating with one or more other systems; and peripheral devices 125 which may include cache, other memory, data storage, and/or electronic display adaptors. The memory 110, storage unit 115, interface 120, and peripheral devices 125 are in communication with the processor 105 through a communications bus (solid lines), such as a motherboard. The storage unit 115 can be a data storage unit for storing data. The server 101 is operatively coupled to a computer network ("network") 130 with the aid of the communications interface 120. The network 130 can be the Internet, an intranet and/or an extranet, an intranet and/or extranet that is in communication with the Internet, a telecommunication or data network. The network 130 in some cases, with the aid of the server 101, can implement a peer-to-peer network, which may enable devices coupled to the server 101 to behave as a client or a server.

The storage unit 115 can store files, such as subject reports, and/or communications with the caregiver, sequencing data, data about individuals, or any aspect of data associated with the invention.

The server can communicate with one or more remote computer systems through the network 130. The one or more remote computer systems may be, for example, personal computers, laptops, tablets, telephones, Smart phones, or personal digital assistants.

In some applications the computer system 100 includes a single server 101. In other situations, the system includes multiple servers in communication with one another through an intranet, extranet and/or the internet.

The server 101 can be adapted to store measurement data or a database as provided herein, patient information from the subject, such as, for example, polymorphisms, mutations, medical history, family history, demographic data and/or other clinical or personal information of potential relevance to a particular application. Such information can be stored on the storage unit 115 or the server 101 and such data can be transmitted through a network.

Methods as described herein can be implemented by way of machine (or computer processor) executable code (or software) stored on an electronic storage location of the server 101, such as, for example, on the memory 110, or electronic storage unit 115. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110. Alternatively, the code can be executed on a second computer system 140.

Aspects of the systems and methods provided herein, such as the server 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution Computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

A. Databases

Computer systems disclosed herein may comprise a memory unit. The memory unit can be configured to receive data comprising extracting data from a pubic database, detecting, quantifying and profiling one or more microbiomes. The microbiome profile can be any organism known to comprise a microbiome. Examples of such organisms are provided herein.

There are several public microbe (bacteria, fungi, and archaea) and viral protein and genome databases known in the art. The present methods of the disclosure can be used with such public databases. Examples of public databases include but are not limited to Biocyc, Ensembl Bacteria, The Integrated Microbial Genomes, MicrobesOnline, Microbial Genomes from Genome Channel, Microbial Genomes at NCBI, RCSB protein database, Sanger Centre Bacterial Genomes, Ribosomal Database Project (RDP), or DOE JGI Microbial Genomics Database.

The current disclosure also provides for a database that has additional or more accurate microbe information such as the composition of particular microbiomes in a particular cohort, or microbiome reference profiles of a particular cohort. Such database can include but are not limited to additional or more accurate sequences comprising the 16S subunit of ribosome for a given microbe strain, additional or more accurate sequence comprising the 23S subunit of ribosome for a given microbe strain, additional or more accurate information of the sequence comprising the intergenic region between the 16S subunit and 23S subunit of ribosome, additional or more accurate information of the sequence comprising variable regions in the 16S ribosome for a particular strain, additional or more accurate information of the sequence comprising variable regions in the 23S subunit of ribosome for a particular strain, additional or more accurate information of the sequence comprising variable regions with a high accuracy in strain resolution at the genus level, additional or more accurate information of the sequence comprising variable regions with a high accuracy in strain resolution at the species level, or additional or more accurate information of the sequence comprising variable regions with a high accuracy in strain resolution at the sub-type level.

Such a database that has additional or more accurate genome information can be comprised of sequence reads greater than 500 base pair, 600 base pair, 700 base pair, 800 base pair, 900 base pair, 1000 base pair, 1100 base pair, 1200 base pair, 1300 base pair, 1400 base pair, 16S subunit of ribosome for a given microbe strain. Such a database can be comprised of sequence reads greater than 500 base pair, 600 base pair, 700 base pair, 800 base pair, 900 base pair, 1000 base pair, 1100 base pair, 1200 base pair, 1300 base pair, 1400 base pair, 16S or 23S subunit of ribosome for a given microbe strain.

Such a database can be comprised of sequence reads greater than 500 base pair, 600 base pair, 700 base pair, 800 base pair, 900 base pair, 1000 base pair, 1100 base pair, 1200 base pair, 1300 base pair, 1400 base pair, comprising the intergenic region between the 16S subunit and 23S subunit of ribosome for a given bacterial strain.

Such a database can be comprised of sequence reads greater than 500 base pair, 600 base pair, 700 base pair, 800 base pair, 900 base pair, 1000 base pair, 1100 base pair, 1200 base pair, 1300 base pair, 1400 base pair, 1500 base pair comprising the variable regions in the 16S ribosome. Such a database can be comprised of sequence reads greater than 500 base pair, 600 base pair, 700 base pair, 800 base pair, 900 base pair, 1000 base pair, 1100 base pair, 1200 base pair, 1300 base pair, 1400 base pair, 1500 base pair comprising the variable regions in the 16S or 23S ribosome.

Such a database can further comprise of additional or more accurate proteome information can be comprised of sequence reads greater than 500 amino acids, 600 amino acids, 700 amino acids, 800 amino acids, 900 amino acids, 1000 amino acids, 1100 amino acids, 1200 amino acids, 1300 amino acids, 1400 amino acids, 16S subunit of ribosome for a given microbe strain. Such a database can be comprised of sequence reads greater than 500 amino acids, 600 amino acids, 700 amino acids, 800 amino acids, 900 amino acids, 1000 amino acids, 1100 amino acids, 1200 amino acids, 1300 amino acids, 1400 amino acids, 16S or 23S subunit of ribosome for a given microbe strain.

Such a database can be comprised of sequence reads greater than 500 amino acids, 600 amino acids, 700 amino acids, 800 amino acids, 900 amino acids, 1000 amino acids, 1100 amino acids, 1200 amino acids, 1300 amino acids, 1400 amino acids, comprising the intergenic region between the 16S subunit and 23S subunit of ribosome for a given bacterial strain.

Such a database can be comprised of sequence reads greater than 500 amino acids, 600 amino acids, 700 amino acids, 800 amino acids, 900 amino acids, 1000 amino acids, 1100 amino acids, 1200 amino acids, 1300 amino acids, 1400 amino acids, 1500 amino acids comprising the variable regions in the 16S ribosome.

Such a database can be comprised of sequence reads greater than 500 amino acids, 600 amino acids, 700 amino acids, 800 amino acids, 900 amino acids, 1000 amino acids, 1100 amino acids, 1200 amino acids, 1300 amino acids, 1400 amino acids, 1500 amino acids comprising the variable regions in the 16S or 23S ribosome.

The database maybe located on central server containing the computer-executable code that allows access to a user. The user can connect to the central server through a physical connection or cloud-based connection depending on the application. In some applications a portion of the database and necessary executable code will be supplied to as user on appropriate storage media.

B. Computer Generated Report

The computer system can further comprise computer-executable code for providing a report communicating the detecting, measuring, or determining a profile of a microbiome from a subject. Measuring, or determining a profile of a microbiome can include the use of a database as provided herein.

Computer systems disclosed herein may comprise computer-executable code for performing at least one of: generating a cohort-generalized microbiome profile or a subject-specific microbiome profile based upon the measurement data from a biological sample from the subject, comparing the cohort-generalized microbiome profile or subject-specific microbiome profile to at least one reference and determining the health status of a subject.

In some applications the computer system can access the computer-executable code by having a connection to a central server that contained the computer-executable code to generate a report comprising at least one clinical recommendation such as for example, disease state, diagnosis, prognosis, treatment suggestions or procedures for clinical management in a subject which can be retrieved by a health worker or clinician via said central server. The connection to a central server containing the computer-executable code can be a physical connection or cloud-based connection depending on the application.

IV. Kits

The disclosure provides kits. A kit described herein can comprise one or more compositions, reagents, buffers, components for measuring or detecting one or more microbes or microbiomal profiles by a method provided herein. A kit as can further comprise instructions for practicing any of the methods provided herein. For example, instructions can include specifics sample preparation steps for the biological samples as provided herein and it for measuring or detecting. Likewise, the contents of the kit will be tailored to its particular application and sample type.

The kits can further comprise reagents to enable the detection by such applications as PCR, DNA/RNA array, protein array, sequencing, mass spectrometry, immunohistochemistry, laser cell microdissection, high-content cell screening, flow cytometry, which are suitable with the methods described herein for detection and determination of a subject's prognosis, prediction of response, and diagnosis.

Kits can further comprise a software package for measuring or determining of a microbiome profile as, which as described herein, can include reference microbiome profiles or other health related data. In some applications the kits software package including connection to a central server to conduct for measuring or determining and can generate a report comprising at least one clinical recommendation such as for example, disease state, diagnosis, prognosis, treatment suggestions or procedures for clinical management in a subject which can be retrieved by a health worker or clinician via said central server.

In some applications, kits can further comprise a report. The report can be a paper or an electronic report. The report can be generated by computer software (e.g. computer-executable code) provided with the kit, or by a computer sever which the user uploads to a website wherein the computer server generates the report.

In some applications the kit can provide for profiling more than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 microbes at the genera, species, sub-strain level or a combination thereof.

In general, kits will comprise of a packaging material. As used herein, the term "packaging material" can refer to a physical structure housing the components of the kit. The packaging material can maintain sterility of the kit components, and can be made of material commonly used for such purposes (e.g., paper, corrugated fiber, glass, plastic, foil, ampules, etc.). Depending on the applications, kits can also include such materials as a buffering agent, a preservative, or a protein or nucleic acid stabilizing agents or any such materials that are necessary for the stable transport of biological samples and reagents.

V. Microbial-Based Therapeutics and Cosmetics

Provided herein are compositions that may be administered as therapeutics or cosmetics or as a cosmetic. One or more, or combination thereof the microorganisms provided herein can be used to created various formulations for treating a subject. The present disclosure provides therapeutic or cosmetic formulations for the following conditions IBD, preterm labor, obesity, diabetic foot ulcers, bacteremia, acne, infantile colic, type 2 diabetes, C. difficile, IBS, asthma, autism, psoriasis, allergies, cardiovascular disease, cancer, depression, cystic fibrosis, multiple sclerosis, urinary tract infection, radiation enteropathy, drug metabolism, chronic fatigue, and type 1 diabetes.

A. Formulations

Formulations provided herein can include the addition of one or more genetic elements to the therapeutics or cosmetics in order to enhance stability. Formulations provided herein can include those suitable for oral including buccal and sub-lingual, rectal, intranasal, topical, transdermal, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

The appropriate quantity of a therapeutic or cosmetic composition to be administered, the number of treatments, and unit dose will vary according to the subject and the disease state of the subject. The person responsible for administration will determine the appropriate dose, number of treatments, etc. for the subject.

In various applications, the therapeutic or cosmetic composition can include carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

In some applications, the therapeutic or cosmetic composition is substantially free of preservatives. In other applications, the compositon may contain at least one preservative. General methodology on pharmaceutical dosage forms is found in Ansel et al., Pharmaceutical Dosage Forms and Drug Delivery Systems (Lippencott Williams & Wilkins, Baltimore Md. (1999). It will be recognized that, while any suitable carrier known to those of ordinary skill in the art may be employed to administer the compositions provided herein, the type of carrier will vary depending on the mode of administration. A thorough discussion of acceptable carriers/excipients can be found in Remington's Pharmaceutical Sciences, Gennaro, AR, ed., 20th edition, 2000: Williams and Wilkins PA, USA.

A therapeutic or cosmetic composition may also be encapsulated within liposomes using well-known technology. Biodegradable microspheres may also be employed as carriers for the therapeutics or cosmetics compositions provided herein. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The composition may be administered in liposomes or microspheres or microparticles. Methods for preparing liposomes and microspheres for administration to a patient are well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The compositions provided herein may be formulated as a sterile solution or suspension, in suitable vehicles, well known in the art. The therapeutic or cosmetic compositions may be sterilized by conventional techniques or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

VI. Indications

As mentioned above, research indicates that microbiomes can have an effect on a subject's disease status and clinical treatment response. For example, obese and lean individuals can be categorized based on differences in specific species of microbes (Future Microbiol. (2012) 7(1): 91-109. Additionally, in another example the administration of *Lactobacillus gasseri SBT*2055 to lean individuals had observable weight loss (Micr. Path. (2012) 53(2): 100-108; Eur J Clin Nutr (2010) 64:636-43). On the other hand for obese individuals it was *Lactobacillus plantarum* that had the biggest weight loss effect (Micr. Path. (2012) 53(2): 100-108; Eur J Clin Nutr (2010) 64:636-43).

These studies indicate that specifically tailoring treatment to a subjects' microbiome may have beneficial effects on a subject's health status or ameliorate certain symptoms associated with the onset of an indication.

Furthermore, in non-obese individuals, the acetate producing fermentation reaction is limited by the partial pressure of hydrogen which creates a thermodynamic roadblock to further fermentation (Dolfing & Tiedje, 54 Appl. Environ. Microbiol. 1871-3 1988; Schink, 61 Microbiol. Mol. Bio. Rev. 262-80 1997). Obese individuals on the other hand have hydrogen-oxidizing methanogens that can consume the hydrogen and thus allow the acetate producing fermentation reaction to continue. The gut of obese individuals actually uniquely contains hydrogen-oxidizing methanogenic Archaea (Zhang et al PNAS 106:2365-70 2009) and higher levels of Prevotellaceae (Bacteroidetes phylum) (Turnbaugh 2006), which are known to perform the carbohydrate fermentation reaction to acetate and hydrogen.

Indications that can be used with the present disclosure include, but are not limited to the following: IBD, preterm labor, obesity, diabetic foot ulcers, bacteremia, acne, infantile colic, type 2 diabetes, C. difficile, IBS, asthma, autism, psoriasis, allergies, cardiovascular disease, cancer, depression, cystic fibrosis, multiple sclerosis, urinary tract infection, radiation enteropathy, drug metabolism, chronic fatigue, and type 1 diabetes.

Inflammatory bowel disease (IBD) involves chronic inflammation of all or part of the digestive tract. IBD primarily includes ulcerative colitis and Crohn's disease. IBD can be painful and debilitating, and sometimes leads to life-threatening complications. The methods, compositions, systems and kits of the present disclosure provide for a diagnostic assay of at least one microbiome that includes a report that gives guidance on health status or treatment modalities for IBD, ulcerative colitis or Crohn's disease. The present disclosure also provides therapeutic or cosmetic formulations for treatment of inflammatory bowel disease conditions.

Preterm labor occurs when contractions begin to open the cervix before 37 weeks of pregnancy. The earlier premature birth happens, the greater the health risks for the developing baby. Many premature babies need special care in the neonatal intensive care unit. Premature babies can also have long-term mental and physical disabilities. The methods, compositions, systems and kits of the present disclosure provide for a diagnostic assay of at least one microbiome that includes a report that gives guidance on health status or treatment modalities for preterm labor. The present disclosure also provides therapeutic or cosmetic formulations for treatment of preterm labor.

Obesity is a complex disorder involving an excessive amount of body fat. Obesity increases the risk of diseases and health problems such as heart disease, diabetes and high blood pressure. The methods, compositions, systems and kits of the present disclosure provide for a diagnostic assay of at least one microbiome that includes a report that gives guidance on health status or treatment modalities for obesity. The present disclosure also provides therapeutic or cosmetic formulations for treatment of obesity conditions.

Peripheral neuropathy is the most common form of diabetic neuropathy. The feet and legs are often affected first, followed by the hands and arms. Possible signs and symptoms of peripheral neuropathy can include serious foot problems, such as ulcers, infections, deformities, and bone and joint pain. The methods, compositions, systems and kits of the present disclosure provide for a diagnostic assay of at least one microbiome that includes a report that gives guidance on health status or treatment modalities for diabetic neuropathy. The present disclosure also provides therapeutic or cosmetic formulations for treatment of diabetic neuropathy conditions.

Bacteremia or septicemia refers to the presence of bacteria in the blood. A diagnosis of bacteremia is usually confirmed by a blood culture. Treatment usually requires hospitalization and intravenous antibiotics. Without prompt treatment, bacteremia can quickly progress to severe sepsis. The methods, compositions, systems and kits of the present disclosure provide for a diagnostic assay of at least one microbiome that includes a report that gives guidance on health status or treatment modalities for bacteremia, which can include the antibiotic susceptibilities of the infection. The present disclosure also provides therapeutic or cosmetic formulations for treatment of bacteremia.

Acne is a skin condition that occurs when the hair follicles become plugged with oil and dead skin cells. Acne most commonly appears on the face, neck, chest, back and shoulders. Depending on its severity of the acne, this condition can cause emotional distress and lead to scarring of the skin. The methods, compositions, systems and kits of the present disclosure provide for a diagnostic assay of that includes a report that gives guidance on health status or treatment modalities for acne. The present disclosure also provides therapeutic or cosmetic formulations for treatment of acne conditions.

Infantile colic physicians and parents use the term colic to describe an infant with excessive crying, irritability, or fussiness. Babies with colic often cry more than three hours a day, three days a week for three weeks or longer. The methods, compositions, systems and kits of the present disclosure provide for a diagnostic assay of at least one microbiome that includes a report that gives guidance on health status or treatment modalities for infantile colic. The present disclosure also provides therapeutic or cosmetic formulations for treatment of the above-mentioned condition.

Type 2 diabetes, once known as adult-onset or noninsulin-dependent diabetes, is a chronic condition that affects the way the body metabolizes glucose. With type 2 diabetes, the body either resists the effects of insulin or doesn't produce enough insulin to maintain a normal glucose level. Untreated, type 2 diabetes can be life-threatening. The methods, compositions, systems and kits of the present disclosure provide for a diagnostic assay of at least one microbiome that includes a report that gives guidance on health status or treatment modalities for type 2 diabetes. The present disclosure also provides therapeutic or cosmetic formulations for treatment of type 2 diabetes.

Clostridium difficile, often called "C. difficile" or "C. diff", is a bacterium that can cause symptoms ranging from diarrhea to life-threatening inflammation of the colon. The methods, compositions, systems and kits of the present disclosure provide for a diagnostic assay of at least one microbiome that includes a report that gives guidance on health status or treatment modalities for infections such as C. difficile. The present disclosure also provides therapeutic or cosmetic formulations for treatment of Clostridium difficile infections.

Asthma is a condition in which the airways narrow and swell and produce extra mucus. This can make breathing difficult and trigger coughing, wheezing and shortness of breath. The methods, compositions, systems and kits of the present disclosure provide for a diagnostic assay of at least one microbiome that includes a report that gives guidance on health status or treatment modalities for asthma. The present disclosure also provides therapeutic or cosmetic formulations for treatment of asthma.

Autism spectrum disorder is a serious neurodevelopmental disorder that impairs a child's ability to communicate and interact with others. It also includes restricted repetitive behaviors, interests and activities. Autism spectrum disorder (ASD) is now defined by the American Psychiatric Association's Diagnosis and Statistical Manual of Mental Disorders (DSM-5) as a single disorder that includes disorders that were previously considered separate—autism, Asperger's syndrome, childhood disintegrative disorder and pervasive developmental disorder not otherwise specified. The methods, compositions, systems and kits of the present disclosure provide for a diagnostic assay of at least one microbiome that includes a report that gives guidance on health status or treatment modalities for autism spectrum disorder. The present disclosure also provides therapeutic or cosmetic formulations for treatment of autism spectrum disorders.

Psoriasis is a common, persistent, long-lasting (chronic) skin condition that changes the life cycle of skin cells. Psoriasis causes cells to build up rapidly on the surface of the skin. The extra skin cells form thick, silvery scales and itchy, dry, red patches that are sometimes painful. The methods, compositions, systems and kits of the present disclosure provide for a diagnostic assay of at least one microbiome that includes a report that gives guidance on health status or treatment modalities for Psoriasis. The present disclosure also provides therapeutic or cosmetic formulations for treatment of psoriasis or a similar skin condition.

Allergies occur when the immune system reacts to a foreign substance such as pollen, bee venom or pet dander. When you come into contact with the allergen, the immune system's reaction can inflame the skin, sinuses, airways or digestive system. The methods, compositions, systems and kits of the present disclosure provide for a diagnostic assay of at least one microbiome that includes a report that gives guidance on health status or treatment modalities for allergies. The present disclosure also provides therapeutic or cosmetic formulations for treatment of allergies.

Cardiovascular diseases can affect the heart, arteries and veins of the body. Examples of some cardiovascular disease include but are not limited to heart valve disease, coronary artery disease, congenital heart disease in adults and congenital heart spontaneous coronary artery dissection, heart failure, heart rhythm disorders (arrhythmias). The methods, compositions, systems and kits of the present disclosure provide for a diagnostic assay of at least one microbiome that includes a report that gives guidance on health status or treatment modalities for cardiovascular disease. The present disclosure also provides therapeutic or cosmetic formulations for treatment of the above-mentioned cardiovascular conditions.

Cancer refers to any one of a large number of proliferative diseases characterized by the development of abnormal cells that divide uncontrollably and have the ability to infiltrate and destroy normal body tissues and organs. The methods, compositions, systems and kits of the present disclosure provide for a diagnostic assay of at least one microbiome that includes a report that gives guidance on health status or treatment modalities for cancer or other proliferative diseases. The present disclosure also provides therapeutic or cosmetic formulations for treatment of cancer.

Depression also called major depression, major depressive disorder or clinical depression is a mood disorder that causes a persistent feeling of sadness and loss of interest. It can affect how a person feels, thinks and behaves and can lead to a variety of emotional and physical problems. The methods, compositions, systems and kits of the present disclosure provide for a diagnostic assay of at least one microbiome that includes a report that gives guidance on health status or treatment modalities for depression disorders. The present disclosure also provides therapeutic or cosmetic formulations for treatment of the above-mentioned depression conditions.

Cystic fibrosis is a life-threatening genetic disorder that causes severe damage to the lungs and digestive system. Cystic fibrosis affects the cells that produce secreted fluids such as mucus, sweat and digestive juices that act as lubricants in the body. These secreted fluids are normally thin and slippery but in cystic fibrosis the secretions to become thick and sticky resulting in plugging up tubes, ducts and passageways, especially in the lungs and pancreas. The methods, compositions, systems and kits of the present disclosure provide for a diagnostic assay of at least one microbiome that includes a report that gives guidance on health status or treatment modalities for cystic fibrosis. The present disclosure also provides therapeutic or cosmetic formulations for treatment of cystic fibrosis.

Multiple sclerosis is a disease in which the immune system attacks the protective sheath (myelin) that covers the nerves. Myelin damage disrupts communication between the brain and the rest of the body. Ultimately, the nerves themselves may deteriorate a process that's currently irreversible. The methods, compositions, systems and kits of the present disclosure provide for a diagnostic assay of at least one microbiome that includes a report that gives guidance on health status or treatment modalities for multiple sclerosis. The present disclosure also provides therapeutic or cosmetic formulations for treatment of multiple sclerosis.

Urinary tract infection is an infection in any part of the urinary system (e.g. kidneys, ureters, bladder and urethra). Most infections involve the lower urinary tract—the bladder and the urethra. Infection limited to the bladder can be painful and annoying. However, serious consequences can occur if a UTI spreads to the kidneys. The methods, compositions, systems and kits of the present disclosure provide for a diagnostic assay of at least one microbiome that includes a report that gives guidance on health status or treatment modalities for urinary tract infections. The present disclosure also provides therapeutic or cosmetic formulations for treatment of infections in any part of the urinary system.

Radiation enteropathy is radiation-induced GI injuries of the colon and rectum to the small bowel. Radiotherapy is a mainstay of oncological treatment for a variety of malignant diseases and is commonly administered to the abdomen and pelvis of patients with gastrointestinal (GI), urological and gynaecological cancers. The methods, compositions, systems and kits of the present disclosure provide for a diagnostic assay of at least one microbiome that includes a report that gives guidance on health status or treatment modalities for radiation enteropathy. The present disclosure also provides therapeutic or cosmetic formulations for treatment of radiation-induced injury conditions.

Drug metabolism refers to the rate at which the body breaks down as drug after administration. The methods, compositions, systems and kits of the present disclosure provide for a diagnostic assay of at least one microbiome that includes a report that gives guidance on health status or treatment modalities for drug metabolism in a patient. The present disclosure also provides therapeutic or cosmetic formulations for treatment of drug metabolism conditions.

Chronic fatigue syndrome is a complicated disorder characterized by extreme fatigue that can't be explained by any underlying medical condition. The fatigue may worsen with physical or mental activity, but doesn't improve with rest. The cause of chronic fatigue syndrome is currently unknown. The methods, compositions, systems and kits of the present disclosure provide for a diagnostic assay of at least one microbiome that includes a report that gives guidance on health status or treatment modalities for chronic fatigue syndrome. The present disclosure also provides therapeutic or cosmetic formulations for treatment of CFS conditions.

Type 1 diabetes, once known as juvenile diabetes or insulin-dependent diabetes, is a chronic condition in which the pancreas produces little or no insulin, a hormone needed to allow sugar (glucose) to enter cells to produce energy. Various factors may contribute to type 1diabetes, including genetics and exposure to certain viruses. Although type 1 diabetes typically appears during childhood or adolescence, it also can develop in adults. The methods, compositions, systems and kits of the present disclosure provide for a diagnostic assay of at least one microbiome that includes a report that gives guidance on health status or treatment modalities for type 1 diabetes. The present disclosure also provides therapeutic or cosmetic formulations for treatment of type 1 diabetes.

Dental cavities are caused by the conversion of sugar from food to elongated, sticky sugar chains through a bacterially produced glucansucrase enzyme. Attempts to directly inhibit this enzyme have failed because it is evolutionarily closely related to amylase, which is the enzyme used to break down starch. A more effective approach would be to reduce the proportion of *Streptococcus mutans*, which is the bacteria associated with tooth decay. This would leave intact the useful enzymes used by the body to break down starches while simultaneously minimizing the rate of cavity formation. The methods, compositions, systems and kits of the present disclosure provide for a diagnostic assay of at least one microbiome that includes a report that gives guidance on health status or treatment modalities for tooth decay. The present disclosure also provides provides therapeutic or cosmetic formulations for treatment of tooth decay conditions.

Halitosis is a dental condition in which excessively bad breath is produced by the microbial flora present in an individual's mouth. It is known that the most problematic types are the gram-negative bacteria (e.g. *Prevotella intermedia, Porphyromonas gingivalis, Treponema denticola*). By using the methods outlined in this disclosure, a strain level list of the most problematic bacteria, as well as the most protective, will enable a directed therapeutic/cosmetic formulation to treat halitosis. The methods, compositions, systems and kits of the present disclosure provide for a diagnostic assay of at least one microbiome that includes a report that gives guidance on health status or treatment modalities for halitosis. The present disclosure also provides therapeutic or cosmetic formulations for treatment of halitosis.

VII. Examples

Example 1: Comparison of Microbe Classification Accuracy

As more bacterial strains are identified, it has become clear that just sequencing a few of the hypervariable regions does not provide enough distinction. There are classes of bacteria now characterized that share homologous hypervariable regions. Therefore, the need to sequence the entire 16S and/or 23S and include all of the hypervariable regions is necessary to make accurate classification calls. Comparison simulations experiments were conducted with the methods of the present disclosure and the current methods in the field to determine if the methods of the present disclosure provide increased accuracy for microbe classification.

Using long read length sequence coverage of the 16S and/or 23S ribosomal subunits, allows for each sequence read yield an unambiguous assignment of bacterial identification. The current shorter read length platforms, covers only 1-3 hypervariable regions FIG. 2A. These shorter read length platforms are currently performing at, or below, a 60-80% classification accuracy. A read length that can span the entirety of the 16S operon will perform at a 90-99% classification accuracy FIG. 2B. The plot shown in FIG. 2B presents classification accuracy based upon sequencing shorter hyper-variable regions (lower lines) vs. sequencing the entire 16S subunit in a single sequence read (upper line). The plots are produced using calculations derived from data from the Ribosomal Database Project. Moreover, even accounting for higher error rates in certain longer read sequencing technologies still yields substantially better classification accuracy. By extension, sequencing the entirety of the ribosomal RNA operon (rRNA that includes—16S, intergenic, and 23S regions) would increase the classification capability of the method.

Example 2: Affect of Diet on a Subject's Gut Microbiome and Obesity (Prophetic Example)

Figure 3:
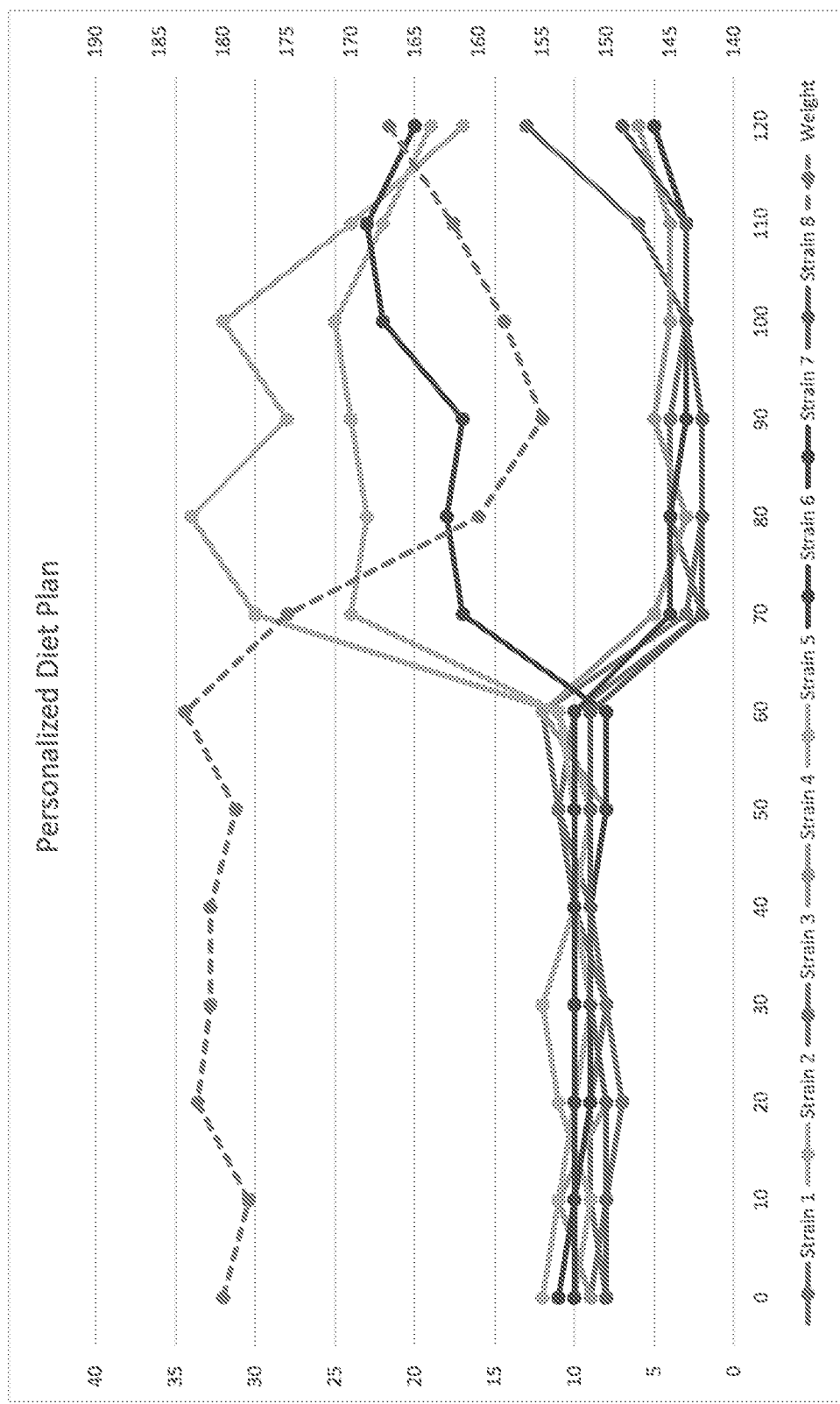
FIG. 3 depicts changes in an individual's gut microbiome profile to changes in diet. In this example, the change in weight (dashed line) is a lagging indicator, when compared to the change in the microbiome structure. Subject-specific diet recommendation can be based on quantitative microbiome signatures.

Using the methods provided herein, experiments were conducted to determine if a particular diet regimen can changes a subjects' gut microbiome profile. FIG. 3 depicts changes measured and detected in an individual's gut microbiome profile to changes in diet using the methods described herein. Weight (dashed line) is a lagging indicator, when compared to the change in the microbiome structure.

A report containing individualized dieting recommendation was generated based on quantitative microbiome profile using the computer system shown in FIG. 1 was provided to a healthcare professional.

Example 3: Comparison of Microbe Resolution at Strain Level of a Microbiome

Comparison simulation experiments were conducted with the methods of the present disclosure to determine if the methods of the present disclosure provide increased microbe classification accuracy at the strain level compared to the current methods being used in the field.

Samples were collected in the form of skin swabs. Briefly, a sterile swab is first dipped into a tube containing sterile 1xPBS to wet; the swab was then swiped across the area of interest 10-20 times; next the swab was gently dipped into 300 uL of lysis buffer (described herein) in a sterile 1.5 mL tube; and the swab is left in the microcentrifuge tube until nucleic acid extraction. The subsequent extraction of DNA from human skin microbiome samples includes the removal of the exonuclease was conducted followed by adapter ligation at various higher concentrations. Next, size-selection using Ampure and Blue Pippen approaches were performed to enrich for the expected length amplicon species. After extraction, the nucleic acid samples were selected for the proper size. Next, PCR amplification reactions were conducted to prepare the libraries for sequencing. Forward and reverse primers were selected based on empirical data that indicate which sets had minimal self-complimentarily. Finally samples were sequenced using long read length sequence technology.

Figure 4:
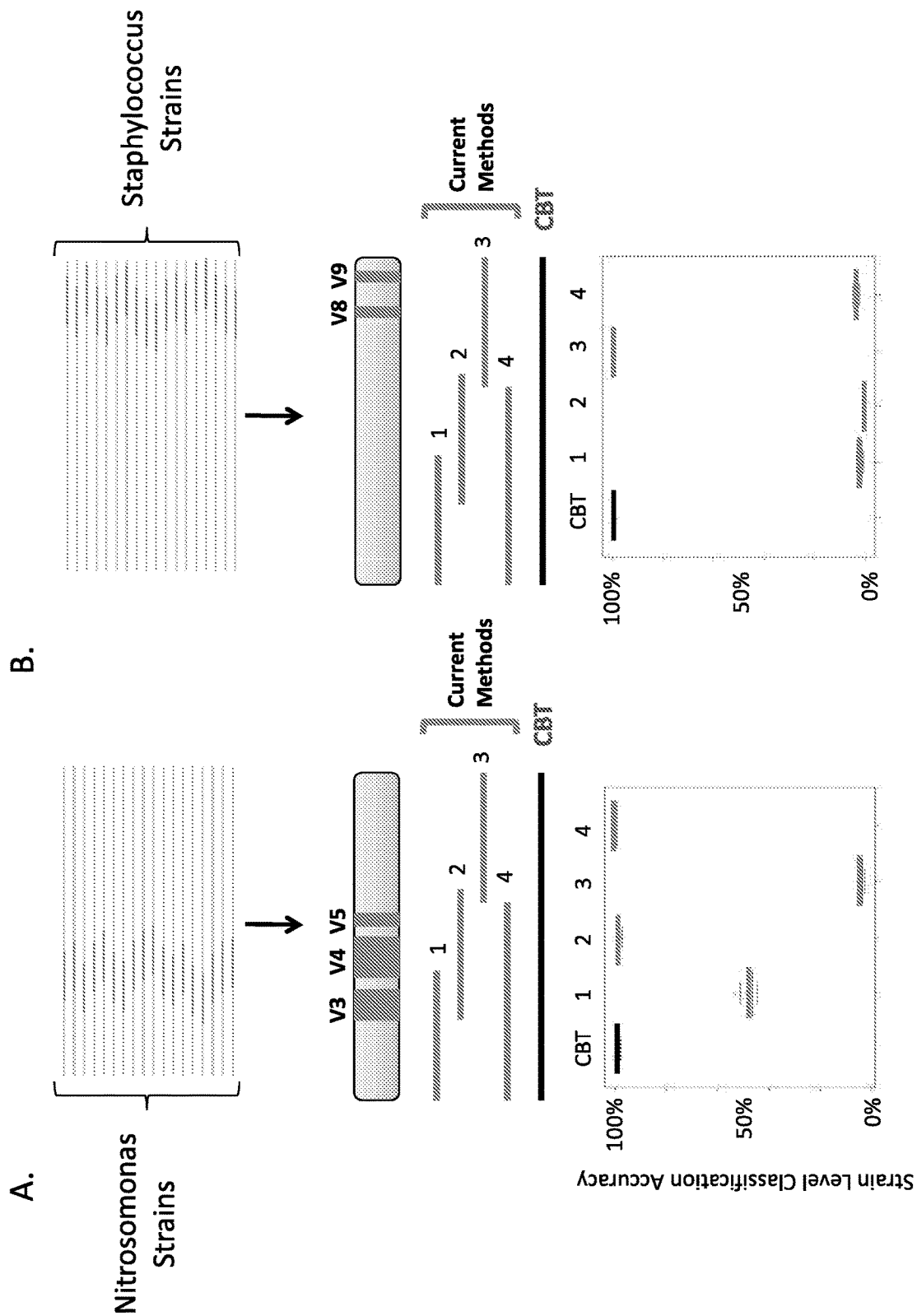
FIG. 4A-4B depict that different genera have different locations of variation that would allow one to distinguish strains. This means that utilizing methods in which only a portion of 16S is observed would intrinsically limit the strain level classification accuracy. The boxplots on the bottom have an X-axis that corresponds to the method utilized (CBT corresponds to the full length 16S amplicon), and a Y-axis that corresponds to the percentage strain classification accuracy achieved.

FIG. 4A depicts strain level resolution data with the methods provided for Nitrosomonas genus, percentage strain classification accuracy is shown in the Y-axis. FIG. 4B depicts strain level resolution data with the methods provided for Staphylococcus genus, percentage strain classification accuracy is shown in the Y-axis. FIG. 6A standard resolution of a microbiome using current technology FIG. 6B resolution of a microbiome using a method described herein.

Example 4: Study of Microbial-Based Therapeutic Application on Acne (Prophetic Example)

Experiments using the methods provided herein were conducted to determine if the application of Nitrosomonas to the skin can have beneficial effects on a person suffering from acne.

Samples were prepared for skin samples using the following steps a sterile swab is first dipped into a tube containing sterile 1xPBS to wet; the swab is swiped across the area of interest 10-20 times with enough vigor that the skin is slightly pink/red colored afterwards; the swab is gently dipped into 300 uL of Lysis Buffer (described below) in a sterile 1.5 mL tube; the swab is left in the microcentrifuge tube for shipping and then processed for nucleic acid extraction and long read sequence analysis using the methods provided herein.

Figure 5:
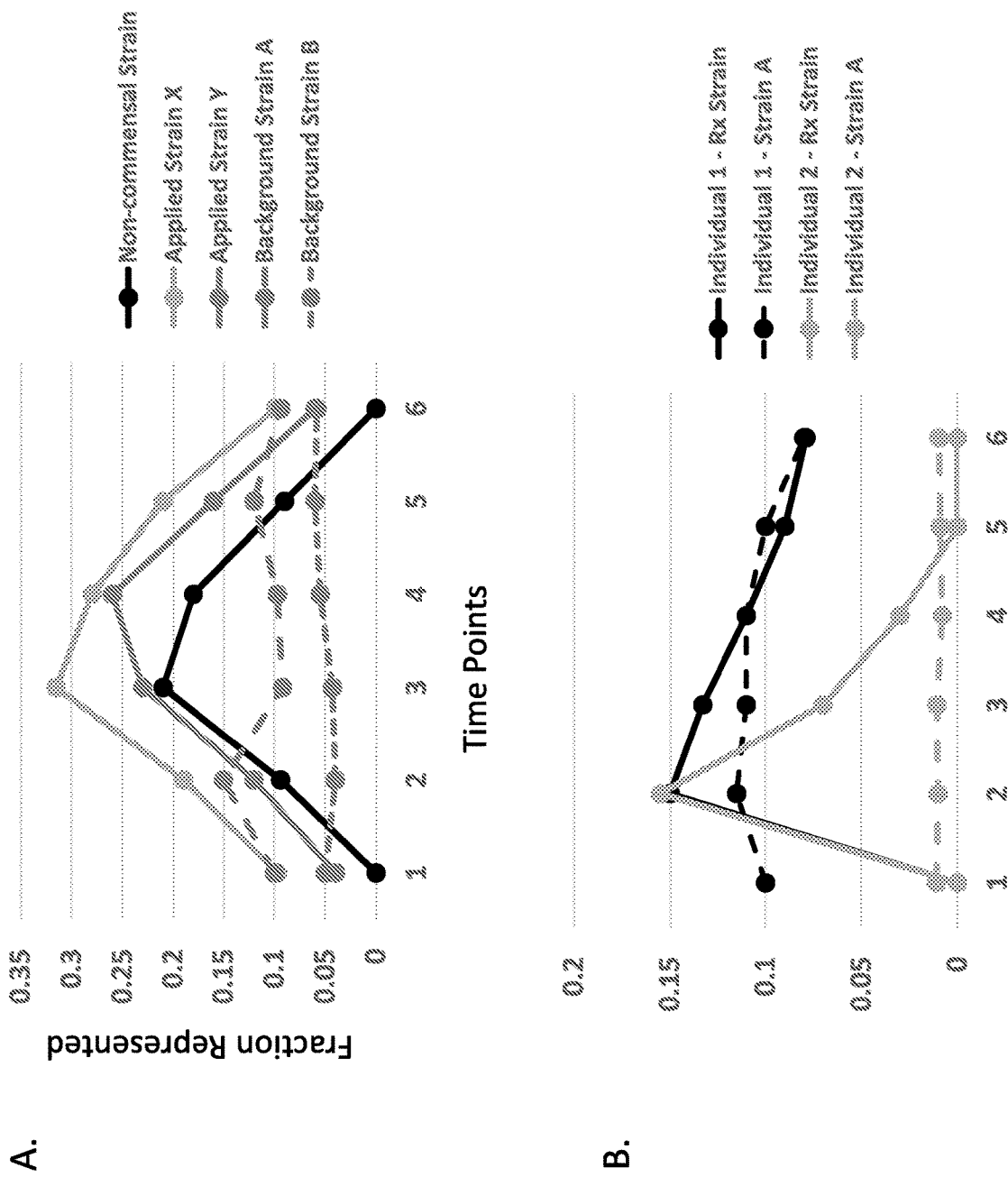
FIG. 5A-5B depict a study in which subjects (that include cases and controls for a specific indications as provided herein) apply a microbial therapeutic/cosmetic containing a consortia of strains.

FIG. 5A-5B depict expected results from the study FIG. 5A depicts how the methods of this disclosure can be used to quantify the successful application of the microbial therapeutic/cosmetic over time. The addition of a non-commensal strain to the consortia, aids in distinguishing applied strains from the background variation of individual microbiomes for that site (e.g. skin, gut, mouth, etc.) FIG. 5B depicts how the methods in this disclosure can be used to discover stabilizing commensal strains. Those strains that when present, are correlated to the longevity of the applied consortia, would become candidates for expanding the initial consortia to produce formulations with increased stability and efficacy

Example 5: Association Study with Disease and Healthy Controls Subjects (Prophetic Example)

Comparison experiments were conducted to determine to if the present methods of the disclosure provide more insights to correlation of a microbiome that can distinguish healthy from diseased microbiome profiles over traditional current methods.

Nucleic acids were extracted from biological samples from the human microbiome. Briefly, removal of the exonuclease was conducted followed by adapter ligation at various higher concentrations. Next, size-selection using Ampure and Blue Pippen approaches were performed to enrich for the expected length amplicon species (e.g. full length 16S is about 1500 bp). After the samples were selected for the proper size, amplification reactions were conducted to prepare the libraries for sequencing. Forward and reverse primers were selected based on empirical data that indicate which sets had minimal self-complimentarity. Finally samples were sequenced using long read length sequence technology.

Using the methods above we expect to identify at set of microbes in a microbiome that would distinguish healthy from diseased subjects. The following protocol, as provide herein, can be used to assess the differences between healthy from diseased individuals. Example of diseases that can be used with the methods described include IBD, preterm labor, obesity, diabetic foot ulcers, bacteremia, acne, infantile colic, type 2 diabetes, C. difficile, IBS, asthma, autism, psoriasis, allergies, cardiovascular disease, cancer, depression, cystic fibrosis, multiple sclerosis, urinary tract infection, radiation enteropathy, drug metabolism, chronic fatigue, type 1 diabetes, halitosis, and tooth decay.

Figure 7:
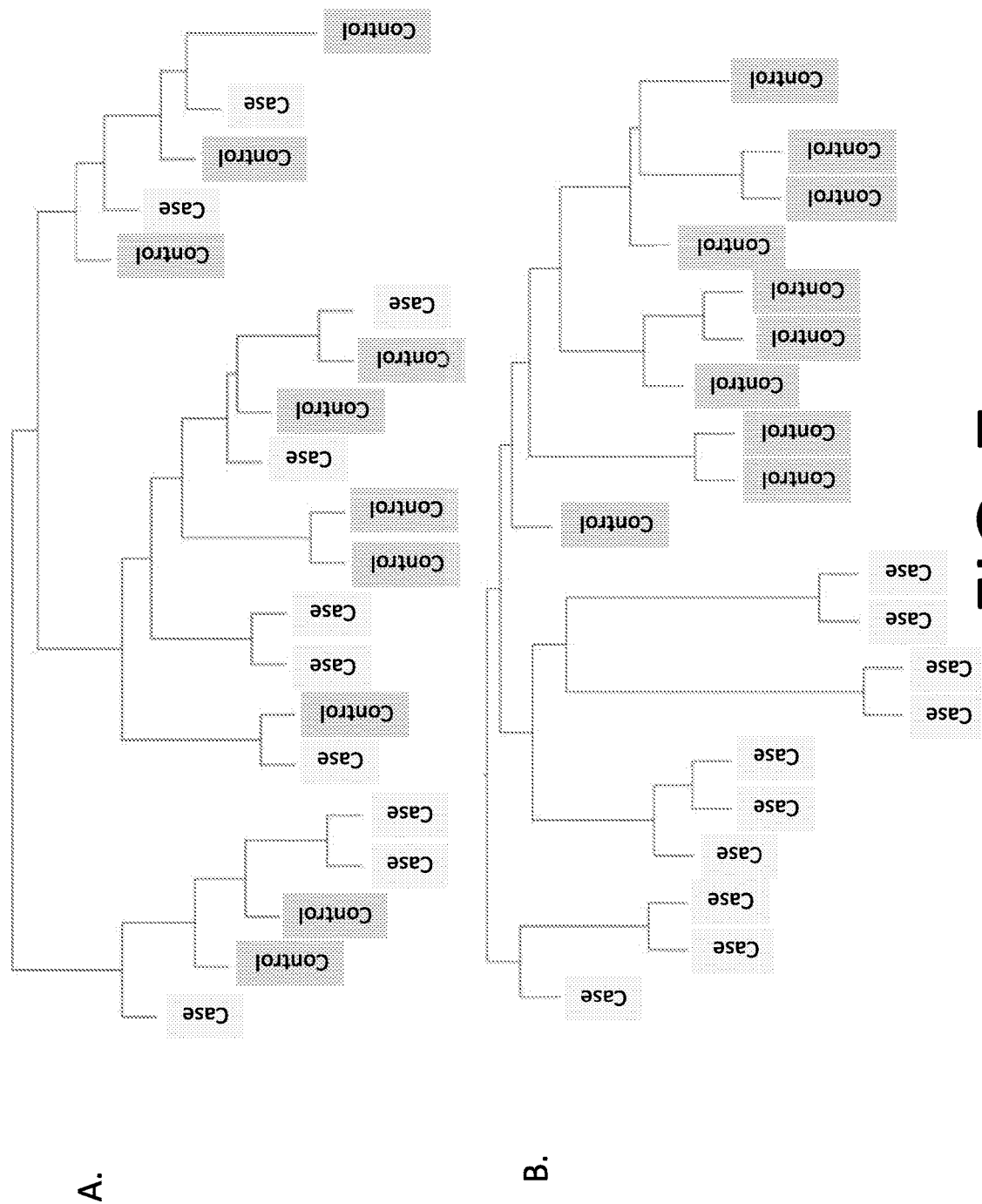
FIG. 7A depicts a prophetic example in which usage of the standard approaches currently being used for genus level resolution. The results indicate that the standard approaches do not separate disease cases from healthy controls because the variation at the strain level is masked
FIG. 7B depicts a prophetic example in which the disease cases are well separated from healthy controls using the methods provided herein.

FIG. 7A-7B show the expected results of the comparison association study. FIG. 7A depicts the expected results from an association study with a disease and healthy controls patients' microbiomes using current technology, indicating no obvious correlation of a microbiome profile with a disease state.

Figure 8:
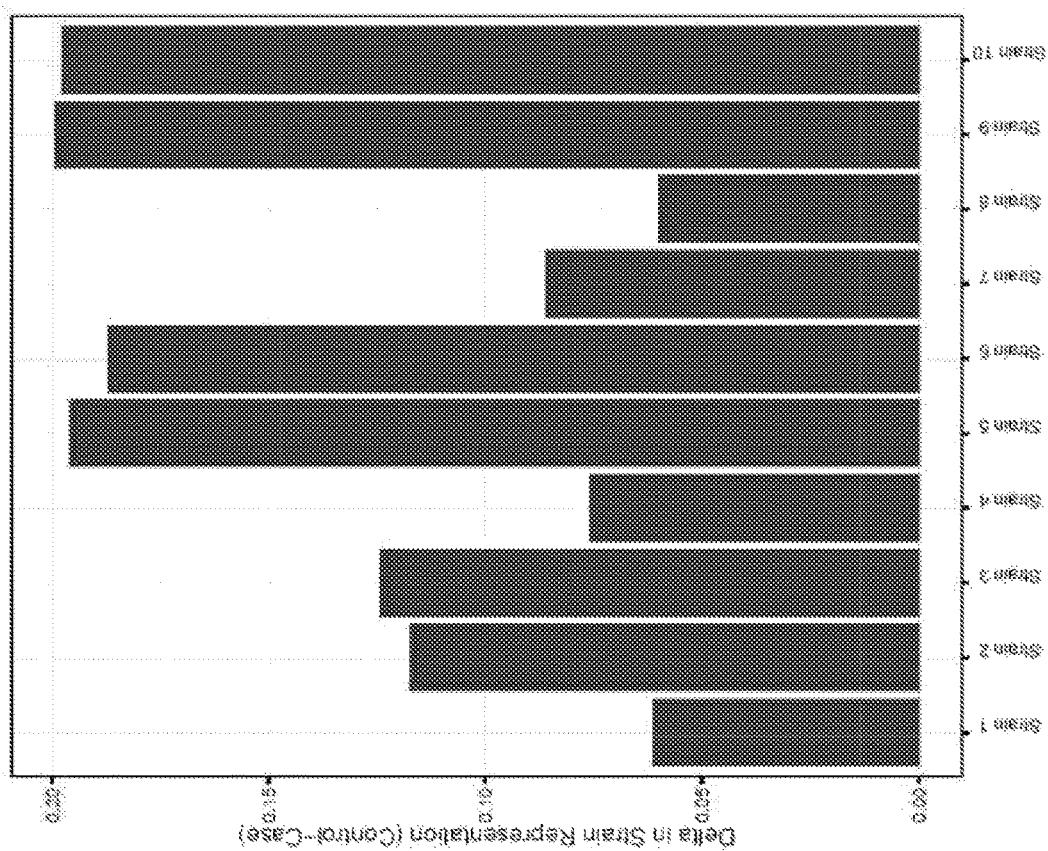
FIG. 8. depicts a top ten list of microbial strains responsible for the distinguishing of healthy control and disease subjects depicted in Example 5, FIG. 7B. This information can be used for diagnostics and therapeutics for this indication.

In contrast, FIG. 7B depicts the expected results from an association study with disease and healthy controls patients' microbiomes using a method described herein revealing a correlation of a microbiome that can distinguish healthy controls' microbiome profiles from disease subjects' microbiome profiles (as shown FIG. 8).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of profiling a microbiome by assaying a biological sample of a subject, the method comprising:
   (a) obtaining said biological sample from said subject, wherein said biological sample comprises a plurality of microbes, wherein said subject has or is suspected of having type 2 diabetes;
   (b) subjecting nucleic acid molecules extracted from said plurality of microbes to sequencing to obtain nucleic acid sequence reads that comprise ribosomal RNA operon sequences from said plurality of microbes, wherein at least one of said nucleic acid sequence reads provides a contiguous sequence spanning at least a 16S region of said ribosomal RNA operon, a 23 S region of said ribosomal RNA operon, or an intergenic region between said 16S region and said 23 S region of said ribosomal RNA operon;
   (c) aligning said nucleic acid sequence reads of said ribosomal RNA operon sequences to one or more reference sequences to identify said plurality of microbes at a strain level;
   (d) using a database to identify metabolic pathways that correspond said plurality of microbes identified at said strain level in (c); and
   (e) based on (d), administering a microbial-based composition to said subject, thereby treating said type 2 diabetes.

2. The method of claim 1, wherein at least one of said nucleic acid sequence reads comprises said contiguous sequence spanning at least said 16S region.

3. The method of claim 1, wherein at least one of said nucleic acid sequence reads comprises said contiguous sequence spanning at least said 23S region.

4. The method of claim 1, wherein at least one of said nucleic acid sequence reads comprises said contiguous sequence spanning said intergenic region between said 16S region and said 23S region of said ribosomal RNA operon.

5. The method of claim 1, wherein said plurality of microbes in said microbiome profile comprises 800 or fewer microbes.

6. The method of claim 1, further comprising obtaining said nucleic acid molecules from said plurality of microbes in biological samples taken at least at two different points of time.

7. The method of claim 1, wherein a presence or absence of said plurality of microbes and said metabolic pathways is indicative of said subject having said type 2 diabetes.

8. The method of claim 1, further comprising detecting or measuring an amount of said nucleic acid sequence reads of said plurality of microbes.

9. The method of claim 8, wherein said detecting or measuring said amount of said nucleic acid sequence reads of said plurality of microbes comprises detecting levels of markers from said plurality of microbes.

10. The method of claim 1, wherein at least one of said nucleic acid sequence reads provides a contiguous sequence spanning said 16S region and said 23 S region of said ribosomal RNA operon.

11. The method of claim 1, wherein each of said nucleic acid sequence reads is longer than 2000 bases.

12. The method of claim 1, wherein said sequencing of (b) is performed using a long read sequencing platform.

13. The method of claim 1, further comprising extracting said nucleic acid molecules from said plurality of microbes in said biological sample.

* * * * *

```
                         SEQUENCE LISTING

<160> NUMBER OF SEQ ID NOS: 645

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 1
tgatatgtag cacgta                                                    16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 2
gtgatgtatc tgctcg                                                    16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 3
tcacagtagt cgcgag                                                    16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 4
tctatctctc atcgcg                                                    16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 5
tcgtgcgcac acactg                                                    16

<210> SEQ ID NO 6
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      barcode oligonucleotide

<400> SEQUENCE: 6
gatacacgca gatgct                                                    16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 7
catagtctat agagat                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 8
gcgactctga gtacac                                                    16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 9
cgacgcgcgc gactgc                                                    16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 10
actcgtagtg tgtcat                                                    16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 11
tatgcgtcag atcaga                                                    16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
``` barcode oligonucleotide

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 12
ctgcatgcac gtgtac                                                    16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 13
acgtgagaga cgcatc                                                    16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 14
atcacacatc acacat                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 15
agctcgctct ctctga                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      barcode oligonucleotide

<400> SEQUENCE: 16
cgagatatat gatgcg                                                    16

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagtttgat cctggctcag                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 18
agagtttgat catggctcag                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agagtttgat cctggcttag                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agaatttgat cttggttcag                                               20

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaggaggtga tccagcc                                                  17

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acggttacct tgttacgact t                                             21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acggctacct tgttacgact t                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 24
acggatacct tgttacgact t                                              21

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cygaatgggg vaacc                                                     15

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tactdagatg tttcasttc                                                 19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctttccctc acggtact                                                  18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgacatcgag gtgccaaac                                                 19

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gccaaggcat ccacc                                                     15

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacgtctttc atcgsct                                                   17

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcgatttcyg aaygggraaa ccc                                            23

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgaatgggg vaaggg                                                    16

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccttgcccca ttcgg                                                     15

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggaactgaaa catctaagta                                                20

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
kttcgctcgc crctac                                                    16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agtagyggcg agcgaa                                              16

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggtactggt tcactatcgg                                          20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttcgcctttc cctcacggta ct                                       22

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agtaccgyga gggaaag                                             17

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cattmtacaa aaggyacgc                                           19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cattmtrcaa aaggyacgc                                           19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttcggrgaga acsagmta                                            18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tagctggttc tcyycgaa                                                 18

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctgggytgt tyccct                                                   16

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggatgttggc ttagaagcag                                               20

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttggcttrg argcagc                                                  17

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
rgtgagctrt tacgc                                                    15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
wgcgtaayag ctcac                                                    15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtagrrgag cgttc                                                    15

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other

<400> SEQUENCE: 50
gaggccgana rgcgta                                                   16

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggacaacagg ttaatattcc                                               20

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaaccgwcac aggtrg                                                   16

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggggccattt tgccgagttc                                               20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccttmtcscg aasttacgg                                                19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cttaggaccg ttatagttac                                               20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgacaaggaa tttcgctac                                                19

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gacgyaaaga ccccrtg                                                  17

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
accgccccag thaaact                                                  17

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tcgctcaacg gataaaag                                                 18

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gagycgacat cgagg                                                      15

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cgacgttctg aacccagctc                                                 20

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aramcgtcgt gagacag                                                    17

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agtacgagag gaccgg                                                     16

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cttagatgcy ttcagc                                                     16

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gyttagatgc yttc                                                       14

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cccgcttaga tgctttcagc                                                 20

```
<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ytgaargcat ctaa                                                         14

<210> SEQ ID NO 68
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68 ctgaag                                                                   6

<210> SEQ ID NO 69
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69 gaagac                                                                   6

<210> SEQ ID NO 70
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 cctcagc                                                                  7

<210> SEQ ID NO 71
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71 ccatc                                                                    5

<210> SEQ ID NO 72
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72 ctggag                                                                   6
```

```
<210> SEQ ID NO 73
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73 cttgag                                                                    6

<210> SEQ ID NO 74
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74 cccagc                                                                    6

<210> SEQ ID NO 75
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75 cgtctc                                                                    6

<210> SEQ ID NO 76
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 acctgc                                                                    6

<210> SEQ ID NO 77
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 cacgag                                                                    6

<210> SEQ ID NO 78
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 gcagtg                                                                    6
```

```
<210> SEQ ID NO 79
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79 ctcttc                                                                     6

<210> SEQ ID NO 80
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 cccgc                                                                      5

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tagggataac agggtaat                                                       18

<210> SEQ ID NO 82
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 gaaga                                                                      5

<210> SEQ ID NO 83
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 gccgag                                                                     6

<210> SEQ ID NO 84
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84 gcggccgc                                                                   8

<210> SEQ ID NO 85
```

```
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85 gctcttc                                                                    7

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tggcaaacag ctattatggg tattatgggt                                           30

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtcgaacggt macargaaga                                                      20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
grtcatggct cagattgaac                                                      20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
attgaacgct ggcggcaggc                                                      20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acatgcaagt cgaacggtaa                                                      20

<210> SEQ ID NO 91
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atcatggctc agattgracg                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
attgaagagt ktgatcatgg                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
catggctcag attgaamgct                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tcgaacggyw acaggaagaa                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgctgkcgg caggcctaac                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctmtttgctg acgagtggcg                                              20

<210> SEQ ID NO 97
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 97
acggtwacwg gaagaagctt                                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tgaacgctgg cggcaggcct                                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ctgacgagtg gcgsacgggt                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
atrcaagtcg aacggtaaca                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gagtttgayc atggctcaga                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cggcaggcct aacacatgca                                                    20

<210> SEQ ID NO 103
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 103
catggmycag attkaaygct                                                  20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
aacgctggcg gcaggcctaa                                                  20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aagcttgskc tttgctgacg                                                  20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cttgctcttt kctgacgagt                                                  20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gctygctctt tgctgacgag                                                  20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
aaattgaagw gtttgatcat                                                  20

<210> SEQ ID NO 109
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 109
gagtggcgra cgggtgagta                                                  20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
atgcaagtcg aacggtaaca                                                  20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gtcgaacggt aacaggwaga                                                  20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tggctcagat tgmacgctgg                                                  20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gctgacgagt ggcggacggg                                                  20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ctttgctgac gagkggcgga                                                  20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 115
aagaagcttg ctctttgctg                                                 20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gaagaagctt gctctttgct                                                 20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tttgatcatg gctmagattg                                                 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cgagtgscgg acgggtgagt                                                 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
mgtggcggac gggtgrgtaa                                                 20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agaagcttgc tctttgctgm                                                 20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gctgacgagt ggcggwcggg         20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ctctttgctg acgagtggcg         20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ttgctgacga gtggcggacg         20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctcagattga acrctggcgg         20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gcttgctcyt tgctgacgag         20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ttgctcttwg ctgacgagtg         20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
rgcttgctct ttgctgacga                                           20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
kggcggcagg sctaacacat                                           20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aggaagaagc ttgctctttg                                           20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tttgatcatg gctcagattg                                           20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acacatscaa gtcgaacggt                                           20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ttgctctttg ctgacgrgtg                                           20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
aagragcttg ctctttgctg                                                20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ctttgctgac gagtggcgga                                                20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cmagtcgaac ggtaacagga                                                20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
aagagtttga tcatggctca                                                20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtaacaggaa gaagcttgct                                                20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
saagtcgaac ggtaacmrga                                                20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
caggaagaag cttgctcttt                                        20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cwgacgagtg gcggacgggk                                        20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
aagtcgwamg gtaacaggaa                                        20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gastggcgga cgggtgagta                                        20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gytgasgagt ggcggacggg                                        20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gcagscctaa cacatgcaag                                        20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tctttgctga cgagtrgcgg                                        20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ctaacacatg caagtcgaac                                           20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gatcawggct cagattgaac                                           20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
atcatggctc rgattgaacg                                           20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgaacggtaa caggaagaag                                           20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tcatggctcw gattgaacgs                                           20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
agaagcttgc tctttgctga                                           20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
catgyaagtc gaacggtaam                                                 20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagartttga tcatgkctca                                                 20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cacatgcaag tcgaacggwa                                                 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
aacggtaaca sgaagaagct                                                 20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gtcgaacggt aacaggaara                                                 20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gagtttgatc atgkctcaga                                                 20

```
<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
caagtcraac ggtaacagga                                               20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gcctaacaca tgcaagtcga                                               20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
aygcargtcg aacggtaaca                                               20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
sagattgaac gctggcggca                                               20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gattgaacsc tggyggcmgg                                               20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
acgagtggcg gacgggtgag                                               20

<210> SEQ ID NO 164
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
gaagagtttg atcatggctm                                              20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
tcgaackgta acaggaagaa                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
ggcaggccta acacatkcaa                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
catggctcag attgaacgct                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
tggctcagat tgaacgctgg                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
gaagcttgct ctttgctgac                                              20

<210> SEQ ID NO 170
<211> LENGTH: 20

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gkctcagatt gaacgctggc                                                    20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gctggcggca ggcctaacac                                                    20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ggmctwacac atgcragtcg                                                    20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
crstggcggc aggcctaaca                                                    20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
aggmagaagc ttgctcttwg                                                    20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
caagtcgaac ggtaacagga                                                    20

<210> SEQ ID NO 176
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 176
mgcttgctct ttgctgacga                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
traagagttt gatyatggct                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
agtcgaacgg tamcagraag                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acacatgcaa gtygaacggt                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
aagycgaacg rtaacrggaa                                              20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctaagcgyac acggtggatg                                              20

<210> SEQ ID NO 182
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 182
tcggtaaggt gatatgaacc                                              20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccctggsagt cagaggcgat                                              20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
atgaaccgtt ataaccggcg                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cagtcagagg cgatgaagga                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cygttataac cggsgatttc                                              20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
agcgacwaag cgtacacggt                                              20

<210> SEQ ID NO 188
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 188
ycagaggcga tgaaggacgt                                              20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
taatcygcga taagcgtcsg                                              20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgakatgaac cgttataacc                                              20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cacggtkkat gccctggcag                                              20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gcgtacacgg tggatgccct                                              20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
taagcgtcgg waaggtgata                                              20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
ywcacggtgg atgccctggc                                              20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ggcagtcaga ggcgatgaag                                              20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcggtaagg tgatatgawc                                              20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
aggtgatatg aaccgttatr                                              20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
wggcagtcag aggcgatraa                                              20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cggtggatgc cctggcagtc                                              20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 200
ttataaccgg cgatttcyga                                              20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gcgtcggtaa ggtgatatga                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
accgttataa ccggcgattt                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tmatctgcga taagcgtcgg                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gcgtacacgg tggrtgccct                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tcagaggcga tgaaggacgt                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 206
tamgcgtcgg taargtkata                                              20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
atatgaaccg ttataaccgg                                              20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tatarccggc gatttccgaa                                              20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tataaccggc gatttccgaa                                              20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
taargtgata tgaaccgkta                                              20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgccctggca gtcagaggcg                                              20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tmaggtgata tsaaccrtta                                         20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gttargcgac taagcgtaca                                         20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tatgraccgt tataaccgrc                                         20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cagtcagagg cgrtgaagsa                                         20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
cagaggcgat gaaggacgtg                                         20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
atgccctggc agtcasaggc                                         20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atctgcgata agcgtcggta                                          20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
aggacgtgct aatctgcgat                                          20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
tctgcgataa gygtcggtaa                                          20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
cgactaagcr tacacggtgg                                          20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ggcagtcaka ggsgawgaag                                          20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cgactaagcg twcacggtgg                                          20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
taaggtgaka tgaaccgtka                                          20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ccctggcagt cagaggcgat                                          20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ggtaakgtga katgaaccgt                                          20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ttataaccgg cgatttccgr                                          20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
gaaccgttat aaccggcgrt                                          20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gtgctaatct gcgataagcg                                          20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
cacggtggat gccctggcag                                          20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cgactaagcg tacrcgstgg                                              20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
acggyggatg cmctggcagt                                              20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
atgaaggacg tgctamyctg                                              20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
aagygtacac ggtggatgcc                                              20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgaaggacgt gctaatctgc                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
rttaagcgac tmagcgtaca                                              20

```
<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gtgatatgaa ccgttataac                                               20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
agcgactaar cgtacacggt                                               20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
aaccgttata accggcgatt                                               20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gtacacggtg gatgccctgg                                               20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ggttaagcsa ctaagcgtac                                               20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
tgcgataagc gtcggtaagg                                               20

<210> SEQ ID NO 243
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
aaggacgtkc taatctgcga          20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
gatgccctgg magtcakagg          20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
atgaaggacg tgcyaatctg          20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
atgccctggc agtcagaggc          20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 247
gtgatatsaa scgttataac          20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 248
ccgttayaac cggcgatttc          20

<210> SEQ ID NO 249
<211> LENGTH: 20

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gtgctaatct gcgataakcg                                                 20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
aagrwcgtgs taatctgcga                                                 20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
aatctgcgat aagcgtcggt                                                 20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
ygataagcgt cggtaaggtg                                                 20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
gaaccgttat aaccggcgat                                                 20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gataascgkc ggtaaggwga                                                 20

<210> SEQ ID NO 255
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 255
gytaatctgc gataagcgyc                                                 20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
sgtcggtaag gtgatatgaa                                                 20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tgaaccgtta taaccggcga                                                 20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gtgcyratct gcgataagcs                                                 20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ctgsgakaag cgtcggtaag                                                 20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tgcgataagc gtcggtaarg                                                 20

<210> SEQ ID NO 261
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 261
tggcagtcag aggcgatgra                                               20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
gatgaaggac gtgctaatct                                               20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
mgmggcgatg aaggacgygc                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
ctggcagtca gaggcgatga                                               20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
tgaaggamgt gctaatctgm                                               20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gaggcgatga aggacgtgct                                               20

<210> SEQ ID NO 267
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 267
ataagcgtcr gtaaggtgat                                                20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ggatgccctg gcagtcagag                                                20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ggtwaggtga tatgaaccrt                                                20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
caccatggga gtgggttgca                                                20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
tgactggggt gaagtcgtaa                                                20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
cyttgtgatt catgactrgg                                                20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 273
tcacaccatg ggagtgggtt                                           20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
ggtagcttaa ccttcgggag                                           20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ggagggcgct taccactttg                                           20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
tgggagtggg ttgcaaaaga                                           20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
gagtgggttg craaagwagt                                           20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gackggggtg aagtcgtwac                                           20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
cacaccatrg gaktgggktr                                          20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
tmgtaacaag gtaaccgtag                                          20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tagcttaacc ttcgggaggg                                          20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
rccactttrt gattcatgac                                          20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ccatgggagt gggttgcaaw                                          20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
gagwgggttg caaaagaagt                                          20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 285
cccgtcacac catggsagtg                                                 20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gggtgaagtc gtaacaaggt                                                 20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
aagaagtagg tagcttwacc                                                 20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
camcatggga gtgrgtygca                                                 20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
aagtaggtag cttaaccttc                                                 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
acaccatggg agtgggttgc                                                 20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
```

-continued ggagtgggtt gcaaaagaag                                      20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
sgagggcgst taccactttg                                      20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
atgggagtsg gttgcaaaag                                      20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
gtaacaaggt aaccgtaggg                                      20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
gattcatgac tggggtraag                                      20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
tgggttgcra aagaagtagg                                      20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
acaaggtaac cgtaggggaa                                              20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
ccatgggagt gggttgcaaa                                              20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gcttaacctt cgggagggcg                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
gaagtcrtaa caaggtracc                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
ttwccacttt gtgattcatg                                              20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaty catgactggg                                              20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
catkactggg gtgaagtsgt                                              20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tgtgaytcat gactggggtg                                              20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
agtcgtaaca aggtaaccgt                                              20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
tgattcatga ctggggtkaa                                              20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tgtgattcat gactkgggtg                                              20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
ccwckttgtg atwcatgact                                              20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
gtcacaccat gggagtgggw                                              20

```
<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tagctkaacc ttcgggaggg                                                   20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gcttaccact ttgtgattca                                                   20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
ttgtgattca tgactggggt                                                   20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
kttgcaaaag aagtaggtag                                                   20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
waagaagtag gtarctyaac                                                   20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
taccactkts tgattcatga                                                   20
```

```
<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
ccgtcacacs atgggagtgg                                                 20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gtaacaaggw aaycgtaggg                                                 20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
rcaaggtaam cgtagggga                                                  20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ggrgggcgct kascactttg                                                 20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ytcatgactg gggtgaagtc                                                 20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cttcrkgakg gsgcktacca                                                 20

<210> SEQ ID NO 322
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
taccactttg trattcatga                                              20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gtasctwaac cttsgggagg                                              20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
ggggtgaagw cgtaacaagg                                              20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
aaaagragta ggtagcttaa                                              20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
attcatgact ggggtgaagt                                              20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
rgaagtaggt rgcttaacct                                              20

<210> SEQ ID NO 328
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
tagcttaacc ttcggsaggk                                              20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gactggggwg aagtcgtaac                                              20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
cttaaccttm gggagggcgc                                              20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gactggggtg aagtcgtaac                                              20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gtaggtagct taaccttcgg                                              20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
gggcgcttac cmctttgtga                                              20

<210> SEQ ID NO 334
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 334
aagtagrtag cttaacsttc                                              20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
actgkggtga wgtcgtaaca                                              20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
tgattcatga ctggggtgaa                                              20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
wtgcaaaaga astaggtagc                                              20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
actttgtgat tcatgactgg                                              20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gttgcaaaag aagtaggtag                                              20

<210> SEQ ID NO 340
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 340
gagggcgctt accactttgt                                                 20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gggmgctyac cactttgtga                                                 20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ttaaccttcg ggasggcgct                                                 20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
tgactggggt gaagtcktaa                                                 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tgrgtwgyaa magaagtagg                                                 20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
gtaggtagct traccttcgg                                                 20

<210> SEQ ID NO 346
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 346 gggtgaagt cgtaacaagg                                                  20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
gggttgcaaa agaagyaggt                                                 20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
ttgtgattca kkactggrgy                                                 20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gcgcttacca ctttgygatt                                                 20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
cttaaysttc gggasggcgc                                                 20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
atgggagtgg sttgcaaaag                                                 20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
primer

<400> SEQUENCE: 352
taacaaggta accgtagggg                                            20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
gtcgtaacaa ggyaaccgta                                            20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
aagaagtagg tagcttaasc                                            20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
cacaccatgg gagtgggttg                                            20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
cgtcacacca tgggagtggg                                            20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
ttcatgacyg gggtgaagtc                                            20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 358
agcttawccy tcgggagggs                                              20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
ggtagcttar ccttcgggag                                              20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
gggttgcaaa agaagtaggt                                              20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
tcatgactgg ggtgaagtcg                                              20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
taaccttcgg gagggcgmtt                                              20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
wtsggagtgg gytgcaaaag                                              20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 364
ccgtcacacc atgggagtgk                                               20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
gsgccctccm gaagrttaag                                               20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
acttcacycc agtcatgaak                                               20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
ccgaaggtta agctacctac                                               20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
acwaagtggt aagcgcccyc                                               20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
caaastggwa agcgccctcc                                               20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
```
cttgttacga cttcacccca                                               20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
wttgcaaccc actcccatgg                                               20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
ggtaagcgcc ctcccgaagg                                               20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
actcccatgg tgtgacgggc                                               20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
cttcacccca gtcatgaatc                                               20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
ctacctactt cttttgcamc                                               20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
saatcwcaaa gtggkaagcg                                            20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
acctacytct tttgcaaccc                                            20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
cccctacggt taycttgtta                                            20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
gtggtaagcg ccytccckaa                                            20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
ttctwttgca acccwctccc                                            20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
ccgraggtta agctacctac                                            20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
ccctcccgaa ggttaagcta                                            20

```
<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
cctacttctt ttgcaaccya                                              20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
cgaaggttaa gctacctact                                              20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
rtgaatcaca aagtggtaag                                              20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
ctcccgaagg ttaagctacc                                              20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
tacgacttca ccccagtcat                                              20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
tacggttacc ttgttacgac                                              20
```

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 389
ctacktcttt tgcaamccac                                              20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 390
gctacctact tcttttscam                                              20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 391
gtaagcgcmc tcccgaaggt                                              20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 392
aagcgcmctc ccgaaggtta                                              20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 393
actcccatgg tgtgacsggc                                              20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 394
ttgttacgac ytcwccccag                                              20

```
<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
aatcacaaag tggtaagcgy                                               20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
tsacaaagtg gtaagcgccc                                               20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
cagtcatgaa tcacaaagtg                                               20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
tttkcaaccc actcscatgg                                               20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
catkaatcac aaagtggtaa                                               20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
aaggttaagc tacctacytc                                               20

<210> SEQ ID NO 401
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
ttcaccccag tcatgaatca                                                   20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
ggttaagcta cstacttctt                                                   20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
caacccwctc ccatggtgtg                                                   20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
acctacttct tttgcaaccc                                                   20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
acggttacct tgttacgact                                                   20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
taagcgccct cccgaaggtt                                                   20

<210> SEQ ID NO 407
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
tcaccccagt catgaatcac                                                    20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
gtaagcgccc tcccgaaggt                                                    20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
acsacttcac cccagtcatg                                                    20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
caacccactc ccatggtgtg                                                    20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
agtcatgaat cacaaastgg                                                    20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
ttaccttgtt wcgacttcac                                                    20

<210> SEQ ID NO 413
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 413
gttacgamtt caccccagtc                                            20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
actccmatgg tgtsacgggc                                            20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
tcaccscagt catgaatcac                                            20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
gsaacccact cccatggtgy                                            20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
rttacgactt caccccagtc                                            20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
gtcatgaatc acaaagtgkt                                            20

<210> SEQ ID NO 419
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 419
tcacaaagtg gtaagcgccc                                                   20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
cttttgcaay ccactcccat                                                   20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
tcccgaargt taagctacct                                                   20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
catgaaycac aaagtggtaa                                                   20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
cccctacggt taccttgkta                                                   20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
ctacctmctt cttttgcaac                                                   20

<210> SEQ ID NO 425
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 425
ttttgcracc cactcccrtg                                                   20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
tcatgaatca caaagtggtw                                                   20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
cacaaagtgk taagcgccct                                                   20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
aaggytaagc tayctacttc                                                   20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
cttttrcaac ccactcccat                                                   20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
ttttgcaasc cactcccatg                                                   20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 431
ctacttcttt tgsaacccac                                               20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
ytcacmccag tcatgaatca                                               20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
acgacttcac cccagtcatg                                               20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
aagcgccctc ccgaaggtta                                               20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
gcaacccact cccatggtgt                                               20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
cctacttctt wtscaaccca                                               20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 437
agtggtaagc gccmtcccga                                               20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
cscagtcats aakcacaaag                                               20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
crtgaatcam aaagtggtaa                                               20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
gtcatgaatc acamagtggt                                               20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
rgctacctac ttcttttgcm                                               20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
ttaagctacc tacttctttt                                               20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 443
cagtcrtgam tcacaaagkg                                          20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
tcttttgcra cccactcccr                                          20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
gtaagcgcsc tcccgaaggt                                          20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
ggttaagsta cctacttctt                                          20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
cccctamggt taccttsttr                                          20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
tgttacgact tcaccccakt                                          20

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
taagcwacct acttcttttg                                                   20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
cttcttttgc aacccactcc                                                   20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
gaaggttaag ctacctactt                                                   20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
taccttgtta cgacttcacy                                                   20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
tcccctacgg ttaccttgtt                                                   20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
gttaccwtgt tacgacttca                                                   20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
cactyccatg gtgtgacggg                                          20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
tcacaaastg gtaagcgccc                                          20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
ccctacggtt accttgttac                                          20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
tcccctacgg ttamcttgtt                                          20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
ccctcccgaa ggktaagcta                                          20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
cctcccgaag gttaagctac                                          20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
gtaagcsccc tcccgaaggt                                          20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
ctaagcgyac acggtggatg                                            20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
tcggtaaggt gatatgaacc                                            20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
ccctggsagt cagaggcgat                                            20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
atgaaccgtt ataaccggcg                                            20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
cagtcagagg cgatgaagga                                            20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
cygttataac cggsgatttc                                            20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 468
agcgacwaag cgtacacggt                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 469
ycagaggcga tgaaggacgt                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 470
taatcygcga taagcgtcsg                                              20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 471
tgakatgaac cgttataacc                                              20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 472
cacggtkkat gccctggcag                                              20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 473
gcgtacacgg tggatgccct                                              20

-continued

```
<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
taagcgtcgg waaggtgata                                                    20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
ywcacggtgg atgccctggc                                                    20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
ggcagtcaga ggcgatgaag                                                    20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
gtcggtaagg tgatatgawc                                                    20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
aggtgatatg aaccgttatr                                                    20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
wggcagtcag aggcgatraa                                                    20

<210> SEQ ID NO 480
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
cggtggatgc cctggcagtc                                              20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481
ttataaccgg cgatttcyga                                              20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
gcgtcggtaa ggtgatatga                                              20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
accgttataa ccggcgattt                                              20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
tmatctgcga taagcgtcgg                                              20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
gcgtacacgg tggrtgccct                                              20

<210> SEQ ID NO 486
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
tcagaggcga tgaaggacgt                                              20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
tamgcgtcgg taargtkata                                              20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
atatgaaccg ttataaccgg                                              20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
tatarccggc gatttccgaa                                              20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
tataaccggc gatttccgaa                                              20

<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
taargtgata tgaaccgkta                                              20

<210> SEQ ID NO 492
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 492
tgccctggca gtcagaggcg                                            20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
tmaggtgata tsaaccrtta                                            20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
gttargcgac taagcgtaca                                            20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
tatgraccgt tataaccgrc                                            20

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
cagtcagagg cgrtgaagsa                                            20

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
cagaggcgat gaaggacgtg                                            20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
atgccctggc agtcasaggc                                               20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
atctgcgata agcgtcggta                                               20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
aggacgtgct aatctgcgat                                               20

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
tctgcgataa gygtcggtaa                                               20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
cgactaagcr tacacggtgg                                               20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
ggcagtcaka ggsgawgaag                                               20

<210> SEQ ID NO 504
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 504
cgactaagcg twcacggtgg                                              20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
taaggtgaka tgaaccgtka                                              20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
ccctggcagt cagaggcgat                                              20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
ggtaakgtga katgaaccgt                                              20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
ttataaccgg cgatttccgr                                              20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
gaaccgttat aaccggcgrt                                              20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 510
gtgctaatct gcgataagcg                                           20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
cacggtggat gccctggcag                                           20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
cgactaagcg tacrcgstgg                                           20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
acggyggatg cmctggcagt                                           20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
atgaaggacg tgctamyctg                                           20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
aagygtacac ggtggatgcc                                           20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 516
tgaaggacgt gctaatctgc                                              20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
rttaagcgac tmagcgtaca                                              20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
gtgatatgaa ccgttataac                                              20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
agcgactaar cgtacacggt                                              20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 520
aaccgttata accggcgatt                                              20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 521
gtacacggtg gatgccctgg                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 522
ggttaagcsa ctaagcgtac                                               20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
tgcgataagc gtcggtaagg                                               20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
aaggacgtkc taatctgcga                                               20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 525
gatgccctgg magtcakagg                                               20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526
atgaaggacg tgcyaatctg                                               20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 527
atgccctggc agtcagaggc                                               20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 528
gtgatatsaa scgttataac                                              20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
ccgttayaac cggcgatttc                                              20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530
gtgctaatct gcgataakcg                                              20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531
aagrwcgtgs taatctgcga                                              20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532
aatctgcgat aagcgtcggt                                              20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 533
ygataagcgt cggtaaggtg                                              20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 534
gaaccgttat aaccggcgat                                              20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 535
gataascgkc ggtaaggwga                                              20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 536
gytaatctgc gataagcgyc                                              20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 537
sgtcggtaag gtgatatgaa                                              20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
tgaaccgtta taaccggcga                                              20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 539
gtgcyratct gcgataagcs                                              20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540
ctgsgakaag cgtcggtaag                                              20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
tgcgataagc gtcggtaarg                                           20

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
tggcagtcag aggcgatgra                                           20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543
gatgaaggac gtgctaatct                                           20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
mgmggcgatg aaggacgygc                                           20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
ctggcagtca gaggcgatga                                           20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
tgaaggamgt gctaatctgm                                           20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 547
gaggcgatga aggacgtgct                                              20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 548
ataagcgtcr gtaaggtgat                                              20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 549
ggatgccctg gcagtcagag                                              20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 550
ggtwaggtga tatgaaccrt                                              20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 551
ttcatatcac yttaccsayg                                              20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 552
acgcttatcg sagattagca                                              20

-continued

```
<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
tagcacgtcm ttcatcgcct                                                 20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
accgaygctt atcgcagatt                                                 20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
ytcatatcac cttaccsacg                                                 20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
ccttcatcgc ctctgactgc                                                 20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
ccaccgtgta cgcttagtcg                                                 20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
cggttataac ggttcatatc                                                 20

<210> SEQ ID NO 559
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
ctgactgyca sggcatccac                                              20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
gcacgtcctt catcgcctct                                              20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
gcsggttawa acggttcata                                              20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
acggttsatm tcaccttacc                                              20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
ttataasggt tcatatcacc                                              20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 564
cggttcatat caccttmccg                                              20

<210> SEQ ID NO 565
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 565
cttaccgacg cttatcgcag                                                    20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 566
gggcatccrc cgtgtacgct                                                    20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 567
tagcacgtcc wtcatcgcct                                                    20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 568
cgtgtacgct twgtcgcttw                                                    20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
racggktcat atcaccttac                                                    20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
cggttataac grttcatatc                                                    20

<210> SEQ ID NO 571
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 571
ggttcatatc accttaccga                                            20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 572
cctctgactg ccagggcatc                                            20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 573
ttcatatcac cttacygacg                                            20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 574
tctgackgcc aggrcatcca                                            20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 575
ccaccgtgta cgcttagycg                                            20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 576
cgacgcttat cgcagattag                                            20

<210> SEQ ID NO 577
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 577
atcgcctctg actgccaggg                                              20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
wgcacgtcct tcatcgcctc                                              20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
aacggttsat atcaccttac                                              20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
catcgcctct gmckgccagg                                              20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
ttaccgacgc ttatcgcaga                                              20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
tcatcgcctc wgactgccag                                              20

<210> SEQ ID NO 583
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 583
accttaccga cgcttatcgc                                              20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
gttcatatca ccttaccgam                                              20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
attagcrcgt ccttcatcgc                                              20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
cgtccttcat cgcctctgac                                              20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
tcaccttacc gacgcttatc                                              20

<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 588
ctctgactgc cagggcatcc                                              20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 589
crgttataac ggttcatatc                                         20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590
tkccagggca tccaccgtgt                                         20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 591
gactgccmgg gcatccamcs                                         20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 592
atatcacctt ascgacgcwt                                         20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 593
agggcatcca cmgtgtacgc                                         20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 594
gccagggcat ccaccgtgta                                         20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 595
gcagattagc acgtccttca                                              20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
gyttatcgca gattarcacg                                              20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
gcakattagc acgtccttca                                              20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 598
aacggttcat atcaccttac                                              20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 599
kacgcttatc gcwgattagc                                              20

<210> SEQ ID NO 600
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 600
ttacygacgc ttatcgcaga                                              20

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 601
cgcttatcgc agattagcac                                              20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
cgtccttcat cgmctctgrc                                              20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
twaccgacgc ttatcgcaga                                              20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 604
gccggttata acggttcaya                                              20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
gcatmcaccg tgtaygstta                                              20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
cggmaatcgc cggttataac                                              20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 607
```

```
ccgtgtacgc ttagkcgctt                                          20
```

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608

```
ktaccgacgc ttatcgcaga                                          20
```

<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609

```
cgcttatcgc agattmgcac                                          20
```

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 610

```
acggttcata tcaccytacc                                          20
```

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611

```
cctctgwctg ccagggcatc                                          20
```

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612

```
gcttrtcgca gattagcacg                                          20
```

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 613
ggcatccacc gtgtacgctt                                              20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 614
ggcatccacc stgtacgctt                                              20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 615
tatsacctta ccgacgctta                                              20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 616
tmgcmgatta gcacgtsmtt                                              20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 617
tcgcagatta gcaygtcctt                                              20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 618
tatcayctta ccgaygctta                                              20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
acgtccttca tcgcctctga                                              20

```
<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
gggcatccac cgtgtacgct                                                    20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
acggttcata tcaccttmcc                                                    20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
agggcatccr ccgtgtacgc                                                    20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
catakmrcct trccgacsct                                                    20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 624
gacgcttatc gcakattagc                                                    20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
tccttcatcg cctctgactg                                                    20
```

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 626
gttcatatcm ccttrccgac                                               20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 627
tcggaaatcg ccggktataa                                               20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 628
acgcttatcg cagattagca                                               20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 629
gttcatatca ccttaccgac                                               20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 630
gycagggcat mmacmstgta                                               20

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 631
tcacyttacc gacscttakc                                               20

```
<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 632
tagcacgtcs ttcatcgcct                                               20

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 633
tcgcctctga ckgccagggc                                               20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 634
gggcatccmc cgtgtacgct                                               20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 635
ggttcrtatc acmttaccga                                               20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 636
atcgcagatt agcacgtcct                                               20

<210> SEQ ID NO 637
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 637
tcgccggtta taackgttca                                               20

<210> SEQ ID NO 638
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 638
agcacgtcct tcatcgcctc                                              20

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 639
gcttatcgca gattagcrcg                                              20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 640
tatcaccttw ccgacgctta                                              20

<210> SEQ ID NO 641
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 641
cggttcatat cascttaccg                                              20

<210> SEQ ID NO 642
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 642
atcgcctctg rmtgcyaggg                                              20

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 643
tcyaccgtgt acgcttagwc                                              20

<210> SEQ ID NO 644
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 644
tcgcagatta gcacgtcctt                                                  20

<210> SEQ ID NO 645
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 645
tscaccgtgt acgcttagtc                                                  20
```